(12) United States Patent
Bennett et al.

(10) Patent No.: US 6,900,306 B2
(45) Date of Patent: May 31, 2005

(54) ANTISENSE MODULATION OF COREST EXPRESSION

(75) Inventors: C. Frank Bennett, Carlsbad, CA (US); Susan M. Freier, San Diego, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 17 days.

(21) Appl. No.: 09/920,671

(22) Filed: Aug. 1, 2001

(65) Prior Publication Data

US 2003/0083283 A1 May 1, 2003

(51) Int. Cl.[7] .......................... C07H 21/04; C12N 15/00
(52) U.S. Cl. ..................... 536/24.5; 435/6; 536/23.1; 536/24.1
(58) Field of Search ............................. 435/375, 377; 536/24.1, 24.5; 514/44

(56) References Cited

U.S. PATENT DOCUMENTS 5,801,154 A * 9/1998 Baracchini et al.
5,998,148 A * 12/1999 Bennett et al.

OTHER PUBLICATIONS

Weintraub H., Scientific American, pp. 40–46, 1990.*
Jen et al., Stem Cells, vol. 18:307–319, 2000.*
Agrawal et al., TIBTECH vol. 14:376–387, 1996.*
Branch A., TIBS, vol. 23:45–50, 1998.*
Aasland et al., *The SANT domain: a putative DNA—binding domain in the SWI—SNF and ADA complexes, the transcriptional co–repressor N–CoR and TFIIIB*, Trends Biochem. Sci., 1996, 21:87–88.

Andres et al., *CoREST: a functional corepressor required for regulation of neural–specific gene expression*, Proc. Natl. Acad. Sci. U. S. A., 1999, 96:9873–9878.

Ayer, *Histone deacetylases: transcriptional repression with SINers and NuRDs*, Trends in Cell Biology, 1999, 9:193–198.

DePinho, *Transcriptional repression. The cancer–chromatin connection*, Nature, 1998, 391:533, 535–536.

Grimes et al., *The co–repressor mSin3A is a functional component of the REST–CoREST repressor complex*, J. Biol. Chem., 2000, 275:9461–9467.

Humphrey et al., *Stable histone deactylase complexes distinguished by the presence of SANT domain proteins CoREST/kiaa0071 and Mta–L1*, J. Biol. Chem., 2001, 276:6817–6824.

Kouzarides, *Histone acetylases and deacetylases in cell proliferation*, Current Opinion in Genetics & Development, 1999, 9:40–48.

You et al., *CoREST is an integral component of the CoREST—human histone deacetylase complex*, Proc. Natl. Acad. Sci. U. S. A., 2001, 98:1454–1458.

* cited by examiner

Primary Examiner—Sean McGarry
(74) Attorney, Agent, or Firm—ISIS Patent Department

(57) ABSTRACT

Antisense compounds, compositions and methods are provided for modulating the expression of CoREST. The compositions comprise antisense compounds, particularly antisense oligonucleotides, targeted to nucleic acids encoding CoREST. Methods of using these compounds for modulation of CoREST expression and for treatment of diseases associated with expression of CoREST are provided.

11 Claims, No Drawings

ANTISENSE MODULATION OF COREST EXPRESSION

FIELD OF THE INVENTION

The present invention provides compositions and methods for modulating the expression of CoREST. In particular, this invention relates to compounds, particularly oligonucleotides, specifically hybridizable with nucleic acids encoding CoREST. Such compounds have been shown to modulate the expression of CoREST.

BACKGROUND OF THE INVENTION

The DNA of all eukaryotic cells wraps around histone proteins to form nucleosomes, the basic structure of chromatin. Histones are essential for this packaging of DNA within the chromosomes, and mutation of individual histones in vivo alters the general organization of chromatin throughout the eukaryotic nucleus. A number of posttranslational reactions, such as phosphorylation, acetylation, ADP-ribosylation, and ubiquitination, reversibly modify histones. The acetylation state of histones can affect structural alterations in local chromatin architecture during nuclear processes such as transcription. Furthermore, histone deacetylation plays a pivotal role in controlling access of transcriptional activators and the basal transcription machinery to regulatory sequences in the underlying DNA template, and positively or negatively affects the rate of gene transcription.

The dynamic state of histone acetylation is tightly regulated and maintained by histone acetyltransferase and histone deacetylase enzyme activities. It is widely held that acetylation of core histones destabilizes local nucleosome structure and allows transcription factor access. Conversely, deacetylation causes a tighter association between DNA and histones and favors transcriptional repression and gene silencing (Ayer, *Trends in Cell Biology*, 1999, 9, 193–198).

Modulation of chromatin architecture by nucleosome remodeling and deacetylating complexes is implicated in control of cell cycle progression, and in both the genesis and the suppression of cancer (DePinho, *Nature*, 1998, 391, 533, 535–536). Support for this hypothesis comes from the observation that histone deacetylases mediate the function of the chromosomal translocation/gene fusion proteins PML-RARα and PLZF-RARα, and of the frequently mutated tumor suppressor protein RB, contributing to the development of cancers such as acute promyelocytic leukemia (Kouzarides, *Current Opinion in Genetics & Development*, 1999, 9, 40–48).

Mammalian histone deacetylases 1 and 2, (HDAC1 and HDAC2) have been well characterized and previously found to exist in either of two large, multisubunit protein complexes, called the mSin3 complex (named for one component homologous to the yeast SIN3 gene) and the NuRD complex (nucleosome remodeling and deacetylating). The emerging model of the function of these HDAC-containing complexes is that they are recruited for transcriptional repression under one set of conditions and released and exchanged for histone acetyltransferase coactivators under a different set of conditions. Recently, however, a novel third HDAC1/2-associated complex, distinct from the mSin3 and NuRD complexes, was identified and found to contain a protein called CoREST (You et al., *Proc. Natl. Acad. Sci. U.S.A.*, 2001, 98, 1454–1458).

CoREST (also known as KIAA0071) was identified previously as a corepressor for REST/NRSF (RE1 silencing transcription factor/neural restrictive silencing factor), a transcription factor involved in maintenance of cellular identity by mediating long-term repression of neural-specific genes in non-neural cells. At its C-terminus, CoREST contains two SANT (SWI3/ADA2/NCoR/TFIIIB B") domains, a structural feature also present in the nuclear receptor corepressor (NCoR)/silencing mediator for retinoic acid and thyroid hormone receptors-extended (SMRTe) proteins (Aasland et al., *Trends Biochem. Sci.*, 1996, 21, 87–88; Andres et al., *Proc. Natl. Acad. Sci. U.S.A.*, 1999, 96, 9873–9878).

The SMRT and NCoR corepressor proteins both form complexes with mSin3 and histone deacetylases to induce local chromatin condensation and mediate transcriptional silencing of important regulators. With the finding that the CoREST protein is also stably associated with HDAC1/2 complexes purified from HeLa cell extract (You et al., *Proc. Natl. Acad. Sci. U.S.A.*, 2001, 98, 1454–1458), it appears that a corepressor family of SANT domain-containing transcriptional repressors regulates important signaling pathways via chromatin remodeling complexes. SANT domain proteins may play a general role in HDAC complex assembly (Humphrey et al., *J. Biol. Chem.*, 2001, 276, 6817–6824), where the composition of the alternative histone deacetylase complexes mediate specific repression pathways (Grimes et al., *J. Biol.Chem.*, 2000, 275, 9461–9467).

A model for the role of different HDAC complexes is that the mSin3-HDAC complex is recruited for simple deacetylation of dynamically regulated promoters, whereas the NuRD and CoREST containing HDAC complexes are recruited to promoters that require stable repression, such as for tissue specific silencing, or for heritable epigenetic states such as genomic imprinting. The associated non-HDAC enzymatic activities may determine the nature of the repression (You et al., *Proc. Natl. Acad. Sci. U.S.A.*, 2001, 98, 1454–1458).

In contrast to REST, which is expressed only in non-neuronal cell lines, CoREST was found to be expressed in all human tissues and all cell lines tested (Andres et al., *Proc. Natl. Acad. Sci. U.S.A.*, 1999, 96, 9873–9878). The CoREST protein is localized to the nucleoplasm and excluded from nucleoli of human skin fibroblasts (Humphrey et al., *J. Biol. Chem.*, 2001, 276, 6817–6824). During development of mouse embryonic tissues, however, the expression pattern of CoREST is restricted. Specifically, in early embryogenesis, mSin3 is widely expressed throughout the embryo, but CoREST expression is only strongly expressed in the head mesenchyme, whereas later in development, this disparity is no longer apparent. This suggests that the composition of the REST repressor complex during development is dynamic and that CoREST may be recruited for more specialized repressor functions (Grimes et al., *J. Biol.Chem.*, 2000, 275, 9461–9467). The CoREST protein is localized to the nucleoplasm and excluded from nucleoli of human skin fibroblasts (Humphrey et al., *J. Biol. Chem.*, 2001, 276, 6817–6824).

The pharmacological modulation of the activity and/or expression components of histone deacetylase/corepressor complexes is believed to be an appropriate point of therapeutic intervention in pathological conditions such as cancer.

Currently, there are no known therapeutic agents which effectively inhibit the synthesis of CoREST and investigative strategies aimed at studying CoREST function have involved the use of antibodies for purification and cellular localization studies. Therefore, there exists a long felt need to identify methods of modulating transcriptional repression complexes and specifically for agents capable of effectively modulating CoREST function.

Antisense technology is emerging as an effective means for reducing the expression of specific gene products and may therefore prove to be uniquely useful in a number of therapeutic, diagnostic, and research applications for the modulation of CoREST expression.

The present invention provides compositions and methods for modulating CoREST expression.

SUMMARY OF THE INVENTION

The present invention is directed to compounds, particularly antisense oligonucleotides, which are targeted to a nucleic acid encoding CoREST, and which modulate the expression of CoREST. Pharmaceutical and other compositions comprising the compounds of the invention are also provided. Further provided are methods of modulating the expression of CoREST in cells or tissues comprising contacting said cells or tissues with one or more of the antisense compounds or compositions of the invention. Further provided are methods of treating an animal, particularly a human, suspected of having or being prone to a disease or condition associated with expression of CoREST by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding CoREST, ultimately modulating the amount of CoREST produced. This is accomplished by providing antisense compounds which specifically hybridize with one or more nucleic acids encoding CoREST. As used herein, the terms "target nucleic acid" and "nucleic acid encoding CoREST" encompass DNA encoding CoREST, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of CoREST. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding CoREST. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding CoREST, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6-substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of CoREST is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding CoREST, enabling sandwich and other assays to easily be constructed to exploit this fact. Hybridization of the antisense oligonucleotides of the invention with a nucleic acid encoding CoREST can be detected by means known in the art. Such means may include conjugation of an enzyme to the oligonucleotide, radiolabelling of the oligonucleotide or any other suitable detection means. Kits using such detection means for detecting the level of CoREST in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), U.S. applications Ser. No. 09/108,673 (filed Jul. 1, 1998), U.S. applications Ser. No. 09/256,515 (filed Feb. 23, 1999), U.S. applications Ser. No. 09/082,624 (filed May 21, 1998) and U.S. applications Ser. No. 09/315, 298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 µm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534, 899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., J. Pharm. Exp. Ther., 1992, 263, 25; Yamashita et al., J. Pharm. Sci., 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., J. Control Rel., 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., J. Pharm. Pharmacol., 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bischloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL.) The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160 ° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S.

Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 containing 3.75 µg/mL LIPO-FECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of CoREST Expression

Antisense modulation of CoREST expression can be assayed in a variety of ways known in the art. For example, CoREST mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of CoREST can be quantitated in a variety of ways well known in the art, such as immunoprecipitation, Western blot analysis (immunoblotting), ELISA or fluorescence-activated cell sorting (FACS). Antibodies directed to CoREST can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of CoREST mRNA Levels

Quantitation of CoREST mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM $MgCl_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human CoREST were designed to hybridize to a human CoREST sequence, using published sequence information (GenBank accession number NM_015156, incorporated herein as SEQ ID NO:3). For human CoREST the PCR primers were: forward primer: ACAATCCCATTGACATTGAGGTT (SEQ ID NO: 4) reverse primer: TTTGCTCTATTTTAGCTTGTGTGCT (SEQ ID NO: 5) and the PCR probe was: FAM-AAGGAGGTTCCCCCTACTGAGACAGTTCCT-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: GAAGGTGAAGGTCG-GAGTC (SEQ ID NO: 7) reverse primer: GAAGATGGT-GATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of CoREST mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human CoREST, a human CoREST specific probe was prepared by PCR using the forward primer ACAATCCCATTGACATTGAGGTT (SEQ ID NO: 4) and the reverse primer TTTGCTCTATTTTAGCTTGTGTGCT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human CoREST Expression by Chimeric Phosphorothioate Oligonucleotides Having 2'-MOE Wings and a Deoxy Gap In accordance with the present invention, a series of oligonucleotides were designed to target different regions of the human CoREST RNA, using published sequences (GenBank accession number NM_015156, incorporated herein as SEQ ID NO: 3, Genank accession number D31888, incorporated herein as SEQ ID NO: 10, genomic sequence of human CoREST, incorporated herein as SEQ ID NO: 11, GenBank accession number AI922671, the complement of which is incorporated herein as SEQ ID NO: 12, and GenBank accession number BE831704, the complement of which is incorporated herein as SEQ ID NO: 13). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human CoREST mRNA levels by quantitative real-time PCR described in other examples herein. Data are averages from two experiments. If present, "N.D." indicates "no data".

TABLE 1

Inhibition of human CoREST mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 164963 | Coding | 3 | 258 | tggacgagcc cgagctgcct | 83 | 14 |
| 164964 | Coding | 3 | 394 | ttgggtgacc agaccaacat | 89 | 15 |
| 164965 | Coding | 3 | 412 | gcttctgaca gattttgatt | 37 | 16 |
| 164966 | Coding | 3 | 480 | tcccaagagc ctgttccatg | 85 | 17 |
| 164967 | Coding | 3 | 527 | caaatcagcc aatgactttt | 84 | 18 |
| 164968 | Coding | 3 | 657 | gacttgctat agatttatct | 75 | 19 |
| 164969 | Coding | 3 | 704 | actagtttta gtcctcgtct | 83 | 20 |
| 164970 | Coding | 3 | 795 | tgtcaatggg attgtttcca | 88 | 21 |
| 164971 | Coding | 3 | 859 | acctgaggaa ctgtctcagt | 9 | 22 |
| 164972 | Coding | 3 | 865 | tttttgacct gaggaactgt | 94 | 23 |
| 164973 | Coding | 3 | 924 | acattcctttt tggaggttttc | 88 | 24 |
| 164974 | Coding | 3 | 940 | tcttcttgag aaagaaacat | 51 | 25 |
| 164975 | Coding | 3 | 945 | ccacatcttc ttgagaaaga | 77 | 26 |
| 164976 | Coding | 3 | 952 | acagcctcca catcttcttg | 89 | 27 |
| 164977 | Coding | 3 | 971 | agcagtggca ttggcagaaa | 89 | 28 |
| 164978 | Coding | 3 | 1081 | attccaccat caagtttttc | 46 | 29 |
| 164979 | Coding | 3 | 1113 | tctgaatgac ctctggaagt | 80 | 30 |
| 164980 | Coding | 3 | 1121 | attacatttc tgaatgacct | 57 | 31 |
| 164981 | Coding | 3 | 1157 | tacggcgaga agctgctctt | 49 | 32 |

TABLE 1-continued

Inhibition of human CoREST mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 164982 | Coding | 3 | 1165 | atggcttgta cggcgagaag | 75 | 33 |
| 164983 | Coding | 3 | 1171 | ttcctgatgg cttgtacggc | 57 | 34 |
| 164984 | Coding | 3 | 1243 | aaaaagtttt tcacttgtac | 84 | 35 |
| 164985 | Coding | 3 | 1259 | gcgtcgataa tttacaaaaa | 79 | 36 |
| 164986 | Coding | 3 | 1275 | catctatgtt gaagcggcgt | 84 | 37 |
| 164987 | Coding | 3 | 1280 | aacttcatct atgttgaagc | 83 | 38 |
| 164988 | Coding | 3 | 1285 | tgtaaaactt catctatgtt | 65 | 39 |
| 164989 | Coding | 3 | 1290 | attcttgtaa aacttcatct | 71 | 40 |
| 164990 | Coding | 3 | 1294 | tcccattctt gtaaaacttc | 67 | 41 |
| 164991 | Coding | 3 | 1401 | gaacaggagc ctcgtcttcc | 69 | 42 |
| 164992 | Stop Codon | 3 | 1430 | tcaggagca gatgcatatc | 88 | 43 |
| 164993 | 3'UTR | 10 | 1205 | agtccacacc aagtgttcaa | 91 | 44 |
| 164994 | 3'UTR | 10 | 1255 | cagatggcta ggtgatgtct | 80 | 45 |
| 164995 | 3'UTR | 10 | 1260 | tgatgcagat ggctaggtga | 82 | 46 |
| 164996 | 3'UTR | 10 | 1265 | agatgtgatg cagatggcta | 87 | 47 |
| 164997 | 3'UTR | 10 | 1290 | tttggtaata gctgcttgtc | 89 | 48 |
| 164998 | 3'UTR | 10 | 1434 | caagagatgt gcaggccgtg | 78 | 49 |
| 164999 | 3'UTR | 10 | 1557 | caggccatgc aggaacagag | 86 | 50 |
| 165000 | 3'UTR | 10 | 1562 | aactgcaggc catgcaggaa | 80 | 51 |
| 165001 | 3'UTR | 10 | 1569 | aagtagaaac tgcaggccat | 87 | 52 |
| 165002 | 3'UTR | 10 | 1649 | ggttgtctca gaaaagaaca | 77 | 53 |
| 165003 | 3'UTR | 10 | 1671 | aaaagcgtat tatcacttag | 93 | 54 |
| 165004 | 3'UTR | 10 | 1771 | atcataactg taccccatgt | 14 | 55 |
| 165005 | 3'UTR | 10 | 1990 | gtgatgtggg ccgaacctct | 81 | 56 |
| 165006 | 3'UTR | 10 | 2032 | aaggagaagg caccaattcc | 87 | 57 |
| 165007 | 3'UTR | 10 | 2296 | atcagcacat gaaggacaca | 88 | 58 |
| 165008 | 3'UTR | 10 | 2450 | aaatttttac ttgttcccag | 93 | 59 |
| 165009 | 3'UTR | 10 | 2821 | cctaggtttc tagctgaccc | 66 | 60 |
| 165010 | 3'UTR | 10 | 3242 | agacctattg gcagggtgag | 76 | 61 |
| 165011 | 3'UTR | 10 | 3421 | cacgtgattc ttcagggctg | 74 | 62 |
| 165012 | 3'UTR | 10 | 3433 | ctgctgtgat cacacgtgat | 67 | 63 |
| 165013 | 3'UTR | 10 | 3659 | atatgttaaa aagtcttcat | 76 | 64 |
| 165014 | 3'UTR | 10 | 3665 | ttcttgatat gttaaaaagt | 64 | 65 |
| 165015 | 3'UTR | 10 | 3735 | acaaagctta agtgaacatt | 74 | 66 |
| 165016 | 3'UTR | 10 | 4117 | tgtgttacac tagcacccga | 71 | 67 |
| 165017 | 3'UTR | 10 | 4146 | aacactgtac acccagacaa | 90 | 68 |
| 165018 | 3'UTR | 10 | 4198 | cttataggtt aaaaacaatc | 52 | 69 |
| 165019 | 3'UTR | 10 | 4408 | ctgatattta gaatgacaaa | 76 | 70 |
| 165020 | 3'UTR | 10 | 4553 | tttagaaaca ggctagacaa | 79 | 71 |
| 165021 | 3'UTR | 10 | 4729 | acgccactgc aattgtgctt | 86 | 72 |
| 165022 | 3'UTR | 10 | 4749 | cttcccttct tctgaatgcg | 85 | 73 |
| 165023 | 3'UTR | 10 | 4823 | cggtataaat ttcgttttag | 86 | 74 |
| 165024 | 3'UTR | 10 | 4845 | cctaatggaa tactatccac | 59 | 75 |
| 165025 | 3'UTR | 10 | 4935 | tatatttgca aacttaacct | 78 | 76 |
| 165026 | 3'UTR | 10 | 5065 | atgaatgtgc tgaaatagaa | 56 | 77 |
| 165027 | 3'UTR | 10 | 5192 | ccctcagcaa atattggaaa | 78 | 78 |
| 165028 | Genomic | 11 | 29899 | gagtaagaaa gagaggttac | 12 | 79 |
| 165029 | Genomic | 11 | 48225 | caggtgtctc gatctccatg | 95 | 80 |
| 165030 | Genomic | 11 | 57981 | cctcccaaag tgccaggatt | 55 | 81 |
| 165031 | Genomic | 11 | 72853 | aatcccagct actcgggagg | 94 | 82 |
| 165032 | Genomic | 11 | 88745 | gccagtttgg cttgggagaa | 39 | 83 |
| 165033 | Genomic | 11 | 117790 | ttcatcctcg ctggaagaca | 79 | 84 |
| 165034 | Genomic | 11 | 129272 | tcagatttac ctcgtcttcc | 0 | 85 |
| 165035 | Genomic | 11 | 133323 | gaacaggagc ctgaggccaa | 81 | 86 |
| 165036 | Genomic | 12 | 220 | gtccttatga gcttaacgaa | 60 | 87 |
| 165037 | Genomic | 12 | 280 | tctgaatgac ctggatatcc | 74 | 88 |
| 165038 | Genomic | 12 | 338 | ttccccctac cttgtacggc | 75 | 89 |
| 165039 | Genomic | 12 | 381 | gtgtgagcca ccacagccgg | 80 | 90 |
| 165040 | Genomic | 13 | 51 | ctgatggctc tggaagtcga | 68 | 91 |

As shown in Table 1, SEQ ID NOs 14, 15, 17, 18, 19, 20, 21, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 80, 81, 82, 84, 86, 87, 88, 89, 90 and 91 demonstrated at least 40% inhibition of human CoREST expression in this assay and are therefore preferred. The target sites to which these preferred sequences are complementary are herein referred to as "active sites" and are therefore preferred sites for targeting by compounds of the present invention.

Example 16
Western Blot Analysis of CoREST Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to CoREST is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 20 to 50 nucleobases in length targeted to a nucleic acid molecule encoding CoREST (SEQ ID NO:11), wherein said compound specifically hybridizes with said nucleic acid molecule encoding CoREST (SEQ ID NO:11) and inhibits the expression of CoREST, wherein said compound is an antisense oligonucleotide and has a sequence comprising SEQ ID NO:80.

2. The compound of claim 1 wherein the antisense oligonucleotide comprises at least one modified internucleoside linkage.

3. The compound of claim 2 wherein the modified internucleoside linkage is a phosphorothioate linkage.

4. The compound of claim 1 wherein the antisense oligonucleotide comprises at least one modified sugar moiety.

5. The compound of claim 4 wherein the modified sugar moiety is a 2'-O-methoxyethyl sugar moiety.

6. The compound of claim 1 wherein the antisense oligonucleotide comprises at least one modified nucleobase.

7. The compound of claim 6 wherein the modified nucleobase is a 5-methylcytosine.

8. The compound of claim 1 wherein the antisense oligonucleotide is a chimeric oligonucleotide.

9. An antisense compound 20 to 50 nucleobase in length which specifically hybridizes with nucleobases 48225 to 48244 of a nucleic acid molecule encoding CoREST (SEQ ID NO: 11) and which inhibits expression of CoREST.

10. A composition comprising the compound of claim 1 and a pharmaceutically acceptable carrier or diluent.

11. The composition of claim 10 furter comprising a colloidal dispersion system.

* * * * *

SEQUENCE LISTING

```
<160> NUMBER OF SEQ ID NOS: 91

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 1449
<212> TYPE: DNA
<213> ORGANISM: Homo sapiens
<220> FEATURE:
<221> NAME/KEY: CDS
<222> LOCATION: (1)...(1449)

<400> SEQUENCE: 3 atg gtg gag aag ggc ccc gag gtc tca ggg aag cgg aga ggg agg aac      48
Met Val Glu Lys Gly Pro Glu Val Ser Gly Lys Arg Arg Gly Arg Asn
 1               5                  10                  15 aac gcg gcc gcc tcc gcc tcc gcc gcc gcc gcc tcc gcc gcc gcc tcg      96
Asn Ala Ala Ala Ser Ala Ser Ala Ala Ala Ala Ser Ala Ala Ala Ser
             20                  25                  30 gcc gcc tgc gcc tcg cca gcc gcc act gcc gcc tcg ggc gcc gcc gcc     144
Ala Ala Cys Ala Ser Pro Ala Ala Thr Ala Ala Ser Gly Ala Ala Ala
         35                  40                  45 tcc tca gcc tcg gcc gcc gcc gcc tca gcc gcc gcc gcc ccc aat aat     192
Ser Ser Ala Ser Ala Ala Ala Ala Ser Ala Ala Ala Ala Pro Asn Asn
     50                  55                  60 ggc cag aat aaa agt ttg gcg gcg gcg gcg ccc aat ggc aac agc agc     240
Gly Gln Asn Lys Ser Leu Ala Ala Ala Ala Pro Asn Gly Asn Ser Ser
 65                  70                  75                  80 agc aac tcc tgg gag gaa ggc agc tcg ggc tcg tcc agc gac gag gag     288
Ser Asn Ser Trp Glu Glu Gly Ser Ser Gly Ser Ser Ser Asp Glu Glu
                 85                  90                  95 cac ggt ggc ggt ggc atg agg gtc gga ccc cag tac cag gcg gtg gtg     336
His Gly Gly Gly Gly Met Arg Val Gly Pro Gln Tyr Gln Ala Val Val
            100                 105                 110 ccc gac ttc gac ccc gcc aaa ctg gca aga cgc agt caa gaa cgg gac     384
Pro Asp Phe Asp Pro Ala Lys Leu Ala Arg Arg Ser Gln Glu Arg Asp
        115                 120                 125 aat ctt ggc atg ttg gtc tgg tca ccc aat caa aat ctg tca gaa gca     432
Asn Leu Gly Met Leu Val Trp Ser Pro Asn Gln Asn Leu Ser Glu Ala
    130                 135                 140
```

-continued

| | |
|---|---|
| aag ttg gat gaa tac att gcc att gcc aaa gaa aag cat ggg tac aac<br>Lys Leu Asp Glu Tyr Ile Ala Ile Ala Lys Glu Lys His Gly Tyr Asn<br>145                    150                    155                    160 | 480 |
| atg gaa cag gct ctt ggg atg ctc ttc tgg cat aaa cat aat atc gaa<br>Met Glu Gln Ala Leu Gly Met Leu Phe Trp His Lys His Asn Ile Glu<br>                  165                    170                    175 | 528 |
| aag tca ttg gct gat ttg ccc aac ttt acc cct ttc cca gat gag tgg<br>Lys Ser Leu Ala Asp Leu Pro Asn Phe Thr Pro Phe Pro Asp Glu Trp<br>180                    185                    190 | 576 |
| act gtg gaa gat aaa gtc tta ttt gag caa gcc ttt agt ttt cat ggg<br>Thr Val Glu Asp Lys Val Leu Phe Glu Gln Ala Phe Ser Phe His Gly<br>                  195                    200                    205 | 624 |
| aaa act ttt cat aga atc caa caa atg ctt cca gat aaa tct ata gca<br>Lys Thr Phe His Arg Ile Gln Gln Met Leu Pro Asp Lys Ser Ile Ala<br>210                    215                    220 | 672 |
| agt ctg gtg aaa ttt tac tat tct tgg aag aag acg agg act aaa act<br>Ser Leu Val Lys Phe Tyr Tyr Ser Trp Lys Lys Thr Arg Thr Lys Thr<br>225                    230                    235                    240 | 720 |
| agt gtg atg gat cgc cat gcc cgg aaa caa aaa cgg gag cgg gag gag<br>Ser Val Met Asp Arg His Ala Arg Lys Gln Lys Arg Glu Arg Glu Glu<br>                  245                    250                    255 | 768 |
| agc gag gat gaa ctg gaa gag gca aat gga aac aat ccc att gac att<br>Ser Glu Asp Glu Leu Glu Glu Ala Asn Gly Asn Asn Pro Ile Asp Ile<br>260                    265                    270 | 816 |
| gag gtt gat caa aac aag gaa agc aaa aag gag gtt ccc cct act gag<br>Glu Val Asp Gln Asn Lys Glu Ser Lys Lys Glu Val Pro Pro Thr Glu<br>275                    280                    285 | 864 |
| aca gtt cct cag gtc aaa aaa gaa aaa cat agc aca caa gct aaa aat<br>Thr Val Pro Gln Val Lys Lys Glu Lys His Ser Thr Gln Ala Lys Asn<br>290                    295                    300 | 912 |
| aga gca aaa agg aaa cct cca aaa gga atg ttt ctt tct caa gaa gat<br>Arg Ala Lys Arg Lys Pro Pro Lys Gly Met Phe Leu Ser Gln Glu Asp<br>305                    310                    315                    320 | 960 |
| gtg gag gct gtt tct gcc aat gcc act gct gct acc acg gtg ctg aga<br>Val Glu Ala Val Ser Ala Asn Ala Thr Ala Ala Thr Thr Val Leu Arg<br>                  325                    330                    335 | 1008 |
| caa cta gac atg gaa ttg gtt tca gtc aaa cga cag atc cag aat att<br>Gln Leu Asp Met Glu Leu Val Ser Val Lys Arg Gln Ile Gln Asn Ile<br>                  340                    345                    350 | 1056 |
| aaa cag aca aac agt gct ctc aaa gaa aaa ctt gat ggt gga ata gaa<br>Lys Gln Thr Asn Ser Ala Leu Lys Glu Lys Leu Asp Gly Gly Ile Glu<br>                  355                    360                    365 | 1104 |
| cca tat cga ctt cca gag gtc att cag aaa tgt aat gca cgt tgg act<br>Pro Tyr Arg Leu Pro Glu Val Ile Gln Lys Cys Asn Ala Arg Trp Thr<br>370                    375                    380 | 1152 |
| aca gaa gag cag ctt ctc gcc gta caa gcc atc agg aaa tat ggc cga<br>Thr Glu Glu Gln Leu Leu Ala Val Gln Ala Ile Arg Lys Tyr Gly Arg<br>385                    390                    395                    400 | 1200 |
| gat ttt cag gca atc tca gac gtg att ggg aac aaa tca gtg gta caa<br>Asp Phe Gln Ala Ile Ser Asp Val Ile Gly Asn Lys Ser Val Val Gln<br>                  405                    410                    415 | 1248 |
| gtg aaa aac ttt ttt gta aat tat cga cgc cgc ttc aac ata gat gaa<br>Val Lys Asn Phe Phe Val Asn Tyr Arg Arg Arg Phe Asn Ile Asp Glu<br>420                    425                    430 | 1296 |
| gtt tta caa gaa tgg gag gca gaa cat ggt aaa gaa gag acc aat ggg<br>Val Leu Gln Glu Trp Glu Ala Glu His Gly Lys Glu Glu Thr Asn Gly<br>                  435                    440                    445 | 1344 |
| ccc agt aac cag aag cct gtg aag tcc cca gat aat tcc att aag atg<br>Pro Ser Asn Gln Lys Pro Val Lys Ser Pro Asp Asn Ser Ile Lys Met | 1392 |

-continued

```
                450                 455                 460
ccc gaa gag gaa gac gag gct cct gtt ctg gat gtc aga tat gca tct     1440
Pro Glu Glu Glu Asp Glu Ala Pro Val Leu Asp Val Arg Tyr Ala Ser
465                 470                 475                 480 gcc tcc tga                                                         1449
Ala Ser <210> SEQ ID NO 4
<211> LENGTH: 23
<212> TYPE: DNA
<213> ORGANISM: Artificial Sequence
<220> FEATURE:
<223> OTHER INFORMATION: PCR Primer

<400> SEQUENCE: 4
acaatcccat tgacattgag gtt                                           23

<210> SEQ ID NO 5
<211> LENGTH: 26
<212> TYPE: DNA
<213> ORGANISM: Artificial Sequence
<220> FEATURE:
<223> OTHER INFORMATION: PCR Primer

<400> SEQUENCE: 5
tttgctctat ttttagcttg tgtgct                                        26

<210> SEQ ID NO 6
<211> LENGTH: 30
<212> TYPE: DNA
<213> ORGANISM: Artificial Sequence
<220> FEATURE:
<223> OTHER INFORMATION: PCR Probe

<400> SEQUENCE: 6
aaggaggttc cccctactga gacagttcct                                    30

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                               20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
```

-continued

| caagcttccc gttctcagcc | 20 |

<210> SEQ ID NO 10
<211> LENGTH: 5241
<212> TYPE: DNA
<213> ORGANISM: Homo sapiens
<220> FEATURE:

<400> SEQUENCE: 10

| ggcagctcgg gctcgtccag cgacgaggag cacggtggcg gtggcatgag ggtcggaccc | 60 |
| cagtaccagg cggtggtgcc cgacttcgac cccgccaaac tggcaagacg cagtcaagaa | 120 |
| cgggacaatc ttggcatgtt ggtctggtca cccaatcaaa atctgtcaga agcaaagttg | 180 |
| gatgaataca ttgccattgc caagaaaag catgggtaca acatggaaca ggctcttggg | 240 |
| atgctcttct ggcataaaca taatatcgaa aagtcattgg ctgatttgcc caactttacc | 300 |
| cctttcccag atgagtggac tgtggaagat aaagtcttat ttgagcaagc ctttagtttt | 360 |
| catgggaaaa cttttcatag aatccaacaa atgcttccag ataaatctat agcaagtctg | 420 |
| gtgaaatttt actattcttg gaagaagacg aggactaaaa ctagtgtgat ggatcgccat | 480 |
| gcccggaaac aaaacgggga gcgggaggag agcgaggatg aactggaaga ggcaaatgga | 540 |
| aacaatccca ttgacattga ggttgatcaa acaaggaaa gcaaaaagga ggttccccct | 600 |
| actgagacag ttcctcaggt caaaaaagaa aaacatagca cacaagctaa aaatagagca | 660 |
| aaaaggaaac ctccaaaagg aatgtttctt tctcaagaag atgtggaggc tgtttctgcc | 720 |
| aatgccactg ctgctaccac ggtgctgaga caactagaca tggaattggt ttcagtcaaa | 780 |
| cgacagatcc agaatattaa acagacaaac agtgctctca agaaaaact tgatggtgga | 840 |
| atagaaccat atcgacttcc agaggtcatt cagaaatgta atgcacgttg gactacagaa | 900 |
| gagcagcttc tcgccgtaca agccatcagg aaatatggcc gagattttca ggcaatctca | 960 |
| gacgtgattg ggaacaaatc agtggtacaa gtgaaaaact tttttgtaaa ttatcgacgc | 1020 |
| cgcttcaaca tagatgaagt tttacaagaa tgggaggcag aacatggtaa agaagagacc | 1080 |
| aatgggccca gtaaccagaa gcctgtgaag tccccagata attccattaa gatgcccgaa | 1140 |
| gaggaagacg aggctcctgt tctggatgtc agatatgcat ctgcctcctg agaaactggt | 1200 |
| ggctttgaac acttggtgtg gactactgtg ttatccggga tatcaggtat tatgagacat | 1260 |
| cacctagcca tctgcatcac atctctctgg acaagcagct attaccaaaa aaggcatata | 1320 |
| cttccagtcc tgtgctccat ctgccttaat tctttgctcg ttcctccatg ttggcgccac | 1380 |
| ttcccagaga gctccactgc atctcacact ctgcccacgt gctggggaag tctcacggcc | 1440 |
| tgcacatctc ttgtgactct gggaaccgcc tctcccgccg gagcccccga gccccaccaa | 1500 |
| tggcagctct tcccagtcag cagcttcaga gcaggcagtc tccttggaag gcccgactct | 1560 |
| gttcctgcat ggcctgcagt ttctactttg tgcatagagt catttcaga gtcaccgcga | 1620 |
| ccctgttggc cttctagaaa gtttcttttg ttcttttctg agacaaccac ctaagtgata | 1680 |
| atacgctttt ttggaaacta atatatattg ccagactgca tcataacctt tatcatgcca | 1740 |
| agcatcctga tgcaactcac atttccctaa acatgggta cagttatgat ttataaattg | 1800 |
| agttggctta aatctccctc ttctcccttc ccaagtgtta caaagatcat ttactgcaac | 1860 |
| tgtcgttgga cactgtagct taaagggaac gtggacctca atgctttctg ccttcaactt | 1920 |
| ttcagcattg tgaccccagg gtggttgcca cccatctttt cctgaccccc cccaccccc | 1980 |
| ccacctccaa gaggttcggc ccacatcact gtacctggtg cttgtaaatt tggaattggt | 2040 |

```
gccttctcct tttggcaacc atggttatca atccttttc tgttttagtg tcttatttct    2100
tctttcaagt tatttgctag ccaaagatga catcactgag attaggagac aggggagagc    2160
ttgctgcaga ttctgacagt gcagatttta aatgtcagga tattagaata gctggcgctg    2220
gtttatgaaa gctgcgcgtt gttccgcgtt ctctcggtgt gcctggcctt ttatgtggca    2280
ctctgtatgt cagtttgtgt ccttcatgtg ctgatgtgat tacacaaaca ccatgcactc    2340
tcttttcata tcagagtaca ggacagagaa gtgatcaatg tattggtcta gtgagactga    2400
gatgaaaaga aataacctac agagtggtct gtaatgcctt ttggttggac tgggaacaag    2460
taaaaatttc taataaacat tttgagactt ccagaatcac ttttgttatc ttatcagacc    2520
atgggcctgc tgagggttga gcagacagcc tgcattctaa catccctgt tcccacccca    2580
cggccattca gactgcactc aatacgctga agtcgctttt gttgttgttg ttgttgtttg    2640
catcatttgg atttttttcc tgctttcaat accaaaaaaa tgcagatgct ttaaggccta    2700
aacagaattc tgaagaattt aaaatatgca attaaagttt gatatgtttt gtctcccaag    2760
caccttgttt tttgttgttg ttgttgttgt tgaagtcagc tgattttctc tttagaaaga    2820
gggtcagcta gaaacctagg ttttttggaa ttgtaaattt ttttttagta tagtctggag    2880
agaaaggtca ttcaaaagga aagtacaatg ggacttgctg cccttcatca tctcgttccc    2940
gtgccaggtg tgtgttggtc acgtaaaagc ctgggaagca tcagaggagt cccggattgc    3000
tgctgctacc tggagacagg gttagcaaaa taacactagt gatgagggag aggcttcttt    3060
tcaccataag cctgctgtgt acaccgaggg cggcaggaga agcatgggaa ggagtcagcc    3120
taagtttgca cattgcataa agggtacact aaggtatgag ctgaagcttt aggttctccg    3180
tgcttccctc aagacctcct tcttgctaac agaagcagta ggcaattgct gcagtgcgtt    3240
tctcaccctg ccaataggtc tgtctgtatc tctgttaagg aaaatagcct ggtccctcct    3300
ggcagtgctt ggaagcttga tgctaatttt tatatagcgt ggcaaactga ccagcagtgc    3360
caggccttga tctgtattct gcactatccc tttacttggt tcctggcact gaatggtctc    3420
cagccctgaa gaatcacgtg tgatcacagc agctgacctg gctttctcc ccgagaggaa    3480
ggggcatgtc attttatttt gacagaggga aaatgggagc tgtccttgac tgcctttgtt    3540
gtgctttccc gcgtaagata gcactgtgtt ttaaactgtt gcattacact gtctttgcaa    3600
tgatgtaaat gtaagaaatc acttagcttt aaaagcgcag tggtttgatc ttatttatat    3660
gaagactttt taacatatca agaattaggt gcattggcag gtagggtttg ggtgtgata     3720
actgcttcag atggaatgtt cacttaagct ttgtcttctt aaaaattatc aatgtgaatg    3780
tcataattat atatatttt gtggaaaatt ttctcctaag tataagttat tgtgcaaaat     3840
atagtgtcat tgatgcaaat aatagtttaa cttttagttt agaactccta aaagatataa    3900
attgtattgc atatgcatta aaagtttgtt ttatttaatt ttatgtgat gtgtgaagtg     3960
ttaggtaaaa ttttttttcac ttatccattt aaacaccttg ttacttgaat attgtgttga   4020
ctggtctgca acagtgatcc attctgtaat atagctcttt taactgggaa ggaaccacac    4080
cccagttgtg ccgattacat tagtgttggc acacagtcgg gtgctagtgt aacacaaatg    4140
ccgcgttgtc tgggtgtaca gtgtttgtgg agacgccact tcctcaaaat ggttttgat     4200
tgttttaac ctataagacg ttctgatgct cacaaacctc tattcaacac acaaaacaaa    4260
catgaaaagg tagttagttg ggttgtaaca gcttactggg gtggactcat aaaacagtgg    4320
cttttctgttc atctaaagtt tcctcagata ccacagacca ctgttaagtg tgctcattgt    4380
cactttaaat ttcaacgata ccctattttt gtcattctaa atatcagatg tactattggt    4440
```

-continued

```
ataattgcac accaaaaata agccaaacag tgcattacgc taactggatc cctgctttta      4500
tgtgagctaa ggaaagatgg agccaactcc aacgagggcc tcttttttctc tcttgtctag    4560 cctgtttcta aaccgaatga tccaggattc aagcttctat tgtcaagtga aactttcctc     4620
agatggactc caggtagcca ggtcacctaa acctagtggt cctgtgcgat gctctttctg     4680
ccagtccctg aatctctgca gcttctctta cctgtcttac ctgtagtaaa gcacaattgc     4740
agtggcgtcg cattcagaag aagggaaggt cagcagaggc tatgcatgtt gtgtgatgat     4800
gagtgtttac agccaccttc tcctaaaacg aaatttatac cggggtggat agtattccat     4860
taggtagact tatcgacttt gctaagtgct ttttagacag cttaaaaaat tttcaagatt     4920
ttaaaagatg tataaggtta agtttgcaaa tataatggaa atgctgtata tcttttgaag     4980
tgatgaaatc cacgttggaa ttttaaagaa aatatgttgt aataatgctg ttgtaagtaa     5040
tattttaatg tctctttgcc tgttttctat ttcagcacat tcattgtggt gaatgttcat     5100
agcattataa ctgcttagcc attgaatgat aacatttgtt agtggaaatt ggaaaattta     5160
tttgtgaaat tctgcagaat tcattttttct atttccaata tttgctgagg ggttaaataa    5220
aaattttcaa gccattgatg t                                               5241
```

<210> SEQ ID NO 11
<211> LENGTH: 139257
<212> TYPE: DNA
<213> ORGANISM: Homo sapiens
<220> FEATURE:
<221> NAME/KEY: unsure
<222> LOCATION: 10445
<223> OTHER INFORMATION: unknown
<221> NAME/KEY: unsure
<222> LOCATION: 23754
<223> OTHER INFORMATION: unknown

<400> SEQUENCE: 11

```
caagggcagg ggccgcggcc aagggtaggg ggcggggagg gcggcgaact cctcgccgct      60
gcctggagag atggatcatg gggcgtaggg agatggcaaa cctcaaacca cgtacgcgcgg    120 gcgatacgcg tcaaccgaac ctcgccaacg gaagcccgga gccgcccctc cccgctcccc     180
cgccccgccg ccccggacgg acgggcgcgc ggagccaacc ctcgctgccg ctggctgtcc     240
aaatcccacc agagccaatg ggagcgcgag gggggcggga gccgtctcgc gtcagttggg     300
tgcgcgcccc cctcccccgg cgcccctgca ggccccgccc ctgcctcctc ccctctccgc     360
tcgctgctcc cggagtagtt ggtgccagtg aagtgagggc ggcgatgaga gcgaaagttg     420
cgctcggctc gtcgctgggg gcttgaagcg gctccgcgct ctgcccgttt gggcctcccc     480
cgactcggac tcgcgcccgt gggctcccgc gcgcccgcc cggccccgcg ccggccccgc      540 gcccctccc ccgtctcggc gcccctcct caggagccgc gggtcccgc cactttcgca       600 cggccccggc ccccgccgat gccggccatg gtggagaagg ccccgaggt ctcagggaag     660 cggagaggga ggaacaacgc ggccgcctcc gcctccgccg ccgccgcctc gccgccgcc     720 tcggccgcct gcgcctcgcc agccgccact ccgcctcgg gcgccgccgc ctcctcagcc     780
tcggccgccg ccgcctcagc cgccgccgcc cccaataatg ccagaataa aagtttggcg     840 gcggcggcgc ccaatggcaa cagcagcagc aactcctggg aggaaggcag ctcgggctcg     900
tccagcgacg aggagcacgg taggtggcag ccgccccgc ggccccgggc ccgcgcccc      960 gcgccgcgct gaccgccgta ttctgcttcc cccgcaggtg gcggtggcat gagggtcgga     1020
ccccagtacc aggcggtggt gccgacttc gaccccggtg agtagcggcc ccggccggcc      1080
```

```
ggcggcgggg atgagcggga gccccgggtc cccggcgagc ccgagggggc gggagcccgc    1140
cgacaacttt cttttttgtgc gttcgccctg ccgtccgtgg ggagaacagc agggcgagga    1200
cgaggaggcg cacacgcaca cgagtgttct gcaaacgtgc ctctgcaccc gggggaggcc    1260
aggtcgcccc cagcagggcc ggcgccgctg ccccccttgcg cctccgagga ctgcgggtgg    1320
cgtcggaggt ggccacacct ggcctggggg cgctgggggt ccctgcgtcc aggtgagctg    1380
cgcctcggcc aggggtaagg gtggcagtgc cggagagtta gtgtcctgcg agcgccccgg    1440
acttaggagg tccccagaga ccccttttctc ggaaccccttc ccaaaggctg ctccccacgc    1500
ctttgctcct cctctcagcc tctgggctct tgctggctcc tgactgccct cccatccaga    1560
aggcgagtag aagaacgacc ccccaaaacc agtcaataaa agaagtgtgt tttccagagg    1620
gcgcctgcct ggggaagaga gtctcgcgtg tggcagttgg attttaggac ctatttgtaa    1680
atgtgtgtat ttccttttttt ttggaggaag agattgtgaa attgagaagc atcagaagct    1740
ttagcctaac aaatgctttt cacctacaag aaagccctac accctagaat ggaacactta    1800
gttccctggc tgctattctg tgtagaagca aatttaaagt ggtacaagaa aaaaaatccg    1860
atcagacaaa ggaattcgtc agattttaat gcatgagatt ctagccagtg tctgtatgag    1920
actgtcttta aaggttgttg gtatggaaaa tgtttgaaag aacgtaggat ttatttcaga    1980
aataaaattc aaaagagcat cttgtaaagc tggagttaac aatcctccat ggttggaggg    2040
ctttagagct gggggttctgt atgtgggtta ccactagt ttatttgaaa agataaacgc    2100
atacatgttt tttccttgga aacaagactg cagaaaattg caatgatcta gtccttgaaa    2160
aaggcgattg ctctcaagct gttattaagg tactaaactg cactttgaag tgaaaatcaa    2220
tagaggtcct aggtgagctc ttggacactc tggaaataaa tgacttccta aattggcctt    2280
ctaaattttg atttgttgac gtaaatctgt taaatttatt tgtctaatac tcgcgtttgt    2340
gtttctttta agtccatgtt agtgtttttg atagtttcct cttctcccca attctttttt    2400 tttttttttgg tagtcacttc tcgtttatga gtgacaggat agaactaggt ggccaggcta    2460
tatctcttgt atgcttggct cctccgttcc ttggttggcc accaggggaa gcatactgtt    2520
ttttggttac agttgaccct gtcttcattt tgtaggtcaa gtctatcttt gctttaaaac    2580
acagaacata aagcttgtta ccaaattttc ctaatgtatt attttttaaaa atcgacttcc    2640 acaaatcttt gagtaagttg gtaggctttt tgatacattt ttgttaacat aaattttgaa    2700
aactttatgt agatgtgttg gatgtgacta aggaaaaggg catatttgtc aacaacagga    2760
attagatttc tgacattcat cgaaatattg acatcagctc tgcattgtta gtaatgagtt    2820
tgacttcttt ggagtatac ttttctttga aacagcaaat ataatatttt gaactgtctt    2880
tgggcttttt gttggaatag atatgagcat aaacttgcta gtgaccagct attctaaaat    2940
ggaaaacatt tatcagattg cagtagctca ccctgtagt cccaacactt ggggaggcca    3000
aggctggagg atctctggag ctcaggagtt ggagaccagc ctgggcaatg tagtcagact    3060
ctgtctcaac aaaaaataaa aaattagct gggcatggtg gcatgtgcct gtagtttcag    3120 ctacggggg gtctgaggct ggaggatctc tgggaagtca aggctgcagt gagcagtgat    3180
ctggccattg cactccagcc tgggtgacag agtgagaccc tgtctcagaa ataaaaagga    3240
aaacatctaa ctgttttgct gcatagtctt gctgccaatt ggttgagtat tgatattaaa    3300
atttccaaat ttcttttttt ttttttttgag acggagtctt gctctgtccc tcaggctgga    3360
gtgcgcagtg gtgtgatctc agctcactgc aagctccgcc tcccaggttc acgccattct    3420
```

```
cctgcctcag cctccagagt agcagggact acaggcgccc accaacactc ctggctaatt    3480
ttttgtattt ttagtggaga cggggtttca ccgtgtcagc caggatggtc ttgatctcct    3540
gacctcgtga tccgcccgtc tcggcctctc atagtgctgg gattacaggc atgtgccacc    3600
gcgcccggcc ccaaatttct ttattttgtg tttgttttaa tctggaaagg aatctaactg    3660
gtgtaaagta atttcaaacc ttgttttgcc aacctaagca gggggacaca gttttctaga    3720
tatggcagaa aattgagact ttactatttc ctagtggttt tttatgtgtc ttttcattta    3780
acttaaaagc ttaaggggaa ggaaggcttc cattttggaa tagaaatgat acaacatttt    3840
tttttttttt aatacggagt ttcactcttg ttgcccacgc tggagtgcaa tggcgtgatc    3900
tgggctcacc gcaacctctg cctcctgggt tcaagcaatt ttcctgcctc atcctcctaa    3960
gtagctggga ttacaggcat gcgccaccat gcctggctaa ttttttgtat ttatagtaga    4020
gacagggttt ctccatgttg atcaggctgg tctggaactc ctgaacgcag gtgatccacc    4080
cacctcagcc ttcaaaatta ctgggattac agggtgagc caccgtgccc agccaactga    4140
tgtttgtttt atagcaaaat tcttcttag ctgtttaaga cttaagacag gttctttcca    4200
tgactgcaat ttaagagtag tgaattgagt aataaattaa gaattgagag tttgatcctt    4260
actagttttt atttcctcct cctacttgtt tttttctttt ttcttttatt ttttgagacc    4320
aagtctcact ctgttgccca ggctggagtg cagtggcacg atcttggctc actgcaacct    4380
ccacctccga ggttcaagtg attctcctgc ctcagcctcc agagtagctg ggattacagg    4440 tgccaccac cacgcccaac taattttttgt gttttattta gagatgcggt ttcaccatgt    4500
tggccaggct ggtctcgaac tctttgcttc aggtgatctc cccgccttgt ccttccaaag    4560
tgctgggatt acaggcgtga accactgtga ctgcccctcc ccccgccttt ttttttttt    4620 ttgagacgga gtcttgatct gttgcccagg ctggagtgca atggcacaat cttgactcac    4680
tgcaacctcc atctcccagg ttcaagtgat tctcctgcct cagcctccca gtagttgga    4740 actacaggtg cgtgccacca tgcctggcta attttttgtgt tttagtaga cacggggttt    4800 caccatattg gccaggctgg tcttgaactc ctgacctcag gtgatctgcc ccctcgggcc    4860
tcccaaagtg ctgggattac aggcgtgagc caccatgccc tgtccctacc tcagttttga    4920
gtgtgtcttt gttcttctct tttactagaa tttgaacaga gaggtggacg tgaaacttaa    4980
caggcagctt ttttctttt ctttttttat tatagtaaaa taagtaacta tggtagagat    5040
gcatgaatgg aggaatttga ctttgatttt tttttttga gacagagtct cgctctttca    5100
cccaggctgg agtgcagtgg catgatctca gctcactgca acctccatct cctgggttca    5160
agcgatcctc ctgctgcagc ctcctgagta gctgggatta cagacgcaca ccaccacacc    5220
cggctagttt ttgtagtttt agtagagatg aggtttcacc ttgttggcca ggctggtctc    5280
gaactcctga cctcaggtga tccacccacc ttggcttccc aaagtgctgg gatttcaggc    5340
gtgagccact gcgcccgacc ttttttttt ttttttttt tttttgaaa tggagtcttt    5400 ctatgttgcc caggctggag tgcagtggca caatcagctc acacagcctc tgcctcccgg    5460
gttcaagcag ttctcctgcc tcagcctcct cagtagccgg gattacaggc gtgtgccact    5520
atgtctggct aattttggta tttttgcaat tttttttttt tttgagatgg agttttttc    5580 tcttgttgct caggctgggg tgcaatggca tgatctcgat ctcggctcac ctcaacctcc    5640
acctctcagg ttcaagcaat tctcctgcct cagcctcccg agtagccggg attacaggca    5700
tgggccacca cacccagcta attttgtatt tttagtaggg atagggtttc tccatgttgg    5760
tcaggctggt cgtgaactcc caacctcagg tgatttgcct gccttggcct cccagagtgc    5820
```

-continued

```
tgggattata ggcgtgagcc actgcgcagc cctaattttg gtattttgg tagagatggg    5880
tttcaccatg ttggccaggc tggtctcgaa ctcctgacct caggtgatcc actcacctcg    5940
gcctcccaaa gtgttgggat tacaggtgtg agccactgtg cccggcctga ttttttgtc     6000
agattttact tatttgcggt atgccagctt gaccctattt aggtttgaaa gcaaatggtt    6060
ggagctaaga ctatctgata tttcctatgc agttcaaagg aagatttaat tctgtcatgc    6120
cttacaaaga gtgaatgagg tggatagagc acgttagtct taaaatcctg attcagttct    6180
tttttttttt tttttttgag acggtgtctc gctctgttgt ccaggctgga gtgcagtggt    6240
gtaatccggg ctcactgcaa gctccgcatc ctgggttcat gccgttctcc tgcctcagcc    6300
tcccgagtag ctgggactac aggcgcctgc caccacgccc ggctaatttt tttgtatttt    6360
aagtagagac ggggttccac catgttagcc aggatggtct caatctcctg acctcgtgat    6420
ccgcccgcct cggcctccca gagtgctggg attacaggcg tgagccgcca cgcctggccc    6480
tgattcagtt cttataaaat aattaatacc tagattagat cggtgtagtg tggcattgct    6540
tggtagttag ataccatttt gtgtttacac tgaaataaaa agttttacca acttttaaag    6600
agttaaaaaa aaaagagtt aaaaacctaa gtgcagccct acactttaa cttaggcttt      6660
gttcttacat gtgttgtcca gactgccttt ccatgctgtc tgccgcagat tatgctgagt    6720
tgtcattggt ttcttttaat attcagtagt tacagaataa tagggtaaga gggggatgc     6780
ttatctatcc tacctctggt tggttctttc ctacataagc aaagcatcac ttattttgaa    6840
atgaataatg tttttctttc cttttttttc ctttttttt tgagataggg tcacactctg     6900
tcaccagtat agtggtgtga tcatggcggc agtgaacttg aacctcctgg gcgcacacta    6960
tcctcccatc catactttac ctcgaaagta gctgggacta cagatgtcca cgaccatgcc    7020
tgactagttt ttttgtattt tttgtagaga caagagtttt gccacgtagt ccaggctggt    7080
ctcgaactcc ttggctcaag ccatctgcct gccttggcct cccaaagtgc tgggcttaca    7140
ggtgtgagcc accgtgttca gccattatta ttactatttt ttaattttt ttattctctt     7200
tatacacgtc cttggtgctt cagaggcgta cattgttaat gatgaatatt tttgagatag    7260
tggcccttta aaaagcaac ctttattttg aatgtttaat ccaatgtatt taatcagatc     7320
tgaaaattg tggttgtcat tggcttaact gtcacttcag agttgacttc tgtcagaaaa     7380
ctgtgttatg ttttcatgtg aataggtaa tttactgaa cagggtgtct tgatatgcct      7440
ttcatttgtt ttcactggtg attctatgtt ctgctttttt tatgctttag atcattgtaa    7500
aaaaaatatg gtgaatgctt tgtggttttg ttttgttttg ttttttttt ttgaaacaag     7560
gtcttgctct gtcacacagg ctagagtgca gtggccctga tgttggctca cttcaacctc    7620
tgcctcccag actcaagtga tcctcccccc tcagcctcat cagttgctgg gaatacatgt    7680
gcacatcacc acgcttgagc ccaggctggt ctctaactct tgtgctcaag cagtcttcct    7740
gccttggcct cccaaagtgc tgggatcaca ggcatgtgcc tggcaatgct ttgtgattta    7800
tttatttaat tattattatt atttttttga gacggagtct cgctctgtca cccaggctgg    7860
ggtgctggag tgcagtggcg cgatctcagc tcactacaag ctccgcctcc cgggttcacg    7920
cccttctcct gcctcagcct ctctgagtag ctgggattac aggcgcccac caccacgccc    7980
ggctaatttt ttatatttt agtagagatg gggtttcacc gtggtcttga tctcctgacc     8040
tcgtgatccg cccacctcgg cctcccaaag tgctgggatt acaagcgtga gccaccgcgc    8100
ccagccagtg attgattgat tgattttagt tttatttttt attgtatttt gagacagagt    8160
```

```
tttgctcttg tcacccaggc tggagagcaa tggtgtgacc ttggctcact gcaacctctg   8220
tctcccaggt tcaagtgctt ctcctgcctc agcctcccga gtagctagga ctacaggtgt   8280
gtgccaccat gcccagctaa ttttttttt ttttttttg aagacggagt ctcactctgt     8340
tccccaggct ggagtgcagt ggcgtgatct cagctcactg caagttccgc ctcctgggtt   8400
cacgccattc tcctgcctca gcctcccgag tagctgggac tacaggtgcc cgccaacacg   8460
cctggctaat ttttgtatt tttagtagag atggggtttc accatgttag ccaggatggt    8520
ctcgatctcc tgacctcgtg atctgcccgt cttggcctcc caaagtgctg ggattacagg   8580
cgtgagccac cgcgcccggc tgctaattt tgtattctta gtagagatgg tatttcgctg    8640
gctgggcatg gtggctcaca cctgtaatcc cagcactttg ggaggccgag gcaggcggat   8700
cacttgaggt cgggagttca agaccaacct ggccaacatg atgaaacccc tctctactaa   8760
aaacacaaaa attagctggg cgtggtggtg catgcctgta atcccagcta ctcagaaggc   8820
tgaggcagga gaattgcttg aacccaggct gcaaaggttg cagtgagcgt agatggcacc   8880
actgcactcc agcctaggtg acaaagtgag actctgtctc aaaaaaaaaa gacggggttt   8940
cactatggtg gccaggctgg tttcgaactc ttgacctcag gtgattgacc cgccttggcc   9000
tcccaaagtg ctgggattac aggcttgagc caccgcaccc gaccaaacac tgatttaata   9060
ctaggcaata tttgcttcag gtacagctaa agcctcattc ccgccttctt tcttcattaa   9120
ttcacagttg gtttatatta tttctgtgat agtttgcatc ttctgagaag cagatgacaa   9180
gacagaatta gatgtgcaag aggttcatta gggtatgctt gtgaaggata aagagaggaa   9240
ggaggtgtag gtggcaagag cctttacact ggaagcatgt gtgacacctg tgaaagaaga   9300
gagggaagga atgatgatta atgattgata gaggaacctc aaactgcagt gcagcttgca   9360
gttcagagaa aatctcagcc agagtagatt gttagaagag tctgttgggc aggaatggtc   9420
cttctttgtg aacatctgct gtgttcagtc attggctggg agcagcctag agtagcctag   9480
ccttggtatg ggtgctgtag tagatttctg gtagctgggg ctgtcagtta actacactcc   9540
ttgcaacatt ttctctcttg aagggaaatc tgagtggcac actcaaggct gtcagaattc   9600
ccatacgtgt ttttgtactt aaatacatgt gtgtaattcc agcactttgg gagggtgagg   9660
cgggaggatc acctgagatc aggagttcga gaccagcctg gccaacatgg cgaaaccccg   9720
tctctactaa aaatataaaa attagctggg tgtggtcgcg ggtacctgta atcccagcta   9780
cttgggaggc tgaggcggga gaattgcttg agcccgggag gcggagattg cagtgagccg   9840
aggttgtgcc actgcactcc agactggacg acagagctag actccgtctc aaaaaaaaaa   9900
aaaaagtgat aatatgtttt cttgttattg ttagtgtttt tgtaaatgga ataatctatg   9960
ctattcatgt acttttatgc tttccaaaca agtacatttc cactagcaag gtaaacaact   10020
ttgttttcac cttgtcttcg tcatggtgtt agttaggtta ttaatttttt ttaaatgcta   10080
tcctttaatg gcttatatta gcatttttt ctttctttt ctttctttt tttttttt       10140 ttttttggaga tggagtttcg ctcttgtttt gttcccagg ctagaaatgc agtgacgcag    10200
tctcctctca ctgtaacctc cgcctcccg gttcaagtga ttgtcctgcc tcagcctccc    10260
gtgtagctag gattacaggc atgtgctacc acgcctggct aattttaaaa atattttta    10320 gtagagaagg ggtttcacca tgctggccag gccggttttg aactcctgac ctcaagtgat   10380
ctcccgcatc ggcctcccaa agtcctagga ttacagacgt gatccactgt gcctggcctc   10440
ttctnctgtt ttgtagtact ttatatcgtc ttgcctctta tgctggagtg cagtggcatg   10500
atcacagcac actacagcct cagcctccag ggctcaagtg atcctcctgt ctcagtttcc   10560
```

-continued

```
tgagaagctg ggactacagg catgagccag tatgcctgac tgatttttga acttttttgta    10620
gagacggggt tttgccaagt tgcccagact ggtctccaac tcctgggctc aaccagtcct    10680
tctgctgtgt cctcccaaag tgttgagatt acaggcatga gtcactgtgc ctgtaattaa    10740
gttttccaat taatgatgag gttaagtgtc ttatgttttt aattttttaat ttttaatttt    10800
tttaagacct ttttttttccc ctttttttgag atgagttctt actcttgtcg cccaggctgg    10860
agtgcagtgg cgtgatcata gcgtactgta gccttgaact tctagggctc aagtgatctt    10920
catacctcag tttctggagt agtttggact acagttgttc accaccacac ccagcaaaga    10980
atgtgacaaa aagtactaag tgtgttttag ctaagtatcg ataagaaaag agtgtctttt    11040
tatttatttt ttatttgttt atatgtactt tttgagacag ggtctggctc tgtcatccag    11100
gctggagtgc agttgtgtaa ttttggctcc ctgcatcctc agcctctcag gctcaagtaa    11160
tcttcccacc ttggcctccg gagtagctgg gtttataggc tcttgccact atgcccagct    11220
aatatttgta tttttttgtag agatgggggtt tcaggttttg ttggtcttaa ccctggccca    11280
ggggtgtctg taaattttttt tttcttttttt ttgccactca gtttcctcct gtgaatgtat    11340
cttctttttg ctattttttct tttttttttccc ccttagggtc ttgctctgtt gcccaggctg    11400
gagtgcggtg gcttaatctc agctcactgc aaccttcatc tcctgggctc acatgatcct    11460
cccacctcag cttccgaggt agctgggact acaggagtgt gccaccacgc ctggctaatt    11520
tttgtgtttt tttgtagaga caggggttttca ccatgttttcc taggctgttt tgctgttttt    11580
ctataggggtg ttggttttta taggttttttgg ttttttttgtat ggatttgtgt gagttctttt    11640
tatttatata tttggatatt ctttgttaga attgcacata tgttttttgt tttttctttta    11700
atattatgtg tgttgcgggg aggaggattg agtttatttg actaggaagg gataaaaata    11760
cattcctgac tggagactgt actcagagat tggtcttggt gtataccccct gatttctaag    11820
atgaatgtta ctgagaattg acaattttttt ttgttgattg ttgtgtttcc actaagttat    11880
tcatctcatt ttggcctgct attagctagt tgacccaaat cacagtgctg gatgacttga    11940
aaagctctga tttaattttttt gcctagtata tagttatagt agcatatagg ttaaaggtta    12000
aagttacagc tttgatccta taatggtcag ttagtttccc acgaaaggtt aaaatgctat    12060
agactaaaac taacagctgt cttagggatt tgccactcct tataaggcaa tgggtagtgt    12120
gtggataggg aggtacaact tgtcatcact aacaaaaccc tcgaaagaat gatctatcca    12180
ggttgcttac tctgtgccag gctagtttta acacacatca aatcatttga ccctcacaac    12240
agtcatatga tgtaaagtta ctatctccat tttccagatg aggaaacaga ggcattgaga    12300
ggcttagtct tatggttgaa cctaataact tgccgtggta atccagtccg agaggccctc    12360
agctgtaaga ggcaccttta ttttatgttt cagtaagaaa ggaaaaggat caacaagata    12420
gactgttaat tttaagtatt ataagaattc tgatttataa gtataatcag aattcaattt    12480
agtgtatttt agagagggtc agccagaatc ctctttaaga gaaaacactt aggctgggtg    12540
cagttgctca ctcctgtaat cccagcactt tgggaggctg aggcaggtgg atctcccaag    12600
gtcaggaatt caagatcagc ctggccaaaa tggtgaaacc ctgtctctac taaaaataca    12660
aaaaattagc caggctataa tcccagcatt tgggaggct gaggcgcgag aattgcctga    12720
acctgggagg tggagctaca gtgagccgag atcgtgccac tgcactccag cctgggtgac    12780
agagcaatat ccatctcaa aaaaaaaaaa aaaaaaaaaa ggaaaagaaa aaacacttag    12840
gagcaagact ttattggatc cattgattag ttgttttccat gtggccccag gtgttgggga    12900
```

```
attttatgtt tcgggttgcc agagccaact tgtagtccag ttacattcct cttcttcctg   12960
gcagtgagaa caccggtgaa atgggaggtg gttagcttgg ttgcctgggg acaaattgga   13020
ctgagttgct ttattcctgc atgtatgttg aaatagtcat cttcacaact tagaatatag   13080
ttggagtttt ttttagaaga gccatttatt ttgatggtgt gactgaaggc tatacataca   13140
gtcatgtatt gcaaaacaaa tgtcattttg gtcaaggaca gtggtcccat aagattataa   13200
tggaactaaa aaatttctgt cgcctagtaa cttcaccttg tctatagtgc aacagcgtgt   13260
agcattactt aggtgtttgt gtggtgttgg tgtaaacaaa cctactgcac tgccagtctt   13320
acaaaatcta gcacatggag ttatgtatag tacatagtac ttggtaatga caataactgt   13380
attactggtt tgtggattta ctatgctata ctttgtatgg ttattttaga gtgtattcct   13440
acttataaaa attatcagtt tgctgtaaaa cagcctcagg caggtccttc aggaggtatt   13500
ccagaaggaa ggcattgtta ctctagaata tgacacctcc atgggtctta ttgcctctga   13560
agaccttcca gtgggacaag gaaggtatgg agttggaaga tggtgatatt gatgatcctg   13620
actgtaggct aggccaatgt gtgtgtattt gtggtttttt ttgttttttgt ttttgaaatg   13680 gagtatcgct ctgttgcaca ggctggagta cagtggcatg atctcggctc actgcaacct   13740
ctgcctccct gcctccagtg attatcctgc ctcagcctcg tgaatagctg ggattacagg   13800
tgcgcgccac catgcctggc taattttttgt attttttagta gaaatagggt ttcatcatat   13860
tgggcaggct ggccttgaac tcccgacctc aagtgatccg cctgcttcgg cctccgaaag   13920
tgctgggatt acaggcatga gccaccgtgc ccggcctaat ttttgtattt ttagtagaga   13980
cggggttttg ccatgtaggc caggctggtc ttgaactcct gaactcaggt gatttgcctg   14040
tcttggcctc ccacagtgct gggattacag gtgtgagcca ctgcacctga ctgtatttac   14100
acccatactc tccctgaagg ttgtagttcc tgccctgctt tacttttact ggcatagaag   14160
ctgctgggct tggtgttctg ctttcaaact tagcgtggat atagggagtt cagcggggag   14220
gaagagaaga gtaggtgctt tactagtttt gatcttactc agtaccagag agtgttctgg   14280
gagctagtgg tgtcatgtat gtctgaattc tttgagggtg gtagcgtagt tttttgaacc   14340
accaaatcag gttttaagtt tttttttttt ttttggaggg gagatagggt ctcaccctgt   14400
cccccaggct ggagtgcagt ggcgggaaca tggcccactg catgcagcct tgacttcttg   14460
ggcaccagtg atcctcctgc ctcagcctcc caggtagctg ggattacagg tgtgaggcac   14520
tgcacctggc tgttaagtat tatctagtat aaactcgtca gagctaaata ggggctgaat   14580
tttctaagaa tatgtgcttg gtttgggtct tttcttgaat aggcttttgt ttttgttttt   14640
ttgatttttt tgggttttgt gttagttttt tttttttttt ttgagacgaa gtctcactct   14700
gtcgcccagg ctggagtgca gtggtgtgat cttagctcac tgcagcctct gcctcccgga   14760
ttcaagtggt tctcctgcct cagcctccca gtagctggg attataggca tgctccacca   14820
cgtctggctg attttgtatt tttagtagag acggggtttt ccatgttgg tcaggctggt   14880 ctcgaacttc taaccttagg tgatccgtct gccttggcct cccaaagtgc tgggattata   14940
ggcgtgagcc accgcgcccg gctgagtagg cattttttaa tggacatttg ataaggacca   15000
agtgcaactg tatatcaaat ggaaatctag ggaaaaattg tcttttaaat tgcagttaaa   15060
agctgattat ccctattgtc tcttgctttc cttataatga atttgtataa attggagatg   15120
cacatcttgc atagatgtgt tttctttttt ttatataaag tggtgcaagt cacatcacaa   15180
aattgactat tttttggcca ggtgtggtga ctcatgcgtg taatcccagt gctttgggaa   15240
gctgaggcaa gtgggtcacc tgaggtcagg agtttgagac cagccaggcc aatatggtga   15300
```

-continued

```
aaacctgtct ctactaaaaa tagaaaaaag ctagccaggc gtggttgctc atgcctgtaa    15360
tcccagcact ttgagaggct gaggtgggca gatcacgagg tcaggagttt gagaccagcc    15420
tggccaacat ggtaaaaccc catatctact aaaagtataa aaattagccg ggtgtggtgg    15480
cacctgcctt taatcccagc tactcaggag gctgaggcag gagaatcgct tgaacccggg    15540
aggtggaggc tgcagtgagc tgagatcgtg ccactgcaca ctagcctggg caacagagcg    15600
agactctgtc tcaagaaaaa ccacaaagta caaaaaatta gccaggtgtg gcggtgcacg    15660
cctctaatcc cagctacttg ggaggctgag gcaggagaat tggttgaacc ggggaggcag    15720
aggttgccat cagccgagat cacgctactg cactcaagcc cgggcgaaac agagagactc    15780
catctcaaaa aaaaaaacaa caaaattaac cgttttacaa tgaacaattc agtggcattc    15840
agtgcactcg cattgttgtg gagccactgc ccttgtctag ttccgaaaca ttttcatcac    15900
cctaaaaaga aaatctcaca tgtgttagaa tgaagaatga gttacttctt attctccatt    15960
ctcagtacca ggcaaccact aacctgcttt ttgtttctgg attacttatt ctggaacttt    16020
cacgtaaatg ggtatgtgac cttcatgtct ggcttctatc acttagtgta atgttttcaa    16080
ggttcattca tgttgaagct tgagtcagta ttggtacttt ctgtgcttca ttgcttttgt    16140
tttgtgttgt tgttttttt gttttgcctt gttttgtttt tttgagatgg agtcttgctc    16200
tgtcgtccag gctgaagggc agtggcgtga tctcaactca ttgcaacctc tgcctccctc    16260
gttcaagcga ttctcctgcc tcagcctccc aagtagctgg gattataggt gcgcaccacc    16320
atgcctggct gattttgta tttttagtag aaatgggggtt tcaccatttt ggccaggctg    16380
gtcttgagct cccgacctca ggtgatacac ctgtctcggc ctcccaaagt gctgggatta    16440
caggtgcctg gcctaatttt aaatttttt ttttgtggag agacggggtt tgtttatgtt    16500
ggccaggctg gtctctaact cctgacctca agcactcctc ctgcctcagc ctcccaaaat    16560
gctgagctta taggcatgag ccactacacc tggctcattc atttgttgat ggacatttag    16620
cttgttgtta ccttttgatt attgtgaacc gtgctgttat gtacattcat gtacaggtat    16680
ttatctgttt tcatccttt aggggtatat atctattagt ggaattgctg ggttatggag    16740
taattctgtg cttcactttt tttttttt ttttttttt aaattttat tttgagacag    16800 gctcttgctc tgttgcccag gctggggtga cagtggtatg atctcagctc actgcaacct    16860
ctgcctcccg ggttcaagca attctcctgc ctcagcctcc tgagtagctg gggttacatg    16920
tgcatgccac tacacctggc taattttgt atttttagta gagatggaga acatgttgg    16980 ccaggctcgt cttgaactcc cgacctcagg tgatccgcct gcctcggcct ctcaaagtgc    17040
tgggattaca gatgtgagcc actgtgcctg gtctgtgctt aacttttga ggaaccatta    17100 aattgttttt cacagtagct taaccatttt atactccatg attaacgtat gagggtttca    17160
atattctact ttttatttc tgttttttga gatggagtct cactctgttg tccaggctgg    17220
agtgcattgg tgcgatctcg gctcactgca gtttccgcct tccaggttca agtgattctc    17280
ctgcctcagc ttcctgagaa gatgggattg taagcatgta ccaccaagtg tggctaattt    17340
tttttttgta ttttttagta gagacagggt ttcaccgtgt tggccaggct gatcaggctg    17400
gtcctgacct caggtgatct gcctgtctcg gcctcccaaa gtgctgggat tacaggcgtg    17460
aaaatgctac tgatgacagt gcagagagtc ctgagatgct tagagtagtg gagttactcg    17520
atccttccct gtggtggagg gttgggagtt gaagaaacca ggaagtccta tatgaaatgg    17580
tcctttaagg ccgggtgcag tggctcaccc ctgtaatccc agcactttgg gaggccgagg    17640
```

```
caggcagatc acgaggtcaa gagattgagc ccaccctgga caacatgaca acatggtgaa   17700
accctgtctc tactaaacat acaaaaatta gctgggagta gttccagcta ctcgggaggc   17760
tgaggcagga gaatcgcttg aaccctggag gtggaggttg cagtgagccg agattgcgcc   17820
attgcgctcc agcctgggca acaagagcga aactccatct caaaaaaaaa aaaagagaa    17880 atcgtccttt aagtcaagcc ttaaaacgta ggaattacct agttaatttg aatattaata   17940
ttatatgata tataagctgt acatgttata aaaattattt tgaaaagttt aatctttaaa   18000
attttagttt agattttcct tgtagttatc tagagctgtg ctgtccaata gtgtagccac   18060
tagctacata taactattga aatttaaatt aattaaaatt aaataaaatt aaaaattcag   18120
tccttctgtt acactaggca cattttagat attcagccat catatatagc tagtaggtgc   18180
catattggac agctcagaat agagtatttt tatcctccca gcaagttcag ttgggtggca   18240
atgatctaga cattttgatg aaatgaaagc ttcattatta ttgctattat tattattatt   18300
tttgtgtgtg tgtgacagag tgtcgctctg ttccccaggc tggagtgcag tggcgccatc   18360
tcagcttact gcaagctcgc ccacccgcgt tcacaccatt ctcctgcctt agcctcctga   18420
gtagctggga ctgtaggcgc ccaccaccac gcccggctaa ttttttagta gagacgaggt   18480
ttcaccgtat tagccaggat ggtctcaatc tcctgacctc atgatccacc cgcctcagcc   18540
tcccaaagtg cagggattac aggcgtgagc caccgtgccc agcccaaaag cttcgttatt   18600
attaattttt ataattcaga cgttttgcct cttttgtcaa gtgcatgaaa tttgagatgg   18660
gtacagctga gaaatgtatg atggctgtgt gctgaattcc tctagggtg  tatttgttta   18720 aatattgcca ataaggtgtt caaaataagg ttatttgaaa gagcaagttg aaatggaaag   18780
cttaggagag cttagttttt tgtttgtttg ttttttttgag atggagtttc gctcttgttg   18840
cccagactgg agtggaatgg tgtgatcttg gctcactgca gcctccgccc ccacaccatt   18900
caggcgattc tcctgtctca gcctcctgag tagctgtgat tacaggtgct caccaccacg   18960
cctggctaat ttttttgtatt gttagtagag atagggtttc accatgttgg ccaggctgtt   19020
ctctcctgac ctctggtgat cctcccactt tggcctccca agtgtaggg  attacaggca   19080 tgagccacca tgcccggcct cagcctatag ttctttaat  gcccttgtct actaattctt   19140
tcatctgtgt catttctggg tcagtttcag ttgcttgatt cttttttttc ttcctctttt   19200
tgggttgtct tttccaccta ctttgcttat ctgttgattt ttggatgcca gacatcatga   19260
attttacttt gttggaggct ggatatttt  gtatttctat aaatattctt gagttttgtt   19320
ctgagatgtg gttaaaatac ttaaaaatag tttgatgaag tcttgctttt aagctctgtt   19380
aggtgagatc aaaaccattt tagtgtaggg ctaagtattt cccactattg agtcaaaatc   19440
cttttgggga ttctgtgtga tagcccatgg actatgtggt tttccactct ggctgtgagg   19500
aactggccct cttcctgttc ccatgtgagc cttgtggatt gttccatttg attcttttgg   19560
gtattttatt tatatttta  gagaaggtgt cttgctctgt ccctcaggct ggagtgcagt   19620
tttgtgatca tagctccttg cagcctcaaa ctcctgggct caagccatgc accccatata   19680 gctgggcta  taccatgcct ggttattttt attgttttag atatagggcc tcactgtgtt   19740
gcccaggctg gccttgaaga ctccagggtt caagcgatca tccttcctca gcctccccag   19800
tagctgggat tacaggattt tgccatcaca tctggctaag ggggtgtgga accagggaca   19860
aagaccaaat acatatttca taatatacta cacaaggtaa atctggttca tgtcactcta   19920
ccttgactgg aagcataagt atagattttg ccatgttgcc caggctggtc ttgagctcct   19980
agcctcaagc ggtcccctct tcccaaacct tggcctccca aaggtgctag gattgcaggc   20040
```

```
atgagccact gcacttcctg agtagctggg attacaggtg cgcgccacca cgcccgctaa    20100
tttgttttgg attttagta gagacggggt tttgggccag gctggtcttg aactcctgct     20160
cttaagcgat ctgcccgcct cagcctccca aagtgctggg attacaggtg tgagccacca    20220
cgcccggtct gattttgta ttttttgtag ggatgggggt ttccccatgt acccaggct      20280 gctcttgaac tcctggcttc aagcaatcca cctgcttcgg cctcccaaag tggtgggatt    20340
tcaggagtaa gccactgcac ccagccttgt tcatttcaat attcctgatg aagtactcca    20400
tctgatctca tttgctctta gaaatctgct tgctggttac cctgtgcagt ggctcacact    20460
tgtaatccca gcactttggg agactgaggt aggaggattg cttgatgcca ggagctagag    20520
atcagcttgg gcaacatagc aagaccttgt ctctacgtgc acctgtagtc ctggctactt    20580
gggaggttga gatgggagga ttgcttgaac ccatgggttt gaggctgcta tgaggtatga    20640
tcacaccact gcattttagc ctgagagaca ggagacagta tctcttagca aaaaaaaaa     20700 aaaagaaaaa acaaatctga ctaccgtatt gatgattcta gtccagaatt ttccaaagga    20760
gtataggtgg ttttttttggt tgttgttgtt gtttgttttg tttttgaga tggtgcgagt    20820 ctcgcttttt ttgttttgtt ttgtttttt gagatggagt cttgctctgt cgcccacgct    20880
ggaatgcagt ggcacaatct cggctcattg caaccttcgc ctcccgggtt caagcagttc    20940
ttgtgcctca gcctcccgag tagctgggac tacaggcgtg cgccaccacg cctggctaag    21000
ttttgtattt ttggtagagt tggggtttca ccgtgttggc ctggctggta tcaaaactcat  21060 gacctcaggt ggtccgccat tctcagcctc ccaaagtttt ggaattacag gtgtgagccc    21120
tcgcacctgg cctttttttt tcttttttaa acatatttat ttatcatttt tttttttttt    21180
tgagacggag tctcgttctg tcgcccaggc gggagtgctt tggcgcgatc tctgctcact    21240
gcaagctccg ccttccgggt ttacgccatt ctcctgcctc agcctcccga gtagctggga    21300
cgacaggcgc ccgccactgc gcccggctaa ttttttgtat ttttttggaga cgggtttt    21360 caccatggtc tcgatctcct gacctcgtga tccgcccgcc tcggcccccc aaagggctgg    21420
gataaaaggc atgagccacc gcgccccgcc aacctttttt tttttttaa agaggtggag    21480 tataactatg ttgcccaggc tgatcttgaa ctcctggcct caagcagtcc tctaccttgg    21540
cctcacaaag tgctgggatt acaggagtga accaccgcgc ctggctgaga taggttgttt    21600
tttgaattaa ctattctttt tttttttttt tttttttttt gagacagagt ttcgctgttg    21660
ttgcccaggc tggagtgcag tggtgcaatg atctaggctc actgcaacct ctgcctccca    21720
ggtttaaggg attcgcctgc ctcagcttcc caagcagctg ggattacagg catgtgccac    21780
tacacccggc tgattttgta ttttttggtag agacgggtt tctccatgtt ggtcaggctg    21840
gtcttgagtt cccaacctca ggtgatctac cctccttggc ctcccaacgt gctgggatta    21900
taggcgtgag ccactgcacc cagccatgtt tttaagattt ttaaacatct ggctcttttt    21960
tttttttttt tttgagacgg agtctcgctt tgtcacctag gctggagtcc agtggcgcca    22020
tctcggctca ctgcaagctc cgcttcctgg attcactcca ttctcctgcc tcagccccca    22080
gagtagctgg gactacaggc acccgccacc atgcccggct aatttttttgc attttagta    22140 gagacgggt tcaccacgt tagccagcat ggtctcgatc tcttgacctc gtgatccgcc     22200
cgcctcggcc tcccaaagtg ctgggattac aagcatgagc cactgcaccc agcccttctg    22260
gctcttttta aatgtcagat attgataact cccagactga attaagattt tatatgtcag    22320
atgattaact atcattttga gttgttgctt agttctctgc ttgcttggca acaggtcagt    22380
```

```
ttccatggta ttgccattttt tgtaccgcat tcttagtgga gctgagaggt tgggggtgag   22440
gctacagggc cgaactctat aaactagaat agctatactt ttatccagtt tggtgtataa   22500 aaggggtga gatacggctc aggaaaagca tataaaaaac aaaaataaaa ataatttctg   22560
aataattttt ttttttttt gagacggagt ctcgctctgt cgcccaggct ggagtgcagt   22620
ggcgtggtgt cggctcactg caagctccac ctcccgggtt cataccattc tcctgcctca   22680
gcctcccgag tagctgggag taaaggcacg tgccaccatg cccagctaat ttttgtatt    22740 tttagtagag acgggttttc accatgttgg ccaggatggt ctcgatctct tgacctcgtg   22800
atgtgcccgc cttggcctcc caaagtgctg gataacagg cgtgagccat agtgcccggc    22860
ccccccgccc ccaccttttt ttgagacaga gtcttattct cacccagcct ggagtgcagt   22920
gtttacgatc ttggctcact gcaacctctt cctcctgggc tcaagtgatt cttctgcttc   22980
agcctcccaa gtagctggaa ctacaggtgt atgtcgtcat gcctggctaa atttttttt    23040 ttaatatttt ttagtagaga cggggtttca ccatgttgtc ccagctggtc tcgaaccct    23100 gggctcaagc aatccaccca tcgtggcctc ctgcagtgct ggggttatag gcatgagcca   23160
ccttggcctg cataattctt tttttttttt ttttttgaga tggagtttcg ctcttgtcgc   23220
tcaggctgga gtgcaatggt gcgatctcgg ctcaccgcaa cctccacctc ctggattcaa   23280
gcaattctcc tgcctcagcc tcccaagtag ctgggattac aggtgtgcac caccatgcct   23340
agctaatttt gtattttag tagagacagg gtttctccat gttggtcagg ctggtctcca    23400
actcccgacc tcagattatc tgcccaacct tggcctccca agtgctggt attacaggtg    23460 tgagccacca cgcctggcca ttaattcttt tttaagaaag agtttcattg ctattaaaca   23520
agtttgaaaa tcacagtttc tgcaaaagta gaaaatacaa acttgggttt ctaccactac   23580
actttcacaa catgcttttg actccagatt tgaggggga tttctcccca acaggaggta    23640
ggccatcagt tctgcagtgg gcagcagctg ggcatcctct aattgaattc agttctgaca   23700
ctgtctacac tacccgctta gagatggatg gtgacacata aacacaggtt gagnactcag   23760
acctataaca tatattgtac gtaaattgtc atttattttg tctgtggttc tgaccagcca   23820
gctgcaaatt tcaagagttc ctgcagatac ctcctttact tcaattactt tgctagagtg   23880
acttacagaa ctcagggaaa tgtgtttatc catttattac aaaagataca tgtgtatatg   23940
tgtgtgtgtg tgtgtgtgtg tgtgtgtgtg tgtgtgtgtg tatgtgtgtg tgtgtatata   24000
tatatttaaa ttttatttga gttagggtct ttccccagtt gccaaggctg gagtgcagtg   24060
gtgcgatcac agctcactgc agcttcaact tcttggactc aggctatcct cccatctcag   24120
cctcctgagt aggtgaaact atatacacac agcaccatgc ccagctaatt aaattttttt   24180
ttggtagaga tggggtcttg ctgtattgcc caggctggtc ttgaactcct gggctcaagc   24240
agtcctccgg ccttggattc ccaaagtgct gcaattacag gtgtgagtca tcatgtttgg   24300
cctacaaagg atatttggaa ggatgcaaat aaacagtcag gtgaagagat acatataggg   24360
ccaggattga aatggtccct agcactgttt tttctgtctt cttggagttg ggatgggcca   24420
ccctcccctc acatggctgt gcttctcttt actcctgcaa tcccccatgt gtttggctcc   24480
ctacaagcca tgttcagctc cctgcaagct ctctgaaccc aatcctttca ggtttttatg   24540
aaggcctcat tacgtaggga tgactgatta aatcttttgg ccattggtga tgaattaaaa   24600
gttcagtccc tctcccctcc ttggaggttg aggtgggagt tgaaaccatt tgtcatccta   24660
agctaacaaa cggttgccag ctattggtca actcattggc atacaaaaag acacattact   24720
ttgaagatac cgaggatttt aggagttgaa gggccaggaa acaggaaggc caaatatata   24780
```

```
tttcacaata tcacaatatg ttattaagag caaatagtga tagaaaagtg aaagtgatga      24840
tagcagaaat gtaaagtgta ggttctataa acagtgcaga tgagaacaaa gctaacagtt      24900
atcaggcagt ctaaatgcat gcagtttttt accttagaca cattcgttcg ttgactgttt      24960
aattgtaaag aaaaatcaat ttaagaacat gtatgaaatt gcatttatac tctggaaaaa      25020
tgagatgtaa gtaggtattt tgtattttt agcgtttcaa gagcataatt ccccttatgg       25080
tatgtctgtt gccttgcttt cacacattcc acttgtgtac atgttttgg gaactcatta      25140 tgtaagaaag taatggactt cttacacttc tgttaggtaa aaccatagta attggctggg      25200
catgatggca tggggtggga ggatcacttg aggacaagag tttgagcttg cagtacactg      25260
atctttgctg tgaatagtca ctgcactcca gccggggcaa cgaagacact gtctctttct      25320
tttttttttt tttttttttt tgatggagtc ttgctctgtc gcccaggctg gagtgcagtg      25380
gcacagactt ggctcactgc aacctccact tcccaggttc aagggattct cctgcctcag      25440
gctcccaagt agctgggact acaggtgcct gccaccatac ctggctaatt tttgtatttt      25500
tagtagagac ggggtttcac catattggcc agactggtct cgaactcctg accttgtgat      25560
ctgcctgcct cggcttccca cagtcctggg attacaggcg tgagccaccg tgcctggccc      25620
aagactctat ctcaaataaa aagaacaca gtaattttc tcttttatgg gatactacac       25680
ttacataagt ttctttttt tttctttttt tttttttttt gtgagacaga gtcttgcttt      25740
tcccctgcca ggctggagtg gagtggcatg atctcagtca ctgcaacctc gcttcctgg       25800 gttcaagtga ttcccgtgcc tcagcctcct gagtagctgg gattacaggc gtgccccacc      25860
acgtctggct aattttgta ttttagtag agatggggtc tcaccatgtt tcccaggct        25920 gttctcaaac tcctgagctc aagtggatcc cccctgcctc ggcctcccaa agtgttggga     25980
ttacagtcgt gagccactgt gcctgtctgg gatgtttgcc atatttgttt catcagtata     26040
tatttctttg cttgggttga gtacagggac tgatgcctgt aatcccagca cttagggagg     26100
ccgaggtggg aggattactg gaacccagga agttgaggct gcagaccaac ctaggcaaca     26160
gagtgagaac atgtcttcag ggggaaaaaa aaagcgctgg gcatgggcat atacctatag    26220
tctcagccac cctggaggat gaggtgagag gatcgcttga gcccaggaat tgaggctgc     26280 catgagccgt catcatgccc atgccaatgt actccagcct gggcaagaaa gtcgaccctg    26340
tctcaaaact aaactaaaca aatttctctg gctgaagtat agtaatttgc ttttaagtga     26400
cgtttgtaca ttttagaaaa taactttgta tatcagacat catttatggt acttaccgtt    26460
ttccatggtc ataaaatacc tagtctagtg tgataaatgc caggtgatag aggtatgcct    26520
ggggcataaa cctaggggct tggtgggatg gggtgagatg gttgaaatag tatgtagaag   26580
gaaaggcttt ccagagttta ctcttagggt ggctcttgaa gggcaagtga aggaaagaca     26640
tttcaggctg agggaagaca cgtttagatg gagtcctgtg gatggagagt gctggacttg    26700
tttgcgaagt caggagtagt ttgatatgat cagatgctta gggaggtgat tggtaaagtg     26760
gtggaaggtg agattgtgga acaggtaggc atggacccta tcacaagcgt cctggcttgt     26820
gtatctagct aaaggatctg tctgtctgtc tgtctgtctt tatattttt gagacggagt      26880 ttcgctcttg ttgcccaggc tggagtgcaa tgatgcaatc ttggttcatt gcaacctccg     26940
cctcccaggt tcaagtgatt ctcctgcctt agccttctaa gtagctggga ttgcaggcgt     27000 gcactcacg cccagctaac ttttattttt tagtagagtt ggggtttcac catgttggtt     27060
aggctggtct tgaactccta acctcaggtg attcacctcc ctcagcctcc caaaatgctg     27120
```

```
agattacaga tgtgagccac cccacctggc ccatgcctct atctatctat ctgtctgtct   27180
gtctatctat ctattctatc taatcttttt tttttttttt tttttttttg gagtcaggtt   27240
cttgctctgt tgcccaggct ggactgtagt ggcgtgatct tgcctcactg cagcctctgc   27300
ctcccgggtt caagcgatct tcctgcctca gcctccctgg tagctgggac tacagatgtg   27360
tgccaccatg cctggcaagt tttatatttt ttggtagaga tggggtttca ctatgttggc   27420
caggctgatc tcaaactcct gacctcaggt gatctgccca cctcagcctc ccaaagtgct   27480
gggattacat gcgtgagcca ctgtgcctgg cctgttaagt attaccataa actcttctcc   27540
tatctgtctt gtaagttatg tacacctcat ctatgttctt gatgtagctt gttacttagt   27600
ctgttatagt aataatctct ttaattatta gcttttatgt cttctccatt gtccactgac   27660
agccataact gcgtatatct ttttgtatac ctgtctacag accagccatc ctaggttgaa   27720
gaatagaatt acttctcatt gcttccacag ttcctgtctt cctttaaatc atcatgtata   27780
acacaaatta tacagtagct ttcttgtaaa tctcctgctt ctgtatttta tatctgttag   27840
gctgggtgca gtgactcact tctgtaatcc cagcactttg ggaggccaag gtgggaggat   27900
tgcttaaggc caggagtttg agaccagcct gggcaaaata gggagacacc ccgtcaccac   27960
acacttatac acacacacac acacccccccc acacccacca tgaaaaaaat tagtcgcggc   28020
ggggtgcggt ggctcacgcc tgtaatccca gcactttggg aggccaaggc aggcagatca   28080
catgaggtcg ggagttcaat accagcctga ccaacatgga gaaacccccat ctctactaaa   28140
aatacaaaac tatctgggcg tggttgcaca tgcctgtaat cccagctacc ctggagtctg   28200
aggcaggaga atcacttgaa cccgggaggc agaggttgtg gtgagccgag atcgtgccgt   28260
tgtacttcag catcaacaag agcgaaaccg tctcacaaaa aaaattagtc gggcacaatg   28320
gtatgcatct gtggtcacag ctatttggga gactgagcta ggaagattgc ttgagctcag   28380
gaattcaagg ctcagtgagc tctgattgtg gcactgcact ccatcccggg ccacagagac   28440
tctgtttcta ataaataaat aaaatgtaaa ttagctgttc ctctgtggct tacaaccttc   28500
cagtggctcc catttcactt agagtaaaag tgaaagccct caccgtggtc ccctccttttt  28560
ttgctgctcc attactcttt ctttatctcc ttcacttcat tcagatcatt gctcaataag   28620
gcctctccta acctacctat ctgcaagtat ctctagaata tgacttaaaa acaatctaaa   28680
cacagatgtc acaactaaaa aaaattaata cttagtcctt agtgtcatta aatttctggt   28740
cacctattgt taaatagttg ctttgtttga aggtcactgc aacctgcatt tcctgagccc   28800
aagctatcct cctgtttcag cctcccgagt agcagagact acaggtgtgc accaccatgc   28860
ccagctagtt ttttagaatt ttttgtagag acaggatcta actgcgttgc ctaggctggt   28920
cttgaactcc tggcctcaag tgatcctctc accttggcct cccagtatgc tgggattaca   28980
ggcacaagcc actacatcta gacacgaatt tctgatttaa ataattcttt gtaagaacac   29040
ttcttaggag gcatttgaat ggataactgt cttaactgtc ttgcacacca gtctttgtct   29100
tttttttttt tttttttttt ttttttgagaa aaggtcttgc cctgtcaccc aagctggagt   29160
gcactggtgc aatcacagct tactgcagcc ttgaactcct gggctcaaat gatcctccca   29220
ccttggcctc caaagtgttt ggattacagg catgagccac tgagcccagc ctcaggttgt   29280
ctttctcctg ctttactatt tcattttttt cttttcgtct tctagcgtac tgtaaattta   29340
catatatttt aatgtctgta ctagaatata agctcaacaa gggtagggct ctttgtgtgt   29400
agacattgct cagtacatag ttggcacgaa ataaaatcac ttaaatgaat gaatgagtga   29460
aatacaaagg cggaatttga ctgtaaaaca gtcttgttgg agaaggtata tgggaatag    29520
```

-continued

```
gggaaagaga gggcctcttt tcgccctcct acattgatac agatagatct cagttggtct    29580
ctgatcttgt ttgtagggat tttgttggat gaatgcaagg tgggatggtc ttcagattgt    29640
accaatttag ctggcattgc taaccaactg ttggaatctc tgaaaataaa agatcttgaa    29700
attcctcccc ctctccccgc aaagagaaat acgaaggcag acaactgggt aaattgtcct    29760
acccctaact gccatccaca gaaaagtaac attttgtttt atttgattaa ctgtgcttga    29820
caacattaga aacagtggaa aatcatctgg gacttgggca ggtagaaact ccagaggtag    29880
gactggagga ggggctgtgt aacctctctt tcttactctt aagaataacc ttttatcta    29940
cccgagattt attggctcct taaaatcata actaaaacct gtagcctctt tcagcagaaa    30000
gcaatgctta gagtaagact tctactacac tgccagcccg aaggcttgaa cagaaggcaa    30060
gtggaagccc taaaactttg gctgttcctg gcacgattcc agtcccactc tccctaccct    30120
cacccacagc ttccccatca ctgtctgctt gggaaccgtg agcattgttc tcatcttgtg    30180
cttctttctg agttatcagg cagccggaag gccagattcc cttgtcttcc ctcttttcat    30240
ggactctgca ttttcttttc tgatcctgtt tttcacctttg atcttcttgg aacttttccc    30300
tgagcccttt taaactcacg gtatatcagc aaaattcccc taatcttcag tttcttctgt    30360
gatttccgcc ccccgcccca cacattctta ttctgactga aaataggcca tctcctgatg    30420
acactgcctc cctgcagccc tccgaaagag tacttgcctg cccctccatc cctttgtgt    30480
tactaggctt cacagtagca tgtcctcttt ttctttgttg ccatttcttt acttttcttc    30540
tcgcctccct aaaaacacct ctgaatgtga tgtcatgagt ttgtactatg cgctcctgat    30600
ttttgctgct taatccagtg tgctgtggag gattgaacct cttatgatgg agttccctc    30660
tttaactcta gtaatgcttc ttgccttaaa gtctgctttg tctaatatca gtatagctat    30720
gccagttttc ttttgtcg tgtttgaatg gcatcttttt ctgtcttttt tattttcaac    30780
ctttctttat tcttgatgtc ttggttatgt ctgaacaggt tttcatccac atcttaaaag    30840
cacatctttg cttttaactt gcatttagtt tcattcacag tttcatttaa tgtatttatt    30900
gatatatctg tatttagatc taactcagag atttctattt gacccacctg ttctgtgtgg    30960
gtttgttttg ttagtccttt tgatcttcct ttgcattgat ttagtattta ttgttattct    31020
tccctcttcc ttagcttggt aattgtgtgc tatttggaaa aaatactatt ctctgagtag    31080
ttatcctaga gataacaatt tacttccttt atttatttat tatttattta tttatttatt    31140
tatttattta tttattttga gacggagtct cgctctgtcg cccaggctgg agtgcaatgg    31200
cgcgatcttg gctcactgca agctccgcct cctgggttca cgccattctc ctgcctcagc    31260
ctcccgagta gctgggatta taggcgccca ccaccacgcc tggctaattt tttgtatttt    31320
tagtagagac agggtttcgc catgttagcc aggatggtct tgatcccctg atctcctgat    31380
ccacccacct cggcctccca aagtgctgag attacaggcg tgagccacag cgcctggcca    31440
acttccttaa tttattaatc tcatgttgac ttggcttctc aagaaggctt aagaatccta    31500
aagggaagct gggtgcggtg gctcacgcct gtaatcccag cagtttggga ggccgaggca    31560
ggcggatcat gaagtcagga gatcgagacc atcctggcta acacggtgaa acccatctct    31620
actaaaaaaa atacaaaaca ttagctgggc atggtggcgg gcacctgtag tcccagctac    31680
ttgggaggct gaggcgggtg gatcatgagg tgaggagatc gagaccatcc tggctaacat    31740
ggtgaacccc atctctacta aaaaaatac aaaacattag ctgggcatgg tggcgggcac    31800
ctgtagtccc agctacttgg gaggctgagg caggagaatg acatgaacct gggaggcgga    31860
```

-continued

```
gcttgcagtg agctgaaatt gcgccactgc actccagcct gggcgacaga gggagactcc    31920
gtctcacata aataaataaa taataaaata aggctgtgca tggtggctca cggctgtaat    31980
cccagcactg tgggaggccg aagtgggcgg atcacctgac gtcaggagtt caagaccagc    32040
ctggccaaca tggtgaaacc tacctctaca aaaaatatac aaaaattagc tgggcgtggt    32100
gccacccacc tgtaatccca gctacttggg aggcttaggc agagaatctc ttgaacccag    32160
gaggcagagg ttacagtgag ccaagatcat gccaactgca ctccagcctg gcatcagtc    32220 taaaataaat aaataaataa aattcacacc taggacatca caataaaata gatcgcttga    32280
gcccaggagt tcgagaccag cctgggcaac ctggtgaaac actctctcta caaaaagtac    32340
aaaaattagc caggtgtgat ggtgcgtacc tatagtcaca gctacttcgg agactgaggt    32400
aggaggaaca cttgagccta ggaggtcgag gttccagtga gctgagatct taccccctaca   32460 ctccagcctg ggtgatagga cgagaccctg tctcctcctc agaaaaaaaa aaaaagcatt    32520
acttaatctc ttagcctctt aatggccccc tctggaatag gcaaataagg gggaaactgt    32580
gggggaaagc ccaataccta cacttccctt ttgtttttttc tggaagtctt cccctttttc    32640
cccagctgga atgcagtggc acaatcatgg ctcaactgca gccttaatcc cctgcgctca    32700
agtaatcctt agcctcccaa gtagctggga ctacaggtgc atgctaccat acacctggct    32760
aattaaaaaa gaaaaattat ttttgtagag ataaggtgtt actgtgttgc ccaggctggt    32820
ctggaactcc tcacctcaag ggatcctctt gcctgggcct cccaaagtgt tgggattacg    32880
ggcgtgaacc actgtgcctg gcctgaagtt ccctttctga aggcagcagt ctctcttgca    32940
ttccaggtct atcttgttac tttttttttt tttttttttt ttttgaggca gagtttcact    33000
cgttcccagg atggagtgca atggcacgat cttggctcgc cgcaacctcc acctcctgga    33060
ttcaagcgat tctcctgcct cagcctcccg agtagctggg attacaggca tgcgctacta    33120
tgcccggcta atttttgtatt tttagtagag acagggtttc tccatgttgg tcaggcttgt    33180
ctcgaactcc tgacctcagg taatctcccc gcttcggcct cccaaagtgc tgggattaca    33240
ggcatgagca accgcgcctg gcttttttttt ttttttttaaa tagagacagt gtctcactat    33300
gttggccagg ttggtcttga actcctggct tcaagcaatc ctcttgcctc agcccctcaa    33360
agtgctagat tacaggcatg agccattgtg cccagttgtt acttttctga ttccttcaaa    33420
cagatgttaa tattttgttc acttttttcca gttgttctgt agtgggaggg gtctgaatga    33480 cttggttttcc tagaagggaa gtaggtagtt tctacctttc tgttacgtag tctagtataa    33540
tttctgtgtc ttttcttatt tcagtatgcc taatgatatt cttcccagag ccgctgtgaa    33600
tgactgcata ggttgaacac aacaacacag tgaccctaat ccttccgata ccttggcttc    33660
ttagttcctt gacctctatt cctgggatcc tgttctctgc cctacctcag ccacccattc    33720
ctttgagtta ctgttaccctg aaattcatac cctttttatct ctgtttcaga cttagcactc    33780
tacatcctcc tgatctttcc agctgatgcc cttccagcat ccctgtgatc tttgactcca    33840
tcatgacgtc agttcattga ttataccacc ttttcccttg atgtttctta cgcttttgtt    33900
cagcttaaat tccagtcatt agaacacaac ctctcctcct attcctttgt cttcttgttt    33960
cattagttct tttggctatg ccacaacctg tgttttactc tcattccccg gaaaatagag    34020
catacaacaa gctttttact gggctaatac tttacttgaa gttagaatga agggaaaat    34080 agaaagtgag acaggaaagg agggaaagca aatacagagt gctacgttat ccagcaggct    34140
acagcatcat aagaacctta gctggctgct cagtcatgtt ggaaatctct ggagaatcat    34200
ggcacctctc agaatacttc tggggacagg tttgagggag gatggctgag agatttattt    34260
```

```
gttggctccc tctcatatcc tgtctcttac tggtcagagt tgcctgaagg atcttaatta    34320
ttctatactt ttgggtttgt tacttggctt ctctatgcag ctgctggaaa agcagctgat    34380
ttggggtaac agggcttctg ccacagcagg cacagtgagg accaccaaag cctacctgtt    34440
aacactgggg aggtagagac cactagtggt aggctgagtt catatgatcc tcccagattg    34500
caggattttg cttgtgctgc tgagcctgct tcagctggga agtagaacag caggcaggac    34560
cgagtggatt ttggaaagtg tgtatgagct gcatttgtta taccttgtgt aatccaactt    34620
tttgcctatt ctttgcttgc tttcccatag ctcaatgtgg ctggagaaac catactgatc    34680
actctgactt cacagtcatg attaccaaga ccaagaggct tttattatag gttatagtct    34740
gttttcctat tccaattact cttctagata gtttaaatgt cttactttaa tcctctaatt    34800
ctccctgcct tatcctccct ttatttcatt ggggaaaaaa cctgaatcaa ttagaagaaa    34860
actactcact ccccttacca gatgtgctac ctgtctacat ctgtgcctgg tactctgcct    34920
tctgtaactg ctagctaagg ccaaaccctg tgcacgtata ctaggctcca tgcttttcta    34980
cctgtttaag gataatcact ccagtagttc atcctttatt tgcatcatca aatttttcat    35040
ctctgttgta tcattcttat cagcgtatta aacgggctat tacttcttgt ttaaaaactt    35100
ttttgccggg tgtggtggct cacgcccgta atcccaacac tttgggaggc caaggctggc    35160
ggatcacctg aggtcaggag attgagacca gcctggccaa tgtggggaaa ccccatctct    35220
actaaaaata caaaaattag ctgggcgtgg tggcgggtgc ctgtaatccc agttactcag    35280
gagactgagg caggagaatc gcttgaaccc gggaggcaga ggttgcagtg agctgagatt    35340
gtgcccctgc actccagcct gggcgacaga gtgagactct gtcttaaaaa aaaaaaaaaa    35400
cacacacaca caccaaaaaa acaaacttct tttggttatt ctgattctgt atattctttc    35460
ttttctccta ttcttttaca catttcattc aggcttttgc ccccactgct cctctagagt    35520
tgctcttgag gtgatcaatt gctccatgtt gctaaatcca gcaatctgtt tgcagtcttc    35580
accttatttg aaatatctaa cccaagagac atatgtgtct gtgtgtgcgt gtatatatat    35640
atgtatataa tatgtatgaa gggtttatat atgcataaat ttaaaagggg tgtgtgtgtg    35700
tgtgtgtgtg taaaattgac cgacatgact gtgaaggcca ggaagtccca aaatctgcag    35760
ctggcaatct ggaatcccga gatagctgac agggtaagtt ccagttcaag tccgaaggca    35820
cgagagccag gtgagccagt gtctcagctc aagcagtgag acccagagga gttccctctt    35880
aaactcagcc ttttttgttct cttcaggctt tctgtgggtt gtatgagtcc cacccacatt    35940
aaggagggca gtctgctttta ctcagtccac ggattcaaat gttcatttta tctgaaagca    36000
ctgtcacaga tagacccaga ataatgtttg accaaacatc tgggcactct atgctgtagt    36060
ccagttgatg cataaaatta accattacag aaccttttct tcacttgaca tttagaacag    36120
gatgccaata tagtccctat aagagctagt ccctggcttc agctccacta cccgctcccc    36180
cgcttttctc tctctctctc tcttttcttt ttttgttttt ttggagactg agtcttgctc    36240
tgttgcccag tgactcactg caactccaaa aaaaaaaaaa gccttactaa taaaactctt    36300
agcctcttag tggatccctc tggaatgggc caataagggg gaaagcccaa tacctgaact    36360
tctcaatgaa aatcctgggt tcaaacaatt cttgtgcttc agcctcccga gaggtgggat    36420
tacaggcacc caccgccatg cccggccaat ttttgtattt ttagtagaga cggtgttcca    36480
ccaagttggc caggctagtc tcgaactcct gacctcaagt gatccaccca cttcggcctc    36540
ccaaagtgct gggattacag gcgtgaggca ccacgctcgg cctccccttt tctctactgc    36600
```

-continued

```
agtcagaggt gccaacttgc tcttttttt tttttttttg agacggtctc gctctgtcac    36660
ccaggctgga gtgcagtggc atgatctctg ctcactgcaa actccacctc ctgggcccaa    36720
gcgatcctcc cacctcagcc cctccccaag tagctgggac tacaggcgtg cgccaccaca    36780
tgcctggctc attttgtat tcaacacgct gtttcctgac cgtagctgga taggcttctg    36840
tgttggggc tttgcactca ttcatctgcc tgaagtgcct ccttgctgct gggcacctcc     36900
tccccatcca catagcccat ggccttattc ttgccacgtg tactgaaatg tgacattctc    36960
atgagggttt tcctcatcag tctgtctcag ttttcagctg catccccggc acttcctgtt    37020
cccccttcctt gttttctt tttctcattt actcttatcg tcatctaaca cacttcctta    37080
tttatcttgt ttattgtatg attccttcaa ctagacggta aactgtgagg tgagaggaga    37140
gcttttaaa atcttgttgc cttaacagcc tccccccccc ccaccactgc ttctagaata     37200
gtgcctggtg caaatttgcc tctcagtaac aagttttctg tttatttaaa aatacggacg    37260
gaatttcgaa gctttgtgat agagataaaa aaaatggaca ggagcttttc ccaggaggta    37320
tacaaagtat aggtgtctgg cctggaactc tccacaaaga ataccttttat tgctctacaa   37380
atgctatttg tagtctaaac atggatgagc tgatacaatt ctgaaggcac cttgcagcct    37440
tctctccttg cttctagctc cacgtgtgtg cgagtctgca tatgtgagtg taagggcagc    37500
actgtgttaa agagatttac aaacatcttt ttaatcctca taacaatcct acaccacaca    37560
tgtcatcatc cccttttgtac agaccataaa actgatattt agagagctta acgtcttgc    37620
ttgaggcctc aagtggtaag tggcagaact cagcttgaag tgacttgact attattacat    37680
tatatgtgac ctcctagata aagagatgcc tccttatttt gtgtaaggca gaagtgggga    37740
gtcttgggca gattacttaa ccactgctat agtttggatg tggtttgtcc ttagcaaacc    37800
tcatgttgaa atttgatctc cagtgttgga ggtgggccct aatggaaggt gtttgtgcca    37860
tggggctgga accctcataa atagattaat gccctcctgg gtgagggtg agtgagttct     37920
tactcctta gttcctacaa gagctggttg ttaaaaagag ctggcgcctc tctcttgctg     37980
cttctctggc catgtgacct cttcacatgc tggctcccct tcaccttccg ccatgtgtgg    38040
aagcagcctg aggctttcac cagatgcccc atcttccagc cggcggaatc atgagccaag    38100
tgaatttctt ttcttttgtca gttacccagt gtcatgtatt cctttatagg aacactaaag   38160
ggactaagac aaccccttta ggtcctaatc atatacatac ttatagattc aaagtatctg    38220
cttagcatgt actccattca aagcaactgt tcaaaggtaa gaatcctatc agggatcagt    38280
gcagaaatac gacaccttac acatttctca gctttcacct tcccagagct tcctcggatt    38340
ggtcctcctg ttagtttcct ggatctgaag gtaatacctc atccagaaga taagaagggt    38400
agtggggact gtcaccacga aggagctttc cttttctggt tcaagttatt tcccagctcc    38460
actcacctcc ggactgtttc atgaagaatt ccagaagtcc ccttctccct cataggaaag    38520
tgcaccgaac cactcagatt taatggctta aaacaactgc tggtatttga ggatttgttc    38580
aggtgggcag ttgtggttct gggctaatgg gggccggtgt catctgcttg ctccactgtg    38640
atctggaaca gctgggcctt ttttcttggt tactgtgtag tctcacgacc tctccttttc    38700
cagtgaggtc tgcagtagga cctgatggct tatgcagtgg ttcagggcaa acattcccag    38760
aggaaggaaa cagaaactgc cagttctttt tgaagtgtag gcccagaact ggtatatcat    38820
cacttctgtc acatttcccc gatgactttg tgtctctgac catcccaaac tcactgtgag    38880
aagtgactgc atgggtgtg ggagtaggtc cattgggagt ggactagtcc agacctttt     38940
ttttttttg agacggagtc ttgctgtgtc gcctgggctg gagtgcagtg gcgcaatctc    39000
```

```
ggctcacggc aagcctcgcc tcccaggttc acgccgttct cctgcctcag cctcccgagt   39060
agctgggact acaggcaccc gccaccatgc ccagctaatt tttttttttt ttaagtagag   39120
acggggtttc accgtgttag ccaggatggt ctcgatctcc tgacctcatg atccgcctgc   39180
cttggcctcc caaagtgctg ggattacagg tgtgagccat cacgcccggc ccagtccaga   39240
ctatttttga gaataaaaag gggcctatta aaattatgt caggttgaca gacataaact    39300
ggaactgtcc tcacctagtc tggacatgtg gtatcatta tcatctctac aacttggaga    39360
aaacaacaca taggtgtgac cttgaatctt gaatctgttt tcctgcagtt ctcctaatgt   39420
gaaaatgtga ctgcattgag tatgcatgtg atgttttaaa ttgaatatag cttctaagca   39480
gaacccatca actcttcttt tctgttctgt tctttacttt tctttctttt ttttcttttc   39540 ttttttgag acagggtctc actctgtcga ccaggttgga gtgcggtggc gcgatctcgt    39600
ctcactgcaa cctctgcctc cagggttcaa gcgattctcc tgccttagcc tcccaagtag   39660
ctgggactac agactacaag cgtgagccac cacgcccagc taatttttt gtattttag    39720 tagagacggg gtttcaccat gttggccagg ctggtcttga actcctgacc tcaagtagtc   39780
tgcacgcctt ggcctcccaa agtgctggga ttacaggcgt gagccaccgt gccgagccac   39840
catcagattt tcttggtggg cactgaatga tgacagaaag agtttaattt aacactggag   39900
ggaaaaattg gctttgaatt tcctgagaaa taatttcgtt tgttgggttt ttttttttt    39960 tttgagatgg agtctcgctc tgtcacccag gctggagtgc agtggcatga tctcggctca   40020
ctgcaagtag cgcatcctgg gttcacgcca ttctcctgcc tcagcctctc caagtagctg   40080
ggactacagg ccccaccac cacgcccggc tcatttttg tattttagt agagacgggg     40140 tttcaacgtg ttctcgatgt cctgacctcg tgatctgcct gcctcggcct cccaaagtgc   40200
tgggattaca gcgcgagcc accgcgcccg gccagtttgt tggtttctaa tagagagctt    40260
tcctgaagga tttttcgttc ttttttcttt tttccccccct gcaagggaa ttttttcaaga  40320 ctgattttga ctgcatgcta tccttttcctt tcctttcctt tcctttcctt tcctttcctt   40380 tccttttcctt tccttttcctt tccttttcctt ttccttttcc ttttcctttc ctttccttttt 40440 cctttccttt cctttcttct cccctcccct cccggcgcct ccccgcccct cccctcccgt   40500
cgcggcgggt ggcgtgtcgc gtgtctcgtc tctcctctcc tctttcttt cttttttttg    40560 agacaggttc tcactctgtc acctagactg agtgcagtga agtgattata gcccctgca    40620 gcctcaaact cctgggctca agcagttctc ccacttcagc ctcctgagta gctgagacta   40680
tttgtgccac tacatctggc taattttaa attttttta cagatggggg tctcactgtg    40740
ttgcccaggc tgatcttaga ctcctggaca caagccatcc tcctgcctca gcatcccaaa   40800
agtgctggga ttacaggcat aagccactgt gcctggccag ctgttttcaa cctatatgct   40860
gacctggatc taatcctctc ataagataaa atttcactct gctgattaat cagatcattt    40920 taaggtctc atctagctct aagagactct aataatccaa tagaaagtgg ttacaaacac    40980
cgaaagtaca attgggaaga tataataaag gctttcacag ttcatatgtg atctggggtc   41040
agatgggatt caggaaactc catactttgt gttttctaa tattaaaaa attttatat      41100 agagatgggg tcttgccata ttatattgcc caggatactg ttgaactccc aggctcaact   41160
gattgtccct cctggcctc ttaaagtgct aggattacag gcttgagcca ccatgcttgg    41220
ctaccccata atttgaagga gagttagttg caattaaaaa tggaggtttt ttttctcttt   41280
ctctttgaga cggagttttg ctctgtcacc caggctagac tacaatggca tgatctcagc   41340
```

```
ttacagcaac ttctgcctcc cgcattgaag cgattctcct gtctcagcct tcttagtagc   41400
tggaattaca ggcgttcgcc aacacgcccg gctaactttg tatttttagt agagacaggg   41460
tttcaccatg ttggccaggc tggtctcgaa ctcctgacct caggtgatcc acccacctca   41520
gcctccccaa gtgctgggat tacaggcatg agccaccgta cccagtcctg gagtttgttc   41580
ttaacagaat atcaaatctt gagaagttga ctataaaaga aaattctaaa attaaaaatt   41640
ctattctctg tataatacat agaaggtaga ttttttgaggt atgacattta agatgtgagg   41700
tgcctctaaa atgtacacat acatgcttgt gtactccacg taattgtgcc tcaaggaggt   41760
agggtgaggc tttctgtctt tcctgaaaca tgttactctt gttcagtgct tggaaaaagg   41820
atgtggttag atggagtact ggcttgatac aattctctgt cttgcccagg gttgagggtg   41880
gtgtcaatga aaattctcaa tttgaatgcc atgtaatagg ctccttatta atcctgacta   41940
cagtataaaa aacaggctgg gcttcatggc tcacacctgt aatcccagtg ctttggttgg   42000
ccgaggcagg agggtcactg gaggccagga tttcaaggct tcagtgagct atatgattat   42060
gccactgcac tccatcctgg gtgacagagc aaaaccctgt ctcaaaaacc aaccaaccaa   42120
ccaacccgca aaaccaaaac agatctctcc aagcttcggc agatttgagt aattatgtga   42180
tctcttcttg actgaacaag tcacttgtca gatgaatatc tggtcccact atctagggac   42240
agaaggttcc cactaacatt gatttcaggt aatgcataac aaataaatac taagttttt   42300 gacatctttc cacaacatgt ttatattacg tgtgtgtgtg tatgtatgtg tgtgtgtatg   42360
tgtgtatata tatatatatg tatatatata tacacacaca cgtacataca tatatatatg   42420
tgtgtatata tatatatttt ttgggacaga gtcttgctct atcgctcagg ctggagtgca   42480
gtggcgcgat ctcgactcac gacaacctct acctcccagg ttcaagtgat tctcctgcct   42540
cagcctcctg agtagctgga attacaggca cgtgccacca tgcctggcta atttttgtat   42600 ttttttttt tttttaagtac agaaggggtt tcaccacgtt ggtcaggctg gtctcaaact   42660
cctgacctca ggtgatccgc ccacctcggc ctcccaaagt gataggatta caggtgtgag   42720
ccaccatgcc tggcctttttt ttaaagagat ggagtctggc tgtgttggcc tggttggtct   42780
tgaactcctg gcctcaagca gtcctcctgc cttggcctcc taaagtgcta ggattacagg   42840
catgagccat tgcacccagt ccaatgtttc ctagtttttc ttatgcaaac ttttaaattc   42900
ttctcagtat atatgtctaa aatcttctgt tacaaaaaaa tactgaagct gctgcacacg   42960
gcggctcatg cctataatcc cagcactttg ggcggcccag gcgggtggat cacttgaggt   43020
caggagtttg agaccagcct ggccaccatg gtgaaacccc atctctacta aaaatacaaa   43080
aagtagccgg gtgtcatggc aggtgcctgt attcccagct actcgggagg ctgaggtggg   43140
agaactgctt gaacccagga ggcggaggtt gcagtgagct gagatcactc cactgcactc   43200
cagtctgggt gacagagtga gactttgtct caaaaaagaa atggaagcaa tgtatattta   43260
ttaaaatatg tatatacata tacagaaatg agctaaaagt agctatatta ttattaaaat   43320
tgtatgcaat aatgattgca tagcatgttg gtatgaatat gaccataatt tgacgcaagt   43380
tgacacattt ttttttctaa tattctgtat tacaactaat ctgcatggat tgttttctg   43440 catgtaatct ctgcttactt ggtttaactt tttggtcgag tcctggaagt ggaattggtg   43500
aattaaaaat ttagatataa actcccaaat tgagccaggc gtggtgtcat gcacctgtag   43560
tcctagctgc taaggtggga agatcactta tgcccagcaa ttgcagtggg ctatgattga   43620
gccattgcac tccagccttg gtaatgcagt gagaaacata aaagtttctc cctccctccc   43680
tcccttctga cagagagtct cactctgtcg cccaggctgg agtgtagtgt caccactgca   43740
```

```
acctccgcct cccaggttca cgccattctc ccacctcagc ctcctgagta gttgggacta   43800
caggcacctg ccaccacacc cggctaattt tttgttttg tatttttagt agagatgggg    43860
tttcaccgtg ttagccagga tggtcttgtt ctcctgacct cgtgatctgc ccgccttggc   43920
ctcccaaagt gctgtgatga taggcgtgag caaccacacc cggcagtgag aaactgtttc   43980
taaaaaaaat ttttttaac gtagaaatct tttccttttt ttgagatgga gttttgctct    44040
tgtcgcccag gctggagtgc agtggcgtga tcttggcgca ctgcaacctc tgcctcctgg   44100
gttcaagcga ttctcctgcc tcagcctccc aagtagctgg gattacaggt gcctgccacc   44160 acacccgct  aactttttgt atttgtttac tagagatagg gtttcactat gttggccagg   44220
ctggtctcga acttctgacc tcaggctatt cttcccccca gggcctccca agtgctgag    44280 aatacaggtg tgagccactg cgcctggcca tagaaatctt ttcatatgtt tgtagatcat   44340
tcttctttga gtattctcta ttttttacct tcacccgttt tactgagttt cttattggtt   44400
tataagaatt tttttgctg gtgcagtgg  ctcacacctg taatcccagc ccttttgg     44460 gccgaggcag gcggatcacc tgaggtcagg agttcgagac cagcctggcc aacatggtga   44520 aaccccgtc tctactacaa atacaaaaat tagctgggca tggtggtgca cgcctgtaat    44580
cccagctatt tggaagactg aggcatgtgg atcacttgaa cccgggaggt ggaggttgca   44640
gtgagctgag atcgcaccat tgcactccag cctgggtgac aagagtgaaa ctctgtttca   44700 aaaaacaaa acaaaacaaa acaaaactct ttgcatattg aaggaactta ctagcaagcc    44760
ttttgacata gactttgtaa atgttttct tttgatgatt atatatatgg ttagtttggc    44820
tgtgtacaag tttttttgt ttgtttgttt gtttttttat tttttttttt ttgagacgga   44880
gtcttactct gtcgcccagg ctggagtgca gtggcacaat ctcggctcac ggcaacctcc   44940
gcctcctgtg ttcaagcgat tctcctgcct cagcctcccg agtagttggg attacaggcg   45000
cccgccacca tgcccagcta attttgtat ttttagtaga cgggggttt tactatgttg     45060 gtgaggctgg tctcgaacct cctgacctca gttgatctac ctgccttggc ctcccaaagt   45120
gctgggatta cagacttgag ccactgcacc tggccgcata tatatttt atttttttat    45180 ttaaaaaaat gtttctgaga caggatctca ctatgttgct gaggctggag ttcagtggtg   45240
tgatcatggc ccaccgcagc cttggcctcc tgggcttagg tgatcctccc atctcagcct   45300
cccaagtagc taggaccaca ggcaccatcg tgcttggcta atgtttagta ttttttttgta  45360 gagtcgagat ttttgccatg ttgcccaggt agtctcgaac ttaggagttc aaaacgatt   45420 gcctgccttg gcctcttcaa gtgctgagat tacaggcttg agtcacctca catggctgca   45480
aagcgatttt ttttgagaca catttagttt tttcggtgat gtcagtaatt ttacaattaa   45540
agaaaaagtt atctgaacaa agggagagtg cccttaaatt gctaagaggg agcattgctt   45600
tgtttttttc tagtttcgtt gtgtcttaca gtgttcaaac actgtactgg aagtaaataa   45660
ttaagtttaa ataatttttc ttctccagtg tttgattatc catttctttt tgttccaatt   45720
tctgtatctg aaaacaata ttggcttcaa aaacgaacaa aaaaaattt aacttccccc     45780 agattgcaga tttaccatgt aaatgtgttt ccaccctgtt ttcaagctaa tgtgacaaat   45840
ttgctacatt ataagaaca gaaacctgtg tacagattt  ggggatagca cacataaaat    45900
agtccaagga cattatcaac tcaggtgcag aagttcttgc tgaagttcta ttaacaattg   45960
tgtttaaaaa caccagatgg gagcagattt aaagagggag attctaatgg aaggttagtt   46020
gggatttgta gggaagagag agaaggattt taattgaaaa gatactagac cgtattctta   46080
```

```
cctttatagc gttgtcttct tttctttctt ttcttttttt ttgagtcata ttttcgttct    46140
tgtcacccag gctagagtgc agtggtgtga tctcggctca ctgcaacctc agcctcccga    46200
gtagctggaa ttacaggccc ctgccaccat gcccagctca tttttgtatt ttcagtagag    46260
atggggtttt gccatgttgg ccaggctggt ctcgaactcc tgacttcaag tgagctactg    46320
gccttggtct tctcaaaggt tgggattaca ggtgtgagcc acctcgcctg gcctatagta    46380
gtgttttttt ttcttttctt ttctttttt cttgagacgg agtcttgcta tgttgtccag     46440
gctggagtgc agtggcacaa tcttggctta ctgcaacctc tgcctcctg gttcaagcaa     46500
ttctgctgtc tcagtgagta gctgagatta caggtgcgaa ccaccacatc cgggtaatgt    46560
ttgtatttt agtggagacg gggtttcgcc atgctggcca ggctgatctc taactcctga    46620
tgtcaggtgc tccgcctgcc tcagcctctg aaagtgctgg gattgcaggc gtgaactact    46680
gtgcccagcc tagtagtatt ttctatccaa gttttggatg taattctctt gggattttt     46740
tcctaatttg tacagctacc actgtactgt tcatgactgt atccatggga acataagtag    46800
gatgacataa gtttataact tgttgctagg cagatctagc ttgtaatgta ttaagatttt    46860
cccattaaaa agcatttgga tggttttctt ttgtgcggtg aaggtaacta acagcgtaa     46920
tttggaatta aaactgtgaa gttgtataaa ttccttctag gagaaccaac tactctttgt    46980
tttctttctt tctttttttt tttttttttt gagacaagat ctctttttgt cacccaggct    47040
ggactacagt gacatgatca ggtttcactg cagcctggac ctcctggaca caaatgatcc    47100
tcctacctca gccttctcct cccctttacc agctcctccc cttcccttcc ccagctctcc    47160
ccctccagta gctgggaata catgtatgca tcagcatgtc tggctaatta atttattttt    47220
taatttttat ttatttattt atttatttat ttatttattt atttatttat ttatttattg    47280
agatggagtc tcgctctgtt gtccaggctg gagtgcaatg gcgtgatctt ggctctttgt    47340
atcttcctcc tcctgggttc aagagattct cctgcctcag cctccctagt agctgggatt    47400
acaggcacct gccattatgc ctggctgatt tttgtagttt tgtggagatg cagtttcacc    47460
atgttggccg ggctggtctt gaactcccag cctcagaaga tctgcccacc tcagcctccc    47520
aaagtgctgg ggttacaggt gtgacactga gctcagccta ttcattcatt cattcattca    47580
ttcattcatt catgagacgg agtctcgctc tgtccccagg ctggagtgca atggcatgac    47640
ctcggctcac tgcaacctcc gcctcctggg ttcaagtgat tctctgcctc agcctcatga    47700
gcagctggga ttacaggcat ctgccaccac acccggctaa ttttgtgttt ttagtagaga    47760
tggcgtttca ccatgttagt caggctggtc ttgaattccc aacctcaggt gatccgcctg    47820
cctcagcttc ccagagtgct gggatgacag gcgtgagccg ccacacccag ccatatatat    47880
atgtatttt tatttgagtt tgcgttttgc cgtgttgccc aggctggtct tgaactccgg    47940
aatttcagat cgcccacctc agcctcctaa agtgctggga ccgctgtgc ccagcctagt     48000
catgttttta attaattgaa tgtctgaaat ggaagataat gagttaaaat aattgtgtct    48060
taagcctgtc ctcttcagct aaaacagtca gtatttagat atgtatgaac gagatgtgaa    48120
cacttgatcc atcctaaagt acatagcaga tttcaagatg atgacaggta tcttgggtag    48180
ttcttccgac tctcaaagac ttggtggact aaccaagaaa acctcatgga gatcgagaca    48240
cctgtcttgt attttggttg caattttta aaattaattt ttaaaaaatg taatattagt     48300
gtaaaataac taaatttcaa aaaagtttag aatgagatgt aattgaggtc acatagctct    48360
tttctgcaga ggctatcaca cttaacacct tatctgattg taatttaaag aatttttga    48420
ggctggacac gttggctcac gcctgtaatt ccagcatttt gggagactga ggtaggaggg    48480
```

```
acacttgagc ccagcctggg caacatagtg aaaccccgtc ttacagaaaa ttaaaaaatt   48540
agctggctgt cgtagtgtgc acctctggtt ccaggtactt tggagtctga agtgggagga   48600
tcacttgagc cagggaggtt gaggctgcag tgaactgcca ttgcactcca gcctgggtga   48660
cagagcaaga tccctgtctc agaagaaaaa cagaaagag gctgggtgtg gtggctcacg    48720
cctgtaatcc cagcactttg ggaggctgag gcaggtggat cacgaggtca ggagatcgag   48780
accgtcctgg ccaacatgtt gaaaccccat ctctactaaa aatacaaaaa aaattagctg   48840
ggcttggtgg cgcgtgcctg tggtcccagc tacttggaag ctgaggcaa gagaattgct    48900 tgaacccgga aggtggaggt tgcagtgacc cgaaattgca ccactgcact ccagccttgc   48960
ggcagagtga gactcggcct taaaaaaaaa gaaaaccaga aaagaattat gtaagcagtt   49020
attcaataat aaataatatt tatgcagctg ggcacagtgg ttcacacctg tagtcctagc   49080
acttttggag gctgaggcgg gtggatcact tgagcccagg agttcgggac caacctgggc   49140
aacatggcaa aaccccatct ctacaaaaag tacaaaaatt agccggttat ggtggtgttc   49200
tcctttagtc ccagctattc aggaagctga ggtgggcgga tcacttgtgc ccaggaggtt   49260
gaggctgcag tgagccaaga tgtcgccact gcactccagt cccaacaaca gagtgagacc   49320
ctgtctcaat taaaaaaaaa ataataatat ttatgccgtt tttttgtacc agctactatg   49380
ataggtgctt tataggacaa tttggggaag taattgctgt taactccatt ttactcatat   49440
aaggaaagtg acgcttgcac aaggtttaat atttcttgcc cactaacatg tatgcttcaa   49500
gaaagcaggg gctatgtgtt acttctgtct agcccctcc tgtatctagc atagtttctt    49560
tggggtttgg gtagtgtgtc aaatacagtg gaaaggctgg ttttacaaag atgattgttg   49620
tatcttcatt tattacctt gaacttgtag cttcataggg aaatcatggg aatttgagca    49680
gcactgaatc tgcatgtatt aaaaaaactt gcatcatttc tggatttcat gtggtgaata   49740
tttgatagta cctctcgtga tttgataagg tccattattt ggggacaagg gtggttaaca   49800
tagggattga tggaattgtg actccattct gttgtggcgt gtttagtttt tacctctttc   49860
cctttactcc tcgtgcccca gctgcgtctg tgtccattgt cctttcagtt tcttactcta   49920
attgaaagaa tacataggta agaaggaat ctgatagaag gaataaactt ctttgacggt    49980
attaacaagt gtctgatctt gattagtgta agttgtattc agtgcctcat gtttcttacc   50040
tttgaattgt agaaaataaa attttagatc tggttaagat tcttgagatt atttggcagg   50100
aggaaattga agcgcagttc agttccatag aatgttgttg aatgcgtttc ttcatttgtt   50160
aagagtgata atatttgtct catagggttg atacaaggag gaagagatac tctttataaa   50220
aaagtcttag gccgatttga tgataatact aatagttaaa cttgttcaga agttaatctg   50280
ggctgggcat ggtggctcac acctgtaatt tcagcacttt gggaggcaga ggtgggaagg   50340
atcgcttgag cccagaaatt ccagaccagc ctgggcaaca agtgagacc tcgtctctat    50400 aaaaattata aaaataagcc gggtatggtg gcacatgcct atggtcccag gtactcggga   50460
tgctgagatg gaaggatcac atgagcccag gaagtcgagg ctgtggtgag ctatgatcat   50520
tgccactgca ctccagccta ggtgacagag tgagaccctg tctattaaaa aaagttagtc   50580
tgtgttagca tagtatcggc agaaaagtat tctgacacag tataggaggg atcagggtat   50640
gggggaatga gtcaggaagg ccattttaaa gattttacag tgtcctaaac ttgatagtga   50700
aggctaagca ttgaaaatgg aagagattgg ctgggcgcag tggctcacgc ctgtaatccc   50760
tgcactttgg gaggccgagg cgggcagatc acgaggtcag gagatcaaga ccatcctggc   50820
```

```
taacacggtg aaaccctgtc tctactaaaa acacaaaaaa ttagccgggc gtggtggcgg   50880
gtgcctgtag tcccagctac ttggcaggct gaggcaggag aatggcgtga acccgggagg   50940
cggagcttgc acagtgagcc cagatcatgc cactgcactc cagcctgggc gacagagcga   51000
gactccgtct caaaaaaaag aggaatggaa gagattagaa aagatgtgaa caaaccttat   51060
agagcttcca ggaaaggaag aaaggtaaaa acattgagat ttggaatgtt gagtaatggg   51120
atagtataaa cagtatagca gtatagagat gtcactaatg ttttagaaac tgaaataata   51180
gattaatgca tggtaattac cttgccagaa ctgaaaagcg gtggtagtga tgctggagga   51240
agcagattgc tgctgcagaa ctgcagcaag gcctaggagg tggaggcacc aggtatcttc   51300
agaggcccag gtgtggtgtg gttggcccta agctgatggg ctgactgaaa gtctccagga   51360
attcttcctg tctctagatt atgcttcatt ccagcagtcc aggaattaga ctttccctag   51420
cctagcacaa gacaagttta cttttggtag agtttgaacc agagctgtac cctagacttg   51480
aaatggggag gacgggtgga aactatctgg acgtggtggg ggagacgtat ctatgaagtg   51540
aaagtttgta tattgaatgg tcattccaga attcttaata gcctggctta tactctccag   51600
caaattagaa ggttcttctt tgggagaaaa ctggcccaga tgctaacaat tgagtgttac   51660
cctgtattcc agttattacc gcctaacaac tgttgctgtt actattgtct ttaaacaaca   51720
acaatcgttt tattatctca cactttctgg tgatgaggat ttaggaagac atcagttggg   51780
cagctctggc ttgggtttct ctgacttaag ttgtgttcac atggtggctg agctgaaca   51840
gtagggtgct gaagtggcct tggctggcca gacagctttc ttcctggtgt ctcagcatgg   51900
gctgatttgt gctcctcaca acattatggc ctctgactgc ttacaagaaa gtgcaggctt   51960
ccaaagcaag tatcgcaaga aaactgacta ttaactgatt cacttttcat gacccagcct   52020
cggaagtcac ataggctcct ttccgatgta gtcacaagtc tagtcagctt caagggcagg   52080
gaacatagat tccatctctt ggtaggagta cagaagtgga attgcagtca gagtgtaagg   52140
ggtccctgtg ggatgacatg agaaacattc tgtgaccacc tttggaaaac acaatctacc   52200
acattttctc atttggtcac aataattcac attcctcctt cttgtcactt gtgctcacac   52260
cctctcccat cacatcgctc cccttcctg ctatggcatt aacttcaagt tcagcatctt   52320
gtcacctgaa tcaagcccag ttgtggccac ccaaagctcc tcaggtgtgg ttcctctaga   52380
gctgaactca tgtgacgtca agagaaggaa tctgttgctt cctctgactt aaaatggcag   52440
gacaagctta ggataattgc tgtagacaca tctgcccaga aaagaggaaa caggaggcac   52500
agtagtttct catccattgc cattctgaaa ttcagcaggg cacacgttac caattccttg   52560
atttggtctc agttctggtg cctgggaatg attgtttcag gctctggttt ctgctgagaa   52620
ttttgttttg tcttctgagt tacccttttc cctaagaaat ggctgatttt tatagctgag   52680
tagttttctt agcctttgtg ctttcggtag ttttggagga acaaaaaaac cttcccctca   52740
ttttgtactg tttttgtctc tttcagtcca aactggtata attcctttga aaattttgtg   52800
ggctctctct gtgtcaattt gtaacctact acattagaca ggaaccacac ttagcctgtt   52860
tgtggtaggt ccttcatttc cttgggctcc ttgtgtgtca ccagccttag tattcttaga   52920
agccctgttg tttgatggag aggatcttaa aatccttaga aggctcttgg tctcttggaa   52980
aggacagtgc agaaccttct tagatctttt tgaggtttta agaaagtatt acagtcacag   53040
tctgggtttg ttcttttacca ctgagaattt tgagaattgt ttctttttttt aaaattctgc   53100
ctggaaatat ccttaggtag atcatggagt ttattaggtg catttcctgt tttccacatt   53160
tctaaaggcc acattttcca ctacttagac aacagggac ccttttcctg taatgtacaa   53220
```

```
tagtagtttt catagtttct attaagcttt tcctgatagt ttccttgttg aggcccttca   53280
ggcttttgct gatagcctct taaaggcctt gcaatttcca cctgccaccc agccccaaag   53340
ccagtagcac agttctgggt ttttgttgca gcatctcact tccaggtgcc aaaatctgtt   53400
ccttagtctt gctgcctgaa aaatgacccc caaaagttag tgacttaaaa taattccgtg   53460
atttctgtag gtcaggaatt taggaagagc ttgattgggc aattgtgcct caggttcttg   53520
ctttggctgc agtcagatgg tagagctgaa gagtagtgca caggcaaggc agtgtgcaca   53580
gctggagagg gccgagctga gccgcctcca caaggtctct gtgtgaattt gtttgtgctg   53640
cttcttcagg gcactcagac tgcccacata gctttgtgtc caaatgtatg tcctgtggga   53700
ggatgagcag aatctgtatt acctttatg atgacttagt cttggaagtt acatcacatc   53760
atttctgctc tagtcaacaa cttgcctggg gttctagggg aggaaaacag acctcatatc   53820
ttagtgtcag ttggccacac tgtaagaagg tgatatgggg tgggagataa tgtgatcagc   53880
tctagaaaaa tgtaatccac catagctctt agtgaaacag ttacatccct gtctgatcac   53940
cttgcagggg agtcttgcca ttaataagca ccagctgtgt acgtgacatt aaaacttact   54000
ttttagtact tccttcttaa ctgtgactta acagtcaagg attatcaggc acatgaagaa   54060
aaagccataa cagtctaaca cagacagata aaaagaaacc aagtgaagaa ataggaaata   54120
caggttgcat aagaaaagct caaatttgaa aaaacaaaaa agcttgaaga gctaagagaa   54180
aatgcatgac ataaaagcaa gaaggtataa agtaggggtc cattcagaga acaagaaaga   54240
gctcttggaa aataggattg caggacaaat tttcaatagg aaaccaagga aatcttccag   54300
aaagtagtag gcaaagacag acaaaaagag aaagacaatg cctgattggc ttcttgactg   54360
aaacatattt aggtgggaag aggaagtgtg gaaatgtgaa taaggactgt atactaatga   54420
taatgaatta atattaattt ttgcttaagt gtgataatag cactgtggtt ataggagaga   54480
atgcccttag gctagaaga tgcatactaa aggaactgtc atgatatttg cattttcag   54540 atggttgtgt gcacacacgt gcgctcacac acagtgggag agggagggag aagggagagc   54600
ggttatgtac aagagagaca actaaagcaa ttatgatata atattagtaa ttgatgatga   54660
atacaaaaac aaaacagaag ggaatacttt agagttaatg gattggttca ggagctccaa   54720
catctgcact gttagatgtt ctagagagag aaaagataat tgagaggaaa caatattaaa   54780
tcaacacatt aaaaatgttc agaactgaaa atcacaaatc tccacattga gcagacccac   54840
tgagtgccca gcgcagggaa taaagaaaa aatagattgg tacatcacac tgagatttca   54900
gaacactgag aatagagaag atctcaaaat cctccagtgg aaacaagtca agttacagca   54960
gtggactgag aatctgtatg acactagaat ctaggtgaca gtggagcagt gtcctcagaa   55020
ttctaggagc atacccatct aggatttttt tttcttcttt tttgagatgg agtctcgctc   55080
tttcgctggg ctggaatgcg gtggtgtgat ctcggctcac tgcaccctcc gcctcctggg   55140
ttcaaccagt tctcctgcct cagcctccca gtagctggg gttacaggtg tggaccacca   55200
tgcttggcta atttttttgta tttttagtag agacgggtt tccccaccat gctggccagg   55260
ctggtcttga actcctgacc tcatgatctg gccacccag cctcccaaag tgctgggatt   55320
acaggcgtga gccactgcac ctggcccaat ttaggattct atgccaaact gtagtatgaa   55380
cataaagaca tctttatttt tatttattta ttttatttat tttgagacg gagtctccat   55440 ctgtcgccct ggctgggcc cagtggcaag atctccactc attgcagcct ccgcctccg   55500 gattcaggga gttatcctgc ctcagcctcc taagtagttg ggactacaga cgcgtgccac   55560
```

```
cacacctggt taattttttgt attttttagta gagacggagt tttgccatgt tgaccaggct    55620
gatctcaaac ttctgacctc aagtgagccg cctaccttgt gctcccaaag tgctgagatc    55680
acaggcatat accaccatgc tcggcctatt attttttaatt tgatggtcat attattccag    55740
atttggccaa tgggatttcc ttcaagctga ctcctgtgtc cttttgacaa atatctataa    55800
tcctttattt attttttattt ttttgagaca gagtcctgtt ctgtcaccca agctggaatg    55860
tagtggcgtg atctcgcctc actgcaaccc ccgcctcccg ggttcagaca attctcctgc    55920
ctcagccttt ggagtagctg agatcacagg catgcgccac cacacctggc taattttttgt    55980 attttttagta gagacggggt ttcaccatgt tcggcgaggct ggtcttgaac tcttgatctc    56040
aggtgatctg cctgccttgg cctcccgaag tgctgggatt acaggcatga gccattgcac    56100
ctagccctct ataatccttt aaatgcttgt ttatggtatc ttagaatatt tcaaatttat    56160
cttgtatgtt ctctgcctca tcctggagtc aactgtttgt ctaaggagga gccattctct    56220
tgaagtggag aatagtatta tagaaaccaa tatcttggca ctagctgtat ttattgctgc    56280
caggatattg ttgttttcag ccctcttagt gggcagaaca agtagatcta tgtgtattta    56340
tttattagac atatttattg tctatatctc tgcctacaca tatatataac catgaatttt    56400
accacaaatg ccaccatttt gatccaacat cataggattc attttagccc ttttcctttc    56460
cttatttgta gctctcgtct ctgacagtga aatcttggt tctcatcctt aatatagtta    56520
ctcatttgct taatctccct gaaagcttgg cccagacatg gaatccagca aaggataagg    56580
tgaagggaat tcttaaagag aaatcttggg ataatagctg tgtaggcatt caccagttag    56640
tccagattgg tgagtgaaga cagggctcca aagggggtgtt gtcaagaaat aaacaaccaa    56700
tagatagcct gatgtgttga gacttacaca tgtagtagaa gtttggaggt gaattagtga    56760
tacatataca gaaaaccaaa caagcaaaaa aaacaaaaaa aaaatagaat tattaattcc    56820
aggtaaaaaa atcacacata atcacaccac tgaactctgg cctgggtgac agagtgagac    56880
cctgtctctt aacaaacata aattaaaaat caggtaaaac aaattgtaca agaatggact    56940
tacaacaaca gaatgcaaca ggattcagct atgaatagta tttactagtc ataaactacg    57000
agagtgccat aacactgaac ttagggagca atttaggaa taaactgaga aaaaagtac    57060 acaggggcct taggacctaa gcagctagtg tgatatcact tgtggatgtt tagtatgcat    57120
tttgggtacc agccccttt gaacactgtc tttgagggga aattgtccac tccacagtag    57180
aagctattaa tatgtttttcc catcctctct tgtagtttgt catagatgtg tgacttctat    57240
tccatgcacc agggcaagac taggattagg aagcaagtga tgtgaagtag acaagcatgg    57300
ctgccaggtt tcagaggcag cgtttttctag cggtggtgtc cactatgcac tgccaagtgt    57360
ccttgtgttt aacacctgca gcagttaaga cctccactga agcagttctg tggggtaatt    57420
ctggtgttgt cctagttgca tggcttgtaa atctggtttg atgaccttcc tgtagagcca    57480
tttagttgct tatattagct agaatgggct ttgtttactg taaaaaatct ggttgacgaa    57540
attggcatta ggaatgatcc tcaagaaaat gaattggtta tctaacttgg ttgtgtatga    57600
aggcagtgaa gaaaggtgag agcttaaaga atcatagtgg ccttgggccg ggcgcggtgg    57660
ctcacacctg taatcccagc actttgggag gccgagatgg gcggatcacg aggtcaggag    57720
atgagaccat cctggctaac atggtgaaac cccgtctcta ctaaaaatac aaaaagttag    57780
ccgggtgagg tggcgggcac ctgtagtccc agctactcag gaggctgagg caggagaatg    57840
gtgtgaacct gggaggtgca gcttgcaggg agccgagatc gcaccactgc actccagcct    57900
gggcgacaga gcgagactcc accgcaaaaa aaaaaaaaaa aagaatcata gtggccatgg    57960
```

-continued

```
gcatggtggc tggtgcccat aatcctggca ctttgggagg ctgaggtggg agaatcactt    58020
gaggtcagga attagaggcc tgcagtgagt gccactgcac ttcagcctga gggacagagc    58080
acagagcaag atcctgcttc aataaatgga tggatgggtg ggtgggtggg tggtggatg    58140 gaggaatcat agtgatcagc agtgcttaat gactgagatt agtctattct gaagtatgtt    58200
aataaagctt gaaggatcag aggaagagag taggaaaaaa gcacacacat tctacaaacc    58260
tcgccacatc cactcagtta aaagacagaa caggattccc ttggatgttg ggaaagggaa    58320
gtcagacgtg aaagttgtag acaggattaa gccacttaat tttcctatta aatggactct    58380
agagagtaag ttcatgcttc tcattttact gatggagaag cagtaccaca tacttggtga    58440
aattcctgtg tctgcaaaac attggttatt ctgcaattgt tatatataaa gggataaaca    58500
ttgaagttat tggtctcttc cttctcattg gtattgtggg tgttctttac caactgagtt    58560
aggaactgac ttgagatatt ttaaacttac gggacttgat ttagagcact tactcttaga    58620
tgttaaatat ttggtttgct ctttattgaa taacttaatt atcttattac taataattcc    58680
tgtattagac aatgagactt agactcataa tagaatacag gtatcttaat gagaatgttc    58740
tcatttaaaa cactaactcc taattcacta gcagctaata aaactaacat tgttgcacag    58800
tacattgttg actagttaga agaatttgac agtatgtttg gtgctgagac cagctcggtc    58860
ggggagaccc taacccagcg cgctagagg aattaaagac acacacacac aaatatagag    58920
gtgtgaagtg ggaaatcagg ggtctcacag ccttcagagc tgagtattgc tattaataaa    58980
gggtgtagaa tttgaaaata ggccaggcgt ggtggcccac gcctgtaatc ccagcacttt    59040
aggaggccga ggaaggcgga tcatgaggtc aggaggttga gatgagcctg accaacacag    59100
tgaaaccccg tctctactaa aaatacaaaa attagctggg cgtggtggcg ggtgcctgta    59160
atcccagctg ctcaggaggt tgaggcagga gaattgcttg aacctggaag gcagaggttg    59220
cagtgagccg agattgcgcc actgcactct agcctgggca acagagtgag actccatctc    59280
aaaaaaaaaa aagaaaaaga aaaagaatt tgaaaatagc ttgagagact agagaagaag    59340
tgaactgatt tattttatat ttatgtatct tattttttgg cttgttgacc agaagtgaat    59400
tgatatgaat aagcacactt gcaaaataaa tgggttattt atttatttat agagacaggg    59460
tcttgctttg tttcccaggc tagagtacag tggcaccatc atagctcact actgctgctg    59520
gcaacttctg ggctcaacgg gtcctcctgt cttgacctcc caaagtgctg ggattatagg    59580
catgagccgt catgcctggc ccctaatta tttagatagc cctgtagacc tgatttcttg    59640
tggctgaagg tctctcaaat tgattctcag taggcttcat aaataaaagg gaacttacac    59700
tggaggatct ttatgctgaa ttggcttaga ataagtagaa attgctagga atgttttatt    59760
tttgtttatt taatttgcta aatctgcttt agatatgagc cttgtaactg gatttcttaa    59820
aagtgtcctt atgattgaat ctatttgtgg tgttttggatt gattatttta agttcctact    59880
atgtaccaga cgtttgctac ttgttttaac ttgctgttta atctctttga agaaggaact    59940
gtttcctcca tttttataga agagaaaatt gaaacttaaa gagattagag aactctcctt    60000
cagtctaggc agagctggga ttccatttca ggactgttat gctacaccaa ataaatgctt    60060
gctgcgttaa agaatgactt aacagtgaac accttaagtc ttcattgccc agttacgtga    60120
atggaagaaa ggctgagcag tgaattacaa acactctctc ctctagtctt ctggcagtgt    60180
tcctttacct aattctgtgt cctcaaacgc cctgttttct ttaggtgatt atattatttg    60240
tttcttttaa gcttgcctgt ctgcttgttc ttctgaacag ttcccttcaa atgttacacc    60300
```

```
atccacccac atctgtattt cagtatttta ttgtgtcctt tcattgagac tctaatttgg    60360
gtgaaaattc tccaaactac atttcttttt agcatattct attttttgtca cctagaatca   60420
gcctcccagc tgacttttcc ccatagatac gtaacaacca cctgctttaa cattttctat    60480
cttccactta acaaaaatat tactgttgat aaataatgaa tacttagcat gtataactgt    60540
gcaaataaaa tgggaggaat gtgtatcggg aagatttgag gggagtgtgg ataaaaaact    60600
gtttgaaaat accagctgtt gaattttata gtgttactct ttttattttt atttttagt     60660
tttattatta ctattttttg agatggagtt tcgctttgtc gccaggctgg agtgcagtga    60720
cgtgatcttg gctcactgca acctctatct cctgggttca gcgattctc ctgcctcagc     60780
ctcccgagta gctggaacta gaggcgcgcg ccagccaatt tttgtatttt tagtagagac    60840
agggtttcac catgttggca aggatgatct cgatctcttg acctcatgat cttcctgcct    60900
cggcctccca aagtgctggg attacaggcg tgagctactg cacccagcct attattattt    60960
tttaattgag acttgtctta ctttcaccca ggctggagtg tagtggtgca atcttgcctc    61020
actggagcct ccgcctcctg ggctcaatcg atcctcccac ctcagcctcc tgagtagctg    61080
ggaccacagg cactgctac cgtgcccagc taatttttc tattttggt agagacaggg      61140
ttttgccacg ttgtccaggc tggcctcggc ttcccaaagc gttgggatta caggcatgag    61200
ccaccacgtg cagcctatag tgttattctt tagtagttcc taaaaggctt gtgttagatg    61260
tttatagctg atagttgtgg tttgaatctg tgtccccagc caaatcttgt gtcgaattgt    61320
catccccagt gttggaggtg ggggcccatg attggatcat gggggtggat atcccccttg    61380
gtgctatttt catgatagtg agtgagctct cgggcgatcg ggtcgtctaa aagtgtgtag    61440
cacctccctc ttgtctctct tgctcctcct ctggccatgt tatatgtgct tgctttccct    61500
ttgccttcca ccatgattat aagtttactg aggcctccct agaagctgag cagatgccag    61560
catcatgctt cctgtacagc ctgcagaacc ttgagccatt gaaacctctt ctctttataa    61620
attacctagt ctcatctcag gtatttcctt cttttctttct ttctttcttt ctttcttct    61680
ttctttcttt ctttctttct ttctttcttt cttttttttt tttttttttt tgagacggag   61740
tctggctctg tcgcccaggc cggagtgcag tggtgcgatc tccactcact gcaagctctg    61800
cctcccgggt tcacgccatt ctcctgcctc agcctcccga gtagctggga ctacaggtgc    61860
ctgccaccac gcctggctaa ttttttgtat tttagtaga gacagggttt caccgtgtta    61920
gccaggatgg tttcgaactc ctgacctcag gtgatctgcc cgcctcagcc tcccaaagtg    61980
tcgggattac aggtctgagc cattgcgccc ggccaggtat ttttttatag cagtgtgaga   62040
acagactaat acaatagcca tcatgtaaaa tacagtttcc attttgagcc aggcacttgg    62100
gtaaaaatga agagtaggta aaagacaaga tgtagttcta atttgagctt gtcatttagt    62160
atttgagtaa tgccgcataa tggctgtggg tttccgatga cacacacctt tcatgatgt     62220
gggtggccta gggagtagtg tgtttgttgg aaccacagtt ctctgcagag ggaatatgat    62280
taagtctgat ctttgtaatt tagaattaat gaggccaggc gcactagctg acacctgtaa    62340
taccagcact ttgagaggcg aagatgggga ggatcacttg agcctgagtt tgagaccagc    62400
ctgggcaaga tagtgagaac ctgtctctac aagaaaataa agaaaaaaat ttttaaaaaa    62460
agaaaaaaaa tatagaattg gtatcttggc cacacctctt tccctgtggt tgagtttttt    62520
tttttttttt ttttcctgtt cttttccttt tttttgaga caagatctct tcgtcaccta    62580
ggctggagtg cagtgacatg atcaaggctt gctgcagtgt cagtcctg ggcttaaagg      62640
atcctcctgt ctcagtctcc caagtagctg ggactggagg taggtgacac tagcctggct    62700
```

-continued

| | |
|---|---|
| cactttaaaa acatttttg tagagataag gtcttgccat gttgcccagg gtggtctcaa | 62760 |
| actcctggcc tcaagccatc ctccctcctc agcctcccaa agtgctgggg tctctggcat | 62820 |
| tcaccaccgc ggacaacctt tttttttttt tttttttttt tttaagctaa attttgttga | 62880 |
| atatttggat aggcaataca ggcatatggt acaaaattaa aagatgcaaa agggttatgc | 62940 |
| acaagagaag tacatttctt aggcattcct ggccttccat tttcccttcc tggaggcagt | 63000 |
| tttctgattt attttctaca aggattctgt ttaaatactg gagaatatct gacctgttgt | 63060 |
| actttacttt agaatggcag gaagctgaat gactcatggg catttttccc tttgtgaagc | 63120 |
| tcattgacat tccttcctct caataaccta actatggcat gttttataat ttgcttttgt | 63180 |
| ttttgcttta tcacagtatt ttcctatgtt ttttatagtc ttaattttta agcactgctt | 63240 |
| taggtatcta ttaatagttc agaaagttgc gaagattaca agctcatatt tgtgaaagtg | 63300 |
| tctggcacat aataggtgat caataaatat ttccttctag cttgtctgtc ccctatctcc | 63360 |
| cactggttgt atgtatgaaa caaaaaaatg aaggagaagg ctgagcatag tggctcatac | 63420 |
| ctgtaatcct agcactttgg gaggctgagg cgagcgaatt gcctgaggtc aggagttaaa | 63480 |
| gaccagcctg gccaacatgg tgaaacccccg tctctactaa aaatacaaaa attagccggg | 63540 |
| tgtggtcaca ggcgtctgta atcccagcta ctcaggaggc tgaggcaaga gaattccttg | 63600 |
| aacctgggag gtggaggttg cggtcagtcg agatcgcgcc actgcactcc agcctgggca | 63660 |
| acagagtgag acttttttgtc acacacacac acacacacac acacacacac acacgtga | 63720 |
| aataaaccta tgaaccaact aatgcagtgg attccaaaat taagattaag cttgtgtaag | 63780 |
| ttgtaatgtt tcttgatgta cccatttatt tgagtggaaa cagattcttt tcattctttg | 63840 |
| aaatcacttt gctgagattt ttttattttt ttttatttttt ttttggagac agagtctcgc | 63900 |
| tgtgtcgccc agactggagt gcagtggtgt gatctaggct cactgcaacc tccacctccc | 63960 |
| gggttcaagc gattctcctg cctcagcctc ctgagtagct aggattatag gcatgtgcca | 64020 |
| ccacactcag ctaattttgg tatttcagta gaggtagggt ttcaccatgt aggccaggct | 64080 |
| ggtctcaaac tcctgacctc aagcgatccg cctgctcagc ctccctgagt attgggatta | 64140 |
| taggtgtgag ccacggtgtc ccgccaagct gagacatttt taagaaaatg tttctgtttt | 64200 |
| tttgtttatt tgtttgtttt gagatggagt ctcactctgt cacccaggct ggagtgcagt | 64260 |
| ggtgccatca ctgcaaccctc tgcctcctgg gttcaagcaa ttctcctgtt ccagcctcct | 64320 |
| aggtaactgg gactgcaggc ttgccaccat atacctggct gattttttgt atttttagta | 64380 |
| gagatggggt tttaccatgt tggccaggct ggtcttgaac ttctgactca gcgatctac | 64440 |
| ccacctcagc ctcccaaagt gctgggatta ctcccacagc acctgctcag aaaggtttc | 64500 |
| ttttctttc tttttttttt tgagatcagg tctcactctg tcgcccaggg tgtagtgcag | 64560 |
| tcgcgcaatc tcagctcact gcaacctccg ccttccaggt tcaggtgatt ctcttgcctc | 64620 |
| agcctcccaa gcaggtggga tttcaggcat acaccaccat gcatggctca tttttgtatt | 64680 |
| tttagtagag aggggtttca ccatgttggc caggatggtc gcgaactcct gacctcatgt | 64740 |
| gatccacccg catcagcctc ccaaagtgct gggattataa gcgtgaatca ctgcacctgg | 64800 |
| ctagaaacat cttctaaagc ctaatctttt tttttttttcc ttatataatt taggttgact | 64860 |
| atgtaaaccc aaaacacata gggtagaaac tcgtgaaaaa tatttttgag gatatctttg | 64920 |
| caaagtgttg tgcctcacgg tgctggatat ggatgtgtgc ttagtgtcag tgcatagatt | 64980 |
| taggatttcc cacctgtatg tatgcttttg gtgagtcctt ttaggcgata tgtcctcatg | 65040 |

```
ttcaaggagt aatggcatac tggttcattt aaacccatgt tttaatccta atttaagacc   65100
gatttacttc ttcttggagc taatttctta acttttctga tgatgttttt gttgcttaag   65160
ttaagactaa tataacacag aagtcttact catccttttt gatattagag attttggttt   65220
attaatctag tggaatttta aatatcattt tacatgttta ctctcaagat ctgatgattg   65280
actgactggg tgcagtggat cacacctgta atctcagcac tttgggaggc caaggcgggc   65340
agatcacttg aggtcaggag ttcgagacca gcctggctaa catggtgaaa ccctgtctgt   65400
agtaaaaata caaaaattag ccggacttgg tggtgcgtgc ctgtaatccc agctactggg   65460
gagacagagg tgagagaatc acttgaaccc cagaggcgga ggttgcagtg agcctagatc   65520
actccattgc actccagcct gggcgacaga gtgagactcc gtctcaaaaa aaaaaaaaa   65580 aaaaagaag attgaattaa gggcaaactt ggaacaggcc agtttcccat tatattgcct   65640
ctctgaaaca agtgaaagag ttttctttat gagggtgtt cttttttaatt taatttaatt   65700 aatttttatt tatttatttt gagacagagt cttgctctgt tgcccaggct ggagtgcagt   65760
ggcatgatct cggctcactg taacctctgc ctcccaggtt caggtgattc tcctgcctca   65820
gcctcccaag taattgggat tacagatgcc caccgccaca cccagctaat ttttgtattt   65880
ttagtggaga cggggtttca ccatattggt gaggctggtc ttgacctctg aacctcagat   65940
gatctaccca cctcggcttc ccaaagtgtt ggggttacag gtgtgagcca ctgtgctggg   66000
ccttcttttt aaaaaaggtt tttctggcca ggtgcggtgg ctttaatcca tatgtgtgag   66060
accaggcacg gtggctcatg cctgtaatcc cagcactttg ggaggcagat cacctgaggc   66120
atgagaagtg cttgaactag ggaggtaaga agttgcagtg agccaagatc acaccattgc   66180
actccaggct gggtgagagt gagactctga aaaaataat aataaaaatg gttttcttac   66240
ttttatgact tgaattatgg aaagttttta gaatgtgact ctttttctcag gaacaggatg   66300 gctacctacc taccccccat cctttttcctg tatgctatgg attatcagac ccctcacttg   66360
ggttcctctt acatcaccaa ggtgtgcttg tcaatacccca gaaaccaaca ctgatacatt   66420
actaagttcc acatttttatt tagattccaa tagttttccc attaatgtcc atttctgttc   66480
tagaatccaa tccaggttac tgtatgcatt gcatttaatt atgatgtctc cccagtttgc   66540 tgttttttcac atgactagac tagggttatg aatttgggga attcatatga ttggagtggt   66600
gggaggtgta gtgcatgcta ctccatgatt tattgctggt aatgttaatc gtggccaagg   66660
ttgtttccct actgtataca ctcaccacct tccatactta ttttttttgga aacaagttag   66720 taagtccaac ctacactcaa gtcggggaga tttaagctcc atctcctaga ggggagtggg   66780
gaatatttac ataaattatt tgaaattctc ccacgaggaa gctgcttttt ctaggaaagg   66840
tctttgcccg ttattctacc gacttactgg acttttttatt tgactttta aaaagaagct   66900 ctttagataa aatctccata aatacttaga taaattactg caatttttata tttgcatatg   66960 aacaagtgga gttttgttga tgcagggttg cattggcctt cactatcaaa caaatgtct   67020 catctgatca gcatttataa atagtgaggt accagaatca ttaaggctca taaagtcttc   67080 cgttttttatt ttggctattc tggtggtggg taacaatatt aacaacaata aaaattcatc   67140 ttatttact ggagattcct gcaaagtggc agaataccag gacaaggaac caattctggc   67200
acacatgtgt caaacaagaa agctctggga atgtaataat gtaataaagt gtggtcgaga   67260
gagctctggg ctggaatagg catgggtcc ttgacactat cacctctgcc aagacacttc   67320
atgtgtatgg tttccccacc tttaagtaaa ctctatttat gaagttcttt gtagctttaa   67380
tagtttctag agttgcttga atttgggtg acttcttgca agggtaatgt gaagtagtgt   67440
```

```
cacatggaca gtaacggaga ggtatctgct gctgccattt atataataaa tctgaatttg   67500
gaggcagaga aaggaggcag aaagtttggt aaggacgtta ttgcaacctg aataagccac   67560
ttagggccta gatcagtgtt tgggaatgtg ggagaagaca gccatagtca agaagcgtga   67620
agtagttaat gttgagttat ttttaggtgg ttttttctgtt cttttttactc cagacactga   67680 cttttcgtaat aagataaata atctggtgag tcgcatgctc atggtgtgct gaggcattta   67740
gccaagcagc ttatgcatgt attatctcat ttaattctgt cactatgagg tagagattat   67800
ctttaaccat tggttccaaa tgagaaagcc ctgtttgaaa taattttttcc agtgtattta   67860 aattttgtag gtacacacct agaatttcaa actgatggtc tgagttctga gcccatctgt   67920
ttaattcatc ctaatgggtt atcttgtgga tatgctgatt atagtaaaac aactttaaga   67980
atgtgatata cattatgagt gatacttgtg gtttgaatgg gttttttttaa acaacatgaa   68040 aatttgaaga tattttgcat agatttgctt tgggtaaaa cttttttttt tttcatatct   68100
tctgtaatta acttctttcc cccctttttt gagatggggt ctcattctgt cacccaggct   68160
ggagtgcagc ttgatgtatg atcatggctt actgcagcct tggactcctg ggctccagca   68220
atcctcccac cttagcctcc caagtagctg gaagtacagg agtgcaacac catgccctgt   68280
agagacggag tcttgctgtg tttcctaggc tgatctctaa ctcctggctt caagtggttc   68340
tccctacttg gcctcccaca gtttgattag agatgtgaac cactgtgccc agccaaaatt   68400
aactttttaa tctattctaa atcaagaaga aaatagatgt gtcttttctg ggactagtaa   68460
tgagaaattg acagcatctg gttttttggct gttgttaaag tgtgattatt actatactgg   68520
tatgctgata aagagattgc atggtaattt tcatcctttc atctaaaaac ataatattat   68580
aaggatagat atttccttag tatggggtga cttgtgtaga ttactatctc ataaattggt   68640
tcagattagt ttttaaaaag ggcaaaattg tatattagtg atattgctca gctcttttttc   68700 aaagggataa agcactgtaa agagagaatg tgggggtaga agtctaataa aatcctcaca   68760
aatctggatc agtaacagaa aagtcagtta taggccaggt gccatggctc atgcttgtaa   68820
tcccagcact gtgggaagct gaggcaggtg gattgcttga gcccaggaat tcgagaccag   68880
cctgggcagc atggtgaaac cctgtctgta ctaaaaatac aaaaaattag ctgggcgtga   68940
tggtgggtac ctgtagtcct agctacttgg gagtccaagg tgggaggatt gcctcaaccc   69000
aggaggcgca ggttgcagtg agtcgagatt gtgccgctgc actccagcct gggcaacagg   69060
gtgagaactt gtctcaaaaa agaaagaaag aaaagtcact tataattatg tgggctttaa   69120
aaaacctgac tgatagtgct ctgttttttag tttcaccaaa agataggtag tacttccatc   69180 ctcttttcatg aaactacagt atgtctattc tcaatgtttc aaaaccttgt aagactcaga   69240
gggaagaaat agtttctcat taagaaaaat ttagtcaaca gtataattat gtattaagtg   69300
cttcaggaaa agcaatgggg gaaagtattt cctacagtat taggtctctc attagaggtg   69360
agcagaggga gttccttcag cgcaggacgg gcatttctgc aggtgaagtg ggatgagaca   69420
accggctata gcaagatgtt agcatatgta gttagcttat ggaaacataa tttgaattgg   69480
acatgagttt ttgtttgttt ttgaggcaga gtcttgctct gttgcccagg ctctattgca   69540
atggcacgat catggctcac tgcagccttg aactcttgga ctcaaggagt tcacccacct   69600
cagcaaccca agtagctgga actacaggtg tgagccacaa tgccttgcta atttttttttt   69660 ttatttttttg tagtgacagg gtctcacttt gttgcccagg ctggtctcaa attcctgacc   69720
tcaagcaatc ctccagcctt ggcctctcaa agtgctggga ttataggcgt gagcactgtg   69780
```

```
ccctgcctat gagttgttat agactgggtg attttgtagt aggcagcagt ttgttgtcat    69840
ttgcatgttg tacttcatgt atggttttcc caagtcatta aatgtacata cttctgcaac    69900 ttttttatttt ttattttttc tggtgaaaag atatacatat atttagaatt agccagctgg    69960
actcagttta gatgaccccca attttgttgg caacatccaa agcatcataa tcaggagcta    70020
gttgaacgta tgcctccttc tctccatcag gccgaatcag ggtgttgacc gggccacatc    70080
aatgtcatag agcttcttca cagcctgttt gatctggtgc ctgttggctt taacatctac    70140
aatgaacaca agtgtcttgt tgtcctcgct cttcttcatg gcagactcag tggtcagcgg    70200
caacttgatg ataatatggt ggtcaagctt gtttctcctg gcggcgctct tctgaggata    70260
tttgggctgc ccctggagtc gcagtgtttt gggccgctgg aaggtgggtg atgtgtggat    70320
cttttttttt tccggctgtg gacgccttc aacactgctt tcttggcctt cacagccttt    70380
gctttggctt cggcttgagg aggggcagga gcttccttct ttgctttcgg tgccatcttg    70440 tgaaagggc tctgcagctt ttaatgtgta cagtttccat gatatgattg taccagatta    70500
taagattatg ttggacattt gagttctttc caatttattg ctgttttcag cagcacttga    70560
tgaataactt tgtagataag ttttttgcaaa gctttatgaa tattttcttt tgggataaat    70620
tgctagaggc tcgggtaaac attgccaaac taccctttcag aaagcctgaa cttatttaca    70680
gtacacttat ggtatggttt ggctctgtgt ccccacgcaa atctcatctt gtagctccta    70740
taactcccac atattgtagg agggacctgg tggtagataa ttgaatcatg aggccagatc    70800
tttcctgtgc ttttctcttg ctagcaaatg agtctcatga gatatctaat agttttaaaa    70860 agggatttt ccctgcacaa gtgctcctct ctgcctgctg ccatccacgt aagactgagt    70920
tgctcctcct tgccgtccgc catgactgtg aggcttcccc agctgcatgg aactgttaaa    70980
tccagttaaa cctctttgtt ttgtaaattg cccagtctct ggtatgtctt tatcagcatt    71040
gtgaaaacag actaatgcaa cttctctcaa catttctagt ggacaggttt tctatgttcc    71100
cttctaacat cctgttttgc caaacttttg caaagaattt catattgtct tttttcctaa    71160 ttcaacctttt tgtaaggaac tcttacaaca ttggtgtaaa ggtatgtcct tagctggtgg    71220
tacagtagtt agaagttttc tctgggttat ggtgatattg ggagtaattg tgttatagga    71280
taatctgggc tctctgtatt tcataagatt gtggtgcctc accatcagtc agactgtagc    71340
ttcagggctt ttttttctct tggattgctt ggtggtgaaa tatcaataca gccttgccca    71400
ttctgattag tgtgttacat tactgatagg gcagtgttaa gagaaatagg agaaacctga    71460
gcctaaaaca tttcactgtg aaattaattg gtctctgaag tgtttttgtct ttgtttaggt    71520 ttgacgatcg tatgtggcga aattacattg gtggtaaatg ataagcttgt tatattgata    71580
acatggaaga aaagtgtttc tggtttctct tagagaaaat cgattcccag tccaaggcac    71640
ctgtgagtcc aagagaatga gagaaggtaa gatgttatta gttagaaact gactatacaa    71700
ttccagtttc tagtgcagag ttgacttcag tagcatttga ttagcatcta acttccttct    71760
tgggggaatc agaaaaggga catagattag gcattagctg aactcagatt actggaaagt    71820
gattgagtca gttctatttt ttattttttat tttttgagac agtctcactc cgtcacccgc    71880
tggagtgcag tggtgcagtc ttggctcatg tcaacctccg cctcctgggt tcaagtgatt    71940
ctcatccctc agcctctcta gtagctgaa ttgcaggtgt gagccaccac gcccagctgg    72000
gtttggtttt ttttgcattt ttagtagagc caggttttca ccatgttgtc caggctgttc    72060
ttgaaatctt gacctcaaat cgtctacccg cctgagcctc ccaaagtgct gggattacag    72120
gtatgagcca ccatgcctgg ctttgagcca gttctaaggg aaattattca tttatttttg    72180
```

```
tcagcttgta atattgcaaa tcatagtatt tttgaaataa ccttcccatg ggaatagagt    72240
ttatgccctt aaagggtaga gtgctattat aaagagagat acaagaagag agggagtggg    72300
tggcattcca gagatcaggt ctacatgagt tgctgcccag ccttcttggt tctcaaactt    72360
gtcggtctgg attgctgtgt ttaaggaaag ggaatagaac aatatactcc ctttctaaaa    72420
tttttcatta attggctacc taacctatgt tatgcatatt aatttactta acatttatga    72480
agtacttata atatgctaga cactgaagat actatggtct gaaagatggc aaataataga    72540
ggagaaagaa aatcataatt gctattattt atgaagtatt aagtacaggc agttcttaag    72600
cattcgactt agtatttttc aactttaaga tggtacaaaa gtgatacaca ctcagtagaa    72660
actgtatttt gaattttgat cttttcctcg gctagcaata tgtggtgtaa tacccttaca    72720
tgagatattc aaccctttt ttttgttgtt ttttggagac agagttttgc tcttgttgcc    72780
cgggctggaa tgcagtggcg caatctcact gcaacctctg cctcccgggt tcaagcgatt    72840
cttctgcctc agcctcccga gtagctggga ttacaggcat gcaccaccat gcctgactaa    72900
ttctgtgttt ttagtagaga tagagtttct ccatgttggt caggctggtc tcaaactcct    72960
gacctctggt gatccaccca cctcagcctc ccaaagtact gggattatag gtatgagcca    73020
ccacacctgg cctcaacact ttttttttt ttttttttaa ataaaatagg ctttgttaga    73080
tggccttgcc caactacagg ctaatgtaag tgttctgagc atgtttaagg taggctaggc    73140
tatgatgccc attaggttag gtgtattaag tgcattttg gattacaata ttttcaattt    73200
gtgatacatt tatcaggact aacactgttg taagctgagg agcatctgta tgtaccaggt    73260
acttaatatt aagtggcct ttctaattct catagaaacc catgcaaggt aggcattatc    73320
ctctccattt ttctttaggg ttagtgaagc taagtagctt gttcgtcatc actcaataac    73380
aaagtggtta aaatgggata caagtccacc atgggattga gtcccagatg ggagttcaga    73440
tgctgaccag tgttaggatc taagtgcaag tcacttaact cctcttttca aatgtggact    73500
acaacagttc ttatctcata gggctttttt ggtgtgtgtt atgtgacaga taggtgaagt    73560
ggttagccca gttactggca cgtagtaata gttaataatt atattagatc atactggctc    73620
aaaagccatt aatagtagtt actgctggta gttgagtctt acaaagccat tgttttctcc    73680
acatgtcttt atgcaaatca ttaatgacaa gagcctaaac tgtgatagag aaggtgtccc    73740
cagtgttatg agagtattga agaggaatgg actgctaacc tggactagga gagtaagcag    73800
acttacaaag atggtgatcc ttgaggggtc ttgaagcatt attaggagtt agctggtggg    73860
aaaagataaa gagaaggaag tgggttagag gaaagtcatg gcaaagcaaa aaggcccaga    73920
aatgtaatga ctgtgtgagg gatagagtcc tgagggtgag acataggtta gaaagataag    73980
caggccagat tatgaagggt cttgcatgcc atgggttttt tccctaaaga cagcggggga    74040
agcagcagaa ggacttttta ttttggaata attttagatt tacaggaaag ttgtaaagat    74100
agtacaaaga gtttccatat accctacacc cagtttcccc gttattaaca tcttacatta    74160
gtatggtaca tttgttacaa ttagtgattg attgatttgt aattattacc tgaagttcat    74220
aatttattct tatgttctta gtttttacct aatacccctt ttctgttcca gaatcccatc    74280
gaagatacca cattacattt agttgccttg ttgctttagg ttcctcttgg ctgtgacagt    74340
ttctcaagat ttttcttgtt tttgatgatg ttttagtttt aagaagtact aatcagaaat    74400
tttgcaggat gtttctcaat tgggatttgt ctggcatttt tctcattatt gtactaaggt    74460
tatgagtttg gggtaggaag accacagacg tagagtgcca tttcatccca tccaagggta    74520
```

```
cataccatca acatgactga tgactgctca tgttgaccag tgttgcctgg cggagtactt   74580
tacagtggaa acgtctgagt ttgtcagaag tttcagctgt aaagtactct tccatctcct   74640
gctccgcccc tttccataca acccccttttt ttggaaagag gtcactatgc acagcccaca   74700
ctgaagggga agggagttat gatccatatc tcaggaagga cttttaacgt ggaaagtgat   74760
ttgatcagaa ttatgttcca gggccaggca cggtggctca tgcccataat tccagcactt   74820
tgggagggga ggcaggagga tcagttgagc ccaggagttt gaggctgcgg tgagctatgg   74880
tcatatcact gcactccatc ctggacaaac agggcaagac cttgtttctt aaaaaaataa   74940
agaatgggct gggcgtagtg gctcacacct gtaatcccag cactttggga ggccaaggca   75000
ggtggatcaa gtgaggtcag gagttcgaga ccagcctggc caacatggtg aaaccccatc   75060
tcggctgtgg tatatgaaaa ctagccgtgc gtggtggtgg gtgcctgtaa tcccagctgc   75120
tcgggaggct gaaggaggag aattgcttga acccaggaga tggaggttgc agtgagctga   75180
catggtacca ctgtgctcca gccttggcaa tagagtgaga ctctgtgtgg ataataataa   75240
taataatgat aataataaaa aataatgaat tgtgcttcag aaagattgct ctagctagtg   75300
gagaaactga atctggggag accgaattta gcctgcaacc tttaagacag gacaagatga   75360
gaaaccatga agttggaaac tgaaggtcag tggcagcagg gttggagagc gatggatttg   75420
agaaaagtcg aagagattag tggatggggc tcagtgggtt ttgcagagtg tgtgtgctcg   75480
agtgctagta gcagatgagg ggactccaag atgacttgcc agccatattg ctgggagttg   75540
gtgactatac aagtgatagt gttaattttt ttaggtaaac aagaagaaac agcttgttgt   75600
tgatagtggg aagggtgaat gagagggcaa taagctgtgt caagatgctt tttgagttgt   75660
tcttggctta tatgcgtatt ctgtcttgag ataaagattt agaagtcatt accataataa   75720
atgtggtttg agaaatttgc agtgttagat gttatggcat aggaagagta attaatacca   75780
gatgaaaaag aggaacccag ggaacactga tgtttaaaaa agtggtagag aaaacgtggg   75840
gaaaggtcaa cttttgttaa aatctcttat tcatgtggct gtttaattcc tctacatcac   75900
atcctctctt ctgttcaccc tggaggtgta aaacactata ccaaaggaca gaacacacta   75960
tacacgttta gaacatttct tctgaggata gttactgctg cggtaatgca ggtactgttg   76020
tggtgatgct aatgagaata aatcttgcta aaattaagaa tcaagacagc tgaagaccta   76080
tggaaagcaa ttgaccgaac agtactactt caggtcaggt aagcagtggc agtacaagaa   76140
tgaagaatgg attctttgtt accaagcaat taacaatcta gttgggtatt tactgggtaa   76200
tacaatacaa agtaagcaat ggtaattggt tatgtgtatg tcagttgtgg catgatagtt   76260
tctacctcgg ctatctgctg aagccctttc tgtctgtctt ctctccctgt ccagctttgt   76320
tcttgcctgc ctttttattt tttacagtcc ctctcctttt ttgcagggg gcgggcggt   76380 gctagtggga gtatacatac ccctcgttaa ccacctgtga tgtaagttaa gattttttt   76440 taaatgtttc tgttttttaa aaacaagtga atagagcatt tattatcatg gaggataaaa   76500
tcctcaaaga aaaatctgt ttagctttta aattcttcgt gaaatcgcta atctttgagg   76560
cgaaaaattt tttcccgtaa atttaggaga acatgagatt tgagttttta aggactttat   76620
agcgtgccta tgtttattgt agattttaat tccagagagc tggtgattgg aaatcatgga   76680
cctatttgtt ccaatttaaa ctttcagcat ttaaaaagga agagataaga gagaaccaga   76740
caggaggtat atagtttgta gaaagataca gatatttaat gtaatcccag cactttgaga   76800
ggctgaagcg ggcagatcac ctgaagtcgg gagtttgaga ccagcctgac caacatggag   76860
aaaccctgtc tctactaaaa atacaaaatt agccaggcgt ggtggcacat tcctgtaatc   76920
```

```
ctatctactt gggatgctga ggcaggagaa tcgcttgaac ccaggaggcg gaggttgcag    76980
tgagctgaga tcgcgccact gcactccagc ctaggcaaca agagtgaaac tcggtctgaa    77040
aaaaaaaaaa aagagaaaag aaaagataca ggtattgaaa taccaaagtt gcttctgact    77100
tcctcatttt atagagagtg aactgttgtc agttgagaat tcttaagcca tttaacttaa    77160
atgctaaaat acttaatgtg gatatcatgg ggaggaaaaa tgttctttac attctttggt    77220
ttttgatcat aatgtatggt gtctttaaaa tctaggcatt gtagcataat ggttaacacc    77280
accgactctg tcttctgctg ttttcatacc tcttccttaa gcttcgactc agcttcactg    77340
ctcataggtg tgatgttggg cagcttactt catctctctg tgctttaatt ttctcatcta    77400
taaaatggat agtcgtaaga ttgaaatgaa ctaaggcacg tcaaagtaca cagtgcctag    77460
cacatagtaa gcatttataa ctgttacagc aatagtaatc atatatactc ttgccattcc    77520
ctttgatttc tatcttttg attacccaac gtcagaagcc aaaaattttg gagtcataaa    77580
acgttttttg gtccctaaca taattaagtt aaatttactc atgcgtagca tctcaggata    77640
tattgaaagt atgggtggcc agtccataca tttaagaata agaattataa gaatttagag    77700
acagagcctt gctttgtacc ccaggctgga gtgcagtggt gtgacctcag ctcactgcaa    77760
cctctgcctc ctgggttcaa gcaattctcc ggcctcagcc tcctgagtag ctgggattac    77820
aggtgtgtgc caccatgccc gactaatttt tatatttta gtagagacgg ggtttcacca    77880
tgttggacag gctggtctca aactcttgac agcaagtgat ctgcctgcct tggcctctcc    77940
caaagtgctg gggttacagg catgagccac ttcacccggc cagaatttac ctttttaaaa    78000
agctttattt attatctttt tgagtcctac tgatgagtaa tttggagttt catgtgtcct    78060
ttttatatag gtattagagt atgacaatga catctataat gggatagaat ttaaatttta    78120
aagcaaacca aacagctgtc ctatttatga gtgctaactt aaagatggtt tgataacatg    78180
aaggtaacgg tactatgaat gtgaatgtaa tgaccctata tatacacaat aaatatacac    78240
aatatatata cagttctctg tttatacttt tcagcttcag ttttcttgtt ctgaatttaa    78300
gcaagaaggt agcatttaat tcatagctta ttgtgctact cctgttttca tacctcttcc    78360
ttaagcttct ggtaaaatta aaacatttca agtagagttt aggattgtag aaaacaaggc    78420
atgttgttaa aacctgtaat tgtgagcgtg tcttaaaatg acaagattat tatatatata    78480
tatatattta tttattttac ttatttattg attgattttg agatggagtc ttgctcttgt    78540
cgcccaggct ggagtgcagc ggtgttgtct cagttcactg caacctctgc ctcccgggtt    78600
caagcaattc tagtgcctca gcctcccaag tagctgggat tacaggcacc tgccaccatg    78660
cctggctaat ttttgtattt ttagtagaga tggggtttca ccatgttggc caggctggtc    78720
ttgaactcct gacctcaggt gatccaccca tcttggcctc ccaaagtgct gggattgcag    78780
gtgtgagcca ccgcacccag ccctatctta taattattga tagcaagaaa agcatattca    78840
ccatttgttt cagttctcat tgttttcgct tccccttctg tgtttatcca tttggccatt    78900
ctctttcttg tgttcatctt tctgttctga ctcaggtcat tgaggatatg gttggaccct    78960
gaatggtaga aacacaactc cctcttcccc tcgactccac agacttaatg tgattttta    79020 gggtataggg gaggggtta tgagaatgtg ggaacccaag caggtgttct aatggctgtg    79080
gagtaacctg tcttctcctt ccagttagtt tctgtgtttt gtttgtttgt tgttttaaa    79140 gagacagggt ctctccctct gtcgcccagg ctggagtgca gcaggtgat catagctcac    79200 tacagccttg aactcttggg ctcaagcaat cctttagcct caccctctga agtagctggg    79260
```

-continued

```
actacaggtg cttaccacca tatctggcta acttttaaaa actttcagag atagggtctc    79320
actgtgttgc ccaggctggc cttgaacttc tggcctcagc tgatcctccc acctcagcct    79380
cctgagtagc cttgcttttt aaataacagc tttactacaa taaaattaac aaaacacgca    79440
gttcacttat ttaaaatatg caaaattcag tggttttcgg tatattcaga gttgtgtaac    79500
tatcaccaca aatcaaattt aaaacatttt atcatcccat gaagaaatgc tgtacctgtt    79560
agcagtggca ccctgttatt tcaaatgccc tacagcctct ggcaatcact aatcatcttt    79620
ctgtctggac ggttcatgta aataaaatca tacaataggc tgtggatttt tgtgcatgtg    79680
actggctgct ttcacttagc atagtgtttc aagtttcata ctgagcatgt gttagtgttt    79740
tattttcatg gcagtataaa gttctgtcat atagacatac tgcatttttt tattcaatcg    79800
gttgatgggc atttgggttg tttctacctt ttagctgttg agtaatgctg ctatgaaaat    79860
ttatatacaa attattatgt ggatatatgt ttttatttct ttgggctgta tacctaggag    79920
tggattttct gggttatatg ataatttttt ttctttttg agatggagtc tcgctctgtt     79980
gcccagtctg gagtgcagtg gtgcgatctc ggctcactgc aagctccacc tcctgttacg    80040
ccatttcct gccttagcct cccgagtagc tgggactaca ggcgcccgcc accacaccca     80100
gctaattttt ttttgtattt ttagtagaga cggggtttca ccatgttagc caggatggtc    80160
tccatctcct gacctcatga tccgcccgcc tcggcttccc aaagtgctgg gattacaggt    80220
gtgagccacc acgcccggcc tctgggttat atgataatct tttgaggaat ggcaccattt    80280
tatattccca acatttttagc caaataatct gactaaaaac aggcaaaaga ctgaataga    80340
catttctcca gggaagatac tcagatggcc aataaactta tccaatatgc tcaacctctt    80400
tattcaggga aatgcaaatc aaaaccacag tgagagacta cttcacacct gctggctaga    80460
atcaaaaagt cagataataa caagtgttgg tgaggatgtg tagaaattgg aactctcata    80520
ccctgctggt gggaatgtaa atgtaaattg ctgttctgct cccaaacagt tgacaagtaa    80580
aatatagcat tatagagtga gaaataactc agagtttcag agtagaactg aaaatatact    80640
agaagagtat tttccttagt gttggactag atgattttaa atttgaacac agacattgta    80700
tcaggtaaca tcaaatcata cagtgaaggg tttctcacaa tgtacacaaa atagtatttg    80760
tctgcttaac actgggatt tgcaaagaaca gtgaaatatt acagtgttac aaagcaagat    80820
cttcctctct ttaaatgcct gttaacctga ttttaagaat atctttattg tatacatctt    80880
attctttaaa tgtaccccat aactaatagt accaattta tgttttcaac atttaagtta      80940
tgatattata catttccttt aacttgcttt ttctattcaa actggttgat agctgtagat    81000
ctgattttgt tttctatatt taattcccctt gaagtcacat accacggttt atccaatccc    81060
tgatttttt tttttttttt tttaagacag agtctccctc tgtggcccag gctggagtgc    81120
actggcagga tctcggctca ctgcaagctc cgtctcctgg gttcacgtca ttctcctgcc    81180
tcagcctcct gagtagctgg gactacagtc gcccactacc atgcccggct aattttttgta   81240
ttttttagtag agacgggggtt tcactgtgtt agccaggatg gtctcgatct cctgaccttg    81300
tgatccgccc gccttggcct cccaaagtgc tgggattaca ggcgtgagcc atggctcacg    81360
tgagacagag tttcactctt tttgcccagg ctagagtgca atggcacgat ctcggctcac    81420
cgcaacctcc gcctcccggg ttcaagtgat tctcctgcct cagcctccca gtagctggg    81480
attacaggca tgtgccacca tgcctggcta atgttgtgtt tttagtagag acagggtttc    81540
tccatgttgc tcaggctggt ctcgaactcc gacttcagg tgatccgccc gccgccgcct      81600
cgccaagtgc tgggattaca ggggtgagcc accgcgccca gccccgttg atgtatttta     81660
```

```
aagattttcc tctatttttg tcctatagac gattctgtag taactatcta tgttattatg    81720
tagatagggt tcttcagata aacagaacta ctagaatatg tatgggtgta tctatgtgta    81780
catatattca gagatttatt ttaaggaatt ggtttatgta gttgtagggg cctgacgagt    81840
ctgaaatctg tgcaggccta taagaaggag ttagggcctt agtctcaact tctggaaaaa    81900
tctcaatttc tgctcttatg acctttaggt gaactggata aggcccaccc acattatgga    81960
gggtaatcaa gagattatag atgttaacca tatctactaa atactttcca cagtaacacc    82020
tagattaatg tttgattaaa taactggcta ctagagtcta gccaagttga cacagaaaac    82080
taagcaacac actgtccttc catgtgcacc agagactttc agactttaaa aaacctccac    82140
caatagttta tacacatact taatgaaacc atatgctgat gttttctgtt cttattcttt    82200
tttttaaaat gctgattagg aacccaaaat tcaatgtgag tagatctgac cagcaatttg    82260
aaaaacattg catatatatg tagtctagaa atggaattgc tggcttgcaa ggtatccaca    82320
cgtccacttt actatacatt gccagttttt ttctctgaag tagttgaacc actgtacagc    82380
cctactagcc gtgtgaataa accttctttc ttaccccctt gatggcaact ggtaattgca    82440
gtttccttgt agacctaatt attccagata ggtctgggct tattttttaa ggtctttaaa    82500
acttgataaa aatcgacttt aggccgggca cggtggctca tgcctgtaat cccagcactt    82560
tgggaggccg aggcgggcgg atcatgagac catcctggct aacacggtga aaccctgtct    82620
ctactaaaaa tacaaaaaat tagcagggcg tggtggcagg cgcctgtagt cccagctaca    82680
ggctggggca ggagaatgac atgaacccgg gaggcggagc ttgcagtgag ccaagatctg    82740
cactctagcc tgggcgacag agcaagactc cacctcaaaa aaaaaaaaa aaaaaaaaa    82800 gtcaacttta aacaaagaga cctgcctgtg ttggcaccett cagcaaatat tagtatctac    82860
ccagaaatta atgacatttc tttatttttca ttgtatttat attttttgat ttacatatag    82920
caaaactgaa taattttggg tgcacatttt tgtgagtgtt aagacatgta tacaatactc    82980
ctcccttatc catgaaaggt atgtttcaag acctctggtg gatgcctgaa actgtgggta    83040
gtactgaacc ctatatatat actatggttc ttcctatgca tacataccta tgataaagat    83100
taatttataa gttagacaca ctgagagatc aacaacaaaa aataataaaa tgaacaatta    83160
taacaatatg ccaacatcgc caatactttg gggctgttag taagtaaaat acaggggact    83220
tgaacacaaa tgctgcgatg ctatgacagt ccagctgata actaagatga cccaagtgac    83280
taatgggcac atagcaccta cagaggggat gtggtgcaca aatggatgat tcaggtacta    83340
ttcctggaat tttcatttga atgttttcag accacagttg atcatgggta actgaaatca    83400
cagaaagcaa attccaatgc ggggcaccac tggagtttca tataccacca ccacaattag    83460
gataccaaag agttccagct cctccaaaag ctacctcaga ctttcttaag cttcctcaca    83520
cttctagacc ctgaaaacct tggatctatt cattatccct gtacttttgc cttttttcaga    83580 gtgtcgtatg aatgaacttg tactggcttc tttcactcac tgtaatgctt tggaagtagg    83640
tctaggttgt tgaatatatt agtagttcac tattttgtt gctgtgtact gttccagtat    83700
atggatgtac tacagttggt ttatccattt acgcattgaa aacatctgaa tatttcacag    83760 ttttttttt tttttttccc caaggcagaa gaatttttct tagtacagaa caaaatgaaa    83820
agtctcccat gtctacttct atccacacag acccggcaac catccgatt ctcaattttt    83880 tccccaccct tcccgccttt ctattccaca aaaccgccat tgtcatcatg gcccatcccc    83940
aatgagccgc tgggcacacc tcccagacgg ggtcgtggcc gggcagaggg gctcctcgct    84000
```

```
tcccagtagg ggcggccggg cagaagcgcc cctcacctcc cggatgggc ggctggccgg    84060 gcgggggct gaccccccca ccaccctccc ggacggggcg gctggccggg cagaggggct    84120
cctcacttcc cagtagggc ggccaggcag aggcgcccct cacctcccgg acggggcggc    84180
cggccgggcg gggggctgac ccccccccca cctccctccc ggacggggtg gctgccggc    84240 ggagacgctc ctcacttccc agacggggtg gctgccggac ggagggctc ctcacttctc    84300 agacggggcg gttgccaggc agagggtttc ctcacttctc agacggggcg gccgggcaga    84360
gacgctcctc acctcccaga cagggttgcg gcccagcaga ggcgctcctc acatcccaga    84420
cagggcggcg gggcagaggt gctccccaca tctcagacga tgggcggccg ggcagagacg    84480
ctcctcactt cctagatggg atggcggcgg ggaagaggcg ctcctcgctt cctagatggg    84540
atggcggccg gcagagacg ctcctcactt tccagactgg gcagccaggc agagaggctc    84600
ctcatatccc agacgatggg gggccaggca gagacgctcc tcacttccca gacggggtgg    84660
cggctgggca gaggctgcaa tctcggcact ttgggggcc aaggcaggcg gctgggaggt    84720
ggaggttgta gcgagctgag atcacgccac tgcactccag cctgggcacc attgagcact    84780
gagtgaacga gactccgtct gcaatcccgg cacctcggga ggccgaggct ggcggatcac    84840
tcgcggttag gagctggaga ccagcccggc caacacagca aaaccccgtc tccaccaaaa    84900
aaaaaaacga aaaccagtca ggcgtggcgg cgcgcgcctg caatcgcagg cactcggcag    84960
gctgaggcag gagaatcagg cagggaggtt gcagtgagcc gagatggcag cagtaccgtc    85020
cagctttggc tcggcatcag agggagaccg tggaaggaga ccgtggagag agagggagac    85080
gagagggaga gggagaggga gagctgtttc acagttttg atgattgtga ataacgctgc    85140
ctatgtgtgc aggtgctttt ttttgtttgt ttgttttgag gtggtgtctc gctctgtcgc    85200
ccaggctgga gtgcagtggc gcgatcttgg ctcactgcaa gctccgcctc ctgggttcaa    85260
gccattctcc tgcctcagcc tcctgagtag ctgggtctgc aggcacacac caccacacct    85320
ggctaatttt tgtattttg tggagatggg gtttcacagt attggtcagg ctggtctcga    85380 accctgacc tcaggtgatc ctgagcctcc caaagtgctg ggattacagg cgtgagtcac    85440
tgctcccagc ctgtgtgcag gttttattgt gaacatatgc taattctgta gggtatatgg    85500
ctgaacagtg gggttgctag atcagtcatt tggtaaatat aattatgtct ttgtaaaaaa    85560
ctgcaaaact ttcccagaat ggctttataa ttttgcattt acaccagcag tgtatgagaa    85620
tttcagttgt tcccattctt gtcagcactt tgtagtgttg atgcctttta ttttagacag    85680
cctaacaggt aaataatggt ttctcatcat ggctttaatt tacattttcc taatggctaa    85740
tgatgtagag catcttttca tctaatatac cccctttata tctactttgg cgaagtgact    85800
gttcaaatct tttggccatt ttaaaaaaat tgtgttattt tccttattgt tgactttgaa    85860
agttctttat gtattctgga tagaagtcct ttgttgcata tgcgatatgc aaatattttc    85920
ttacagtccg tagtgtatct caacagtgcc ttttgcagag caaaagtttt taatttttat    85980
ttttagtata ccattaaaaa atgtttggtg gattgtgatt ttggtactgt atctaagatc    86040
tcctttccca atccaaggtc aaaagattt ccatgtgttt ttctttagaa attctataat    86100
ttttcagttt tacacttagt tctgtcatct gttttgagat aattttgagg tatggatcca    86160
aattttttta aaaaatgtt tgttttgttt ttgcatgtga atattcattt gttcctgcat    86220
catttgttga aaagattatt attttggct tgattttgcc ttcgtgcctt tatggaaaat    86280
catttgatcc tgtatgtgtg gttctgtttt tggactctat tccatttatt tccctttttt    86340 tttcttttt tttttgaga cagaatctcg ctctgtcacc caggctggag tgcagtggtg    86400
```

```
caatcttggc tcactgcaag ctccgcctct cgcgttcacg ccattctcct gcctcagtct   86460
cccgagtagc tgggactaca ggcgcccgcc accacgcccg gctaattttt tgtattttta   86520
gtatagacgg ggtttcatca tgttagccag gatggtcttg atcccctgac ttcatgatcc   86580
tcctgcctcg gcctcccaaa gtgctgggat tacaggcgtg agccactgca cctggccttt   86640
tctctgtctt tatgccaata ccatacattc ttgattactg attttttgta attagtcttg   86700
atttagatag tgtaagtctt ccaactttgc tcttttcaa aattgcattg gctgtctcat    86760
ttactttgcc tttctttatg aattgtagaa tatttatcaa ttacggcaaa agaaggtgct   86820
acaattttga ttggagttgc attgaatctt tagagcagtt tgggaagaat gccttcttaa   86880
taataagtct atatctatga tctatttctt catcttctta gatcatcttt agtttctctc   86940
agcagtgttt tgtagttttc agtgtacaca tcttacttta tccctaagtt atttcatatt   87000
tgatgctaat gatctttaat tttgattttt gatttttttt ttattgctgg tatatagaaa   87060
tagaattgac tatttactat taatattatt tcctacaacc ttactaaact tgtttattct   87120
ggtaccattt tgtagattct acaaaatgta gattttctac acagataatc gtgcagtttt   87180
gattgtacct ttccactgtg gatgccttta tttttgtttt actttagact tttattggaa   87240
atacagcagg acttatttgt ctttgtattc cctttggggt ccctccccac acatacccttt  87300 gatgactttt gttttagatt ctttgtagcg ttagcattgt tctgaagtca gaactatgta   87360
tatatctata aaaaggtat acttgggctg gcgtggtgg ctcacacctg taatcccagc    87420
actttgggag gccaaggcag gcagatcatg aggtcaggag ttcgagacca gcctggccaa   87480
tatgatgaaa ccccgtctct actaaaaata aaaaattagc tgggtgtggt ggtgcacacc   87540
tgtagtccca gctactcaag aggctgaggc aggagaattg cttgagcctg ggaggcagag   87600
gttgcaggga gccaagatca caccactgca ctccagcctg cgtgactgag tgagactgtc   87660 tcaaaaaga aggtaaactc aaaggcggtc actccatctt ttttgtcata tttcttttctc  87720 atctacatcc tcttcccatc tgcaacagaa attcaacttt taattttacc taattcatac   87780
ttttcacact ttgggtcctt ttcactattc tgttacggtt ctttaaagta actgcctctc   87840 agatttttact aaaaatgtaa aatttcctct ttatgaaacc tagaacacat tggtagacaa   87900
aattaaagat gggagatctg gtggtatcat aaaagaagaa attcgtcaac cagactgtgg   87960
gtttcctaga ttttttgttta tagtaggttg tatgttatat ttagttgcat ttttcccct    88020 agagtttagg ttccataact ttcatcatat tttcagagta atttatttaa aggaaaaaaa   88080
gtggccaaaa ttaaccttta gaatgaataa gtctgggcct aaccagtgtg aaggtatggt   88140
cactgaacct cctgtttctc gagtcttttgc cttctgaaga tatgtgtatt gtaatagatg   88200
acagccgctt gcggttaatt cagtaataca tgtcagctcc accccctggca cttttaaacc   88260 ttttggccta ctattttgca aaacagattt ttaagaatta gtatgcattt tagaagtttc   88320 cttcaggtt aaacttttta aatagttatt ctttaataat gctgttaaaa gaattttggg    88380
atttctattg ccaagtcact aaaaagtaac tcaggcagag aagggtaagg gtgctgcaag   88440
cacacatgaa gaattaacat tttaaaagaa cctttgagca ccttggcacc tgtggatttc   88500
ttcttggatg tctcatgcct aaaagcagag cagcatactg taaaatcagt aaaagtagga   88560
aaggacttgc aagtagaaat gtttcagcag actctcgcct cccccatctc catcctcact   88620
ctgatgttaa gtgtggggcc cattgggcca gatacaggta aaaaggtggg tgatgtcatt   88680
aaaaggtatt gttacttata gcttattata tgtgttaaat tttaataaga attttctttt   88740
```

-continued

```
ttctttctcc caagccaaac tggcaagacg cagtcaagaa cgggacaatc ttggcatgtt    88800
ggtctggtca cccaatcaaa atctgtcaga agcaaagtgt aagtcttgga gcactttatt    88860
ttccaccttt cttgtttaat gtaaggtttt aaaggtacct ttgaaggtaa aagcttctat    88920
atgtattaaa ttctttttct attttaagat aaataattta aagagtttta aagtgtatat    88980
ttctttttt aaaattttt attttttgag atggattctg gctctgttgc ccaggctgga    89040
gtgcagcagc acgatctggg ctcactgcaa tctctgcttc ctgggttcat gtgattctcc    89100
agccccagcc tcctgaatag ctgggattac aggcacccat taccacaccc agctaatttt    89160
tgtattttta gtagagatgg ggttttgcca tgttggccag gctggtctca aactcctgac    89220
ttcaggtgat ccgcctgcca tggcctccca aaatgttggg attacaggtg tgagccactg    89280
cgccctgtga tctgttccat ttttgaacat gttctttctt acagagcact aaaaatctgc    89340
ctccctgtaa tttgtaaaag ctttgttttc ctgaactttg ctaaataagt ttgcttccat    89400
atgtgtcctt taaatgttca gtcatcgtat ctcctttact gtctgagtcc aagctagttg    89460
cttcaggtgc cttttcagat ggttttttg gggatctctt ttcatctcct gttgtccttc    89520
taagtgtgtt ccagttggcc acaatgtcca tcttaaattg tactcagaac tgaatatgaa    89580
gaatactgag cattttttga acctttatgc cagcacagta ctaaaatgtt tttcatactc    89640
ctgtatcatt cagtgttcac agtaacccag gaggaagatt ttttctctgt tttacagatg    89700
gcatcccata gttcaaagag tcagagggtt gtaaaagtag cacagatagt gagtggcgga    89760
accccaagta gttcactcct gggtcataat ctcacttatt tctcaggctg tgttcattta    89820
gcctgttagc cactatcttt ctgttattac agtttaaagt tgtattagtc acttttccta    89880
ttgtattgct tattggagtc tttggagtca gaatttaatt ttaatgttat cttattttc    89940
atagacctag aagaaaaggg cagaatatgt aaagttaatt gattttaaa cagtggtgtt    90000
gcctataaaa taaatttaca gttttattgt aagccctgat tacaatcgtt ttaagtttaa    90060
agttggttaa aactttaaac tttaaaaaaa ctaacctgtc cactgaggct cccagtggac    90120
agcgagctcg gcttgtggct gagacacact tgagccaggc cagaggcata ggaggaccaa    90180
atttgacaga tatcaataca cgattcttac tgaggccttt gaaacggacc cttgtcctgg    90240
aattactgtc agaaaagaac cggccagaaa aacagactcc cgagccacga gtccaggttt    90300
ggtttcagaa ttggagaggt ggagcacgga aaagaagcca gagcagcgcc agcgtggagg    90360
ccacctgggc gcaggtcccc ccgatcccag accctggtca gcctggggtg ctgaccccta    90420
ctgttccacc agcggggctt ccccgggggt cccaagcaat gtgggcaact tctcttggga    90480
atcggaggat gctttgggcc aagctctcct ctggggcgc gctgatgttc cgtgcgcgaa    90540
tgtggccccc gctgacctgg agatggcagc cagtgcgctc ggccacgctt agggagatgt    90600
cccttgatct ccgccctcgg gcccagtgct gcttccgggt ccctcttgcc accagcccct    90660
cccacagctg gaagctggca gtgctgggcc tcaagttcat cccggggcac ccggcctgct    90720
ccccatacac cagtccctag ctctgcgggg gctggggctg caccctcctg ctgtggagca    90780
gcagccgagt ggggctggc agctggggga ggcgcctggg tgcgccgtga cctgggagca    90840
gccctctccg ccccagcccc cgcagctctg accgtatccc gcctctctgc ctctttcctg    90900
gccatagtca cagccacagc catcgcagga cccggctgag cgctaggaac aggttccttg    90960
tcttcctcca gaatccaact cgcacgggag gccccagcac ccctgccccc aacccgctgc    91020
ggagtctgaa cctcaagcgg ctgcatagca aacccgtgga aatgaccgtg cagtgtcagg    91080
cagtggaaga cagatgaact aagcaagggc tcatcggtag tgttcacgtt atgaaaattg    91140
```

```
aagagaaata tcaagattta tttactttgt cacggaaggg cttccagaca tacctttcag   91200
ggaaatcgag ttgttagggt ggaagggcct tggggtgcat gagacctagg ggttttcctt   91260
agatggcata aaaaaggatt gactttatag aatacatctg tctttccatt tattaaccga   91320
gtaaacacgg agcactgaga gtgaacaaag tccactagcg agaaggcagg atgaggacgg   91380
ctttgtagaa atgcattatt ttctatcagg aaagagcaat gatttctact ctgggaaaaa   91440
aacaaaacaa acacttacct aaaagtaata tttacatatt gttgaaagtt catagataaa   91500
agtataaaga ataaaaaaaa ttcacctatt attccatcac ccagaggtga taatcgttaa   91560
acattttggg gtatttcttc caatttttttt tgtatgtatt tatataagtg agatgataga   91620
ttatctgtgt gtgtgtatgt gtgtattgtc ttcctgagca tcggacctaa gcagtttcca   91680
cgttgttaaa actgcttata aaggttttaa ataactaggt gtaatacttt attacatgga   91740
tatgtcagta tgtttaacaa ttactctatt gaaaatttag gtgtctcagt tttggaagaa   91800
tatggaagtc ttggttgtcc agcatttatt ctgacattaa gtagaaataa gtgatttagg   91860
acatatttct agcagatact aaaaaactgt gtataggatg tctggagatc cctggctttt   91920
cttgtgtgtg tgtgtgtgtt ttttttttcc tcttcttttc aaagtggctg ttcagagttc   91980
tgcctcttag ggttactgaa agcttataaa gttatgttgt aattataaaa ataaatgcta   92040
ttttagaaaa ttcaaatagt acataatgca taatatataa ttgttttcca caaaatgtga   92100
actgttatca gtctgctcat aagtacatct gggactttgt ttcatctcag tatatctaca   92160
gttatctaat ttttttttac tgtaactagt atggatgtat cataatttag cctttttttta   92220 aacaaaatta cctgtattac ctattgatga atatttataa tcttagttct tttttttaaac   92280 tctgtttttt aaaaaacctg atccgtagaa tgactctagt ttaacattaa tgaattgtac   92340 atttctttttt tttttttttg agacagaggt ttattcttat tgcccaggct ggagtgcagt   92400
tgtgcgatct tggctcactg caacctccac ctcctgggct caagagagtc tcctgcctca   92460
gcttcccaag tagctgggac tacacacgca ggcccctgca cctggccttg aattgtacat   92520 ttcagaaatag ctagaagagg gctgagtgcg gtgtctcacc cctgtaatcc caacagtttg   92580
agaggctgag gcgagctgat cacttgagct caagagtttg agaccagtct gggcaacatg   92640
gtgaaacccc atgtctctca aaaagtccaa aagttagctg ggtgcgtggc atgtgcctgt   92700
agtcccagca cttggaggca gagatgagga tgcttgagct caggagttca agaccagcct   92760
gggcaacata gatctccccct ctattaaaaa aaacgggga ggcgggggct agaagagaat   92820
aattttgaat gttcctaata tagagaaaat gtaaatattt aggattatgg atatcccagt   92880
taccctgatt tgattatatg aatgtatcaa attatcacat gtaccctgga aatatgtaca   92940
tctgatatgt atcagtaaaa taaaatacat acattttaag agaggatctt ggctctgttg   93000
tccatgctgg agctcagtgg cacagtcata gctcactgca gccttgaact cctgggctca   93060
agctgtcatt ttaaaaaaag caatagtgaa gattttttgcc ccttaataca tttcttattt   93120
tcttgtttaa aatagatttt atattttaga gacattttag cttcacagct aaattgagca   93180
gaaggtacag agtgcccatt tatcttctgc ccccacacac ccacaccctc ccccagtgtg   93240
aacatcctgc gctggagtcc accaaaggga tacgtttgtt acaatcaagc agcctacagt   93300
gacacattct tatcacccga aattcatagt ttacattaag cttcactctt gtgttgtatg   93360
ttctgtggat tccgacaaat gtataatgac ctgtccacca atgtagttat catcgtttca   93420
ctggtttaag aaacctctgt gctccacctg ttcatctccc tctctgcctc ctaaaccctg   93480
```

```
gcaactgttg atcgtttac tgtttctgta gaatgcctc cagctggaat catatagtat     93540
gtagccttt  caaattggct tctttcactt agcaatatgc atttaaggtt ccactgtctc   93600
ttttcatggc tggatagttc atttctttt  agtgctgaat aatataccgt tgtctagcta   93660
tgccacagtt tatctggtgt attgtcatgc taggaaccc  tctcccaccc ccacattaca   93720
aacagactga tgtcttctgt cgtcttctcc tttttacat  cgttgtttca actgaaatta   93780
ttggattata ttttttcctt cacttacatt aaactcatac atactttgtg cctggacttc   93840
attcttttca gtgtacctgg ctctatattt attcttttag gtgaatctta gatttgtggt   93900
aacaagttct gtccaaaagt atctcaattc agattatacg gaattcgtgt ttatctactg   93960
agttttcatt tacgttttat attgaacagc ttttgtctg  ggaatgtacc aggagtgaaa   94020
ggttcaggaa tctcatactg taatggagag acagaaaaaa tgaacatgtg agcaaataat   94080
ttatgtgtag ttttcctagg caactcttcc tttttagagg tagaaacact ggggtctaca   94140
gaagtaaagt caagtgttta aggtcccata gccagttatt acagtagcca agttttagct   94200
agatctcttg tctccagaca atatttacca cacctgtctg cctttgtagg ctgcttcatt   94260
taataaactg taattcaacg cttaaaacat taatactata ctagtttttt tgggctgtgt   94320
ctaagtaaaa cccatttaat gagagatata acttatggga tatgcctaga aaatgtggcc   94380
tgtagagaga catttcatgt tgaggaagcg taaataattc ccaataacat agattagaac   94440
aatgagttta aatattaagt gatcatggaa aattacttga tgaaaccatg gcttgagatt   94500
tcagcaacaa aggagtgaat gaagtacaat ctgccatcat gtgtaatctg agggtggca   94560
gactgagaaa ctgaaaaatg ttcacttatt ggagaagagt acagttgact catatgattt   94620
ttacatcaag catctcccat gtaccactga gtcagtattc tgatgttccc gttgggactc   94680
agcagaaggt gctagctttc ctaggtagaa acaaagagtt gaagatggtt gacatttgat   94740
tgaaatgtgg aagaatgagt aggagtttgc tggctggacc aggggcataa gtgcacacta   94800
gacagaagaa atgatagcat ttcctttttt ttttttttt  tttgagatag aggtctcgct   94860
ctgttgccca tgctggagta cagtggcgtg atcttggctc actgcaacct ctgcctcctg   94920
ggttcaagca gttctcctgc ttcagccctg cgagtagctg ggattacatg cgtgtgccac   94980
cacacccggc taattgtgtg ttttagtag  acagggtt   ttaccatgtt ggccaggctg   95040
gtcttgaact cctgacctca ggtgatcctc ctgccttggt ctcccaaagt gttggaatta   95100
taggcgtgag ccactgcgcc cggccagcat ttttcatttt  aaaggtgtga agatgtggag   95160
aggaaatcca gcacttaatt ttggagattt gcctgactgt gacaagtgtt gtcctgggc   95220
agagagaaat gaaactagaa aggcaggcca gcttcttaaa ggtttggagg atctcttgac   95280
ggagttttag ctagaactga tatgatttac actgaaaagc tcttgacagt cctgtggttt   95340
agagaagagt agagaagagg tttattggtg gtagtaaggt gttgatgcaa ttccaagtca   95400
gagaagttga ttgcctaacc gggtcagtgc tgttaaaagg cggcatgatg gaaattcagg   95460
aagtcaagtc aggagtatct taacttgccc caaagagatg gagaccatag aattgtgggc   95520
ttagtgactg gttcaggcag cctttaacat gcctgtaaag actattaaat gccgttaagt   95580
ataggtgcac tgttccatca tttactccac acgtttctgt tgaacccta  tgaggcactc   95640
cgttgctgtg atacggtatc atctctcctc agtccccact gtgatattgt gcagccaccc   95700
tttgcatgga ttccacaccc tacctctgca catcctgtt  ataccattcc aggctgcccg   95760
cctttgggga ctccatcctc attccagttg atctgcaccc taaatgccca ccttgctcag   95820
ccctacccac cagctttagg ataccacctc ttgccttcat gcagacacca ctgcactgcg   95880
```

-continued

```
cagtgtactt tgacagtcc cctcttgtca ctgtgcttac gtgtagacct acctcaagtt    95940
tggacttcgt tgtttagag aagcagctga acgttaacaa agtgggcgta ttagagttta   96000
aaatatatgt agagtttagg ccagattgta ggcccagtct ggttcctttt actgacttag   96060
gaaaaacaaa gtttacccag gcacgtgtgg ttaaatataa tgcaaaactg tggtccaagg   96120
gtcttaatga aatggataga ttaatctgag gattttttt tgttgcttg attattatta    96180
tttttttaa ggtagggctt gaaaagaagg ggagtggaac tagagggaa gctcgggtat    96240
agccttgtct gttgtttata gtctgctttt taaaaatata taatcaacta aattgctcat   96300
gctgaatgat gttgatagtt cccagaagga gcaaatttct cagatgggct gctgttgcct   96360
tgggtgtaga atttagcaag gtgacttttg gctattggat atccatagaa acagatggtc   96420
ttgctcattt atgcattatg cattttataa gttatatata gtaagtgttt gtgcagttat   96480
ttaagtgttt gcattttggg tttttatt tataaaaatg aggaaaaact ggtccagtgg    96540
taagaatcat ggatctctgt gttaaaatag acaaaaatgg aaatcgttag ctgtgccaaa   96600
aacaagctgg ctgattttt tgagacagag tctcgcactg atgcctgggc tagagtgcag    96660
tggcgcaatc tcagctcact gcaacctctg cctcccaggt tcaagctatt ctcctgcctc   96720
agcctcccta gtagctggaa ttacaggcac ccgccaccat gcccagctaa ttttttgtat   96780
ttttagtaga cacggggttt caccatgttg gccaggctgg tctcaaactc ctgaccttgg   96840
gatttgcctg cctcagcctc ccaaagtgct gggattacag gcgtgagtca ccgcgcccgg   96900
cctgatttt tttttaagct agctattaac tatataagga aaaaaattgc atgtaacatg   96960
gtggaggtag ataatttaaa gttgtgtcaa aagacaagtt taagttaggg atttaaaagt   97020
aagttttagc tttcttggaa taagagccgt acctatgaca tacgcacaat tcatttctac   97080
tttaggatgt ttgacttact atattgtaca tgaaagtttta gagtaatatg aataatgtgt   97140
aatatatcat atataattct aaactttcat gtagatacat agtaaatgtc aggtgtctct   97200
attcagagca tcccagtagc ttttcaattc attgtaagtt aaagtcaaaa gaacctgaca   97260
caccctgggc agcatggcaa aactccatct ctacaaaaaa attaaccagt catgatggtg   97320
cacacctgta gtcccagact gttgggaggc tgagatggga ggatcacttg agcccaggag   97380
gtccaggctg cagtgagctg tgattgcgcc actgcactcc agcctgggca acagcaggac   97440
cctgtcttaa aaaaggaaa aagaaaata ataataacac aaaaaaagaa cttgatgtcc    97500
acatggctca ccccccagtt cattctggtt attgcttaag tgtcactata tcagagaagc   97560
cttctttgac cacacaaacc actcactgtc ttaactcact ttctttcatt ctgcttatca   97620
tcaccggaca tcgtattatc tactttatgt ctctcgtctc tctccactgt agtgtaaaac   97680
tgagtggagg aacttggtat gtgtgttcag ttctctgtca gtcccctctt ggcatgtggt   97740
gggtgtataa taaataagtt attgaatgaa tgagaaggtg gtgggagtgc aggattcccc   97800
tggatagaga tttgcaaata caggcttttc tgccatttgc tctgtaactt gggttgtctg   97860
gaatcttata acatttcctt cttgtccct taccttgtgg ctatcatttg tttactcagt    97920
aacttgcaca actgcttgtg taccaagcgc tagcaggcac tggcgaaata cacgaacagt   97980
ccgacaagtc cctgcccaag tgtagcttac agtctacggg aagctgcact ggtaaataag   98040
ttcattgagc gccgtgaagg agaagtgtgc ttaaacaaat accacatatt ctcacttaca   98100
agtgggagct aaacattggg tgcacatggc cataaagatg ggaccaataa ataagacact   98160
ggggactacc taggatgggg agaggtgggg acaagggctt aaaagaacc tgtgctgagt   98220
```

```
gagtcatggg ttcatttgta ccccagacct cagcatcacg cagtgtgtct ttgtaacaaa   98280
cctgcacacg tgcccccgat tctaaaataa aaagttgagg gaaaaaaaca aaacaaaaca   98340
acttattctt tgacttgggt gtgagcagca gtagcgatag ggtaagccta tattggccta   98400
gttttcagct ttttaaaaat atatggctag aagaggttga aacttgtgat taaaatgagt   98460
cttttgagtg tgtgaaaagt attttcatca ctttaatttt tttaagtgct ctagaactag   98520
ctaaaatggg caaaacgtac tagaataaac atagctgaat gagttgaatt tacaaactag   98580
tggaagcctt ctattaaaca gtaatttacc ttgtaatcat attaatgtct aatctgtatc   98640
tttatacaga aaaacgtttc attgtgttca gttttagttt atcctttctg ttgacagtgg   98700
acatccatta tcagttcttg actattacaa atattactgc tggggaagca ttcttggacc   98760
tatttcttga tgcccatcta gaatatatat gctaagttct gagagatcag tgccaaatta   98820
ttttcaaagt ggtcaaactg gtttacactg ctaccagcaa aatgcagaat ttatttgctc   98880
cacatcctct ccaataattg ctgttgttgg acttatacgt gttagaccag tctagtgtga   98940
gtataacact gtttcatata ccaaggaatt ttgctgtttt agttaggtct gttaatggca   99000
ttggtgttat gaaacaaata ttcccacatt ttaaaaagag gtgtatattg atatatgtag   99060
ggatgaaatg aaataattgg gatttacttt aaaattcttc agcacatgta aagcacattt   99120
tgggatcagt tcaccaaatt gttctgtgga tgcagattaa agtattgttt ccgtgtttaa   99180
tttactgtcc tgtggttatg taggacagta tacctaccct tagaaaacac ttgctgaatg   99240
tttaagagta ctgggtcata atatatgaaa gctgctctca agtagttcag gaaaaagtta   99300
acacacacac acacacacac acacacacac acgcttattt ttattattaa aaatagcctc   99360
taacttaccc caccatgtgg acataaccac tattaaagtt tgcttccgga tcttttcggt   99420
atgcttatat gcactctgat tttaagcaca aatggttaca tcttctatgt agtggttttc   99480
aactttaatt ttcctgcaat taaaaattaa accgagtttt gatcctgaat aatatcacat   99540
cttgtagcat actttattca actacatctc tccttccttc cttccttcct tccttccttc   99600
cttccttcct tccttctttt tcttttttctt tttttttttt tttttgagac agtcttgctc   99660
tgtcgcacag gctggagtgc attggcacag tctcagccca ttgcaacctc cgcctcccag   99720
gttcaagcaa ttctcgtgcc tcagcctccc gagtagctgg aattacaggc atgtaccacc   99780
acacctggct aatttttcata tttttagtag agttgggttt caccatgttg gccaggctgg   99840
tcttgaattc ctgacctcaa gtgattgacc tgcctcagcc tctcaaagtg ttgagattac   99900
aggcctgagc ttctgctccc agcccacatc ccattcttga acatttagat gttcttcttt   99960
tttcctccta taaataacac aagtacacag gaatttataa tgtcctctcc ccagttgaaa  100020 agaaagcccct ccttaattct gcagatcagg tttctcaatt atgtgcattc atagttcttt  100080
ttctcggtca cttacgacaa ttggaattca tttgtatgac tatttctctc tctccagtca  100140
gacatgcggg ttcataagg gcagagattg tctattttaa tcacagctat caaagcagca  100200
ccaggcacac agtaggcctg aaagatttgt taaatcagtg gagaataatt tcaacataaa  100260
caatatattt tataaaagat cactgtgttg caacttactt tgaaagctct taaataactt  100320
gtttgtatag cagtgcttat ggaaggctac tctattggat gaagaataga aaaccctcca  100380
cattgcaaac agtgggactt aacagtggga gggcctgccc ctcccaactc cctctcacag  100440
gcaggagagc ctgccctctc atactcagtc tcacaatggg gtttagcttc cttttcagag  100500
ctaaagaacc cacccagcct tcctataaca cagactctct ttcatcttta atggacagaa  100560
tcaagattat tgctgccaga gatagaaagt tggggaaaag tcctcgaggg tccccttctt  100620
```

```
tgtttggagc aatttgatgc aggtagcttg tatttctgtt tatctgcttc ctgtttcgtc    100680
ttttatcttt tatccatcac cttaagcatt tatgctttt tttttaatct taagaaatgg    100740
gggttcactg tgttgcccaa gctggtctca aactcctggg ctcaagtaat cctcccgtct    100800
tggcttatca aagtgctggg attacaggct ataagtgtga gccactgcat ctggccaatc    100860
ttttgttttt tgtatgaggg tagctggagc acttttaatt ttctaaggtt aaaaacttac    100920
ctttgcttca cttaaggaaa ccatgtgaga gatcttgaaa aatgcacttt tcattttcat    100980
cactgcccta ccagcaacta ctggtgtact ctgccaagat aagcttcaga caagtcactt    101040
ctctggggat tggggttgga gactgactta ttctgtaaag tgggatttta acaaactccc    101100
actaagaaat agcttaaaaa aatttatttt tttgagatgg agtcttgctc tgttgcccag    101160
gctggagtgc agtggcacaa tctcagctca ctgcaacctc cgcctcctgg gttcacgcca    101220
ttctcctgcc tcagcctccc cagtagctgg gactataggc acccgccacc atgcccggct    101280
aatttttttg tttttgtttt tgtttttgta tttttagtag agatggggtt tcaccgtgtt    101340
agccaggatg gtctcaatct cctgacctgg tgatccaccc gcctcgtcct cccaaagtgc    101400
taggattaca ggcgtgagcc attgcgcccg gccaagaaat agcattttta taagaacgt    101460 acatttgtt acctacttgg aaggacggat tgatgaaatc ctcaggcaga gtctctggct    101520
tggcttcctg tgctgttttc caccccagag agggagcgtt cagatgttta ctgtagtaat    101580
gtctgtaccc accaggtggc acaattgctt tacttaaatg atttaagctc attttgattc    101640
tcagcgaggt gtgataactc atttcttatt ttaataataa aagatgccac aatatttgtt    101700
actgtatttt taaagagaat ttttgcatgt tcagttgagt gatgagagag aaattggtgt    101760
catgtttcct ctgtggtacc taatcctaca gcaagagttt caaaaatatt tttttaaaaa    101820
agctctaaga aggctataag ccttgtcatc agcccaccat atggtgccag cctattgctt    101880
tgcatagaat atccaagatc acacagtgtt ctgaatatct gcagtatcta gggggaggga    101940
agggtgagtt aaggttactg tggcaatttt catctgcatt tctcccttct tttgcacttg    102000
agacttactg agggtactag ggcatttcgt tcattgaatt aaaatgaata tagaaacaat    102060
tgaagtttag cgtccatctg tttcttaccc ctgctttctg tcacttcatc aaccacagtt    102120
ctattaactt cattcaagct agatacagta tgttgattag ccttggttcc ctgtaccaag    102180
gaggctgttc taatctgaag agcccttctg cctctatctt ctctcctcaa gagatagaac    102240
tgtgttggct ggtccgaagt agtgagttat ctcaactgat tcttcacaat tgcagatgga    102300
actccttgtt cttctctctt cctgcttctc actactggac ccagctggtc ttttttaaaa    102360
gaaggaaagg agggaaggag ggaggaattg tgcatagagg ttgtttgttt ttgtttttgt    102420
tttagatgga gtcttgctct gttgcccagg ctagagtgca gtggtgcgat ctcggctcac    102480
tgcaacctct gcctccctgg ttcaagcaat tctcctgctt cagcctcctg agcagctgag    102540
attacaggca tgagccacca tgccctgcta tttttttttt tttttttta gtagagacgg    102600 ggtttcacca tgttggccag gctggtttcg aactcctgac cttgtgatcc acccacctca    102660
gcctcccaga gtgctgggat tataggtgtg agccactgcg cccagtgcat agaggtctta    102720
aaccttatac cttatctgat atttaccagc tgtgtgaccc tagccagact acttctgtga    102780
gcctcagttt ctttgtgaat gagagtgata atggaactat cagagaagat taaaaaaag    102840 attgtaaaga gcttaaaaca atggctcata ataataaat tctcagacgt tagctgttgt    102900
ttctgcttgt cagtatagat gccgaacctt taggaagcat tccttcattg atcattata    102960
```

```
tcatctgatg acttggcatt cccatactgt cctacatctg tgttgttatt tcgtgtgttt 103020
gttctcttct gttgcctgtg tgttgtctca agctactgtg ggaaatcggt tcatttttgc 103080
ttatttcggc ttgctattta atacagtgct ttgttcatgg taagtttaat tcagtacatg 103140
cttgattagg ctttttggaat tttataaatt ttcttgaaga atgaggattt cacattctgt 103200
ctttaagtga tattatgagg aagcccataa ctcattcacc tatgctctcc ataatggtaa 103260
aacgcagtgg atggattctt gtgcttctga ctgacagatt ggaatgtcgg ccaggttgca 103320
caggcaggcc tgctttgcgc accctgtaca ctggggaagg gtgatgggtg caaatgcctg 103380 gcccataga aacgtgctgg cattttcttg agcagcgtgg actttgctca ttgtcctgat 103440
tagcgtttac ttcatgagtc cctgccctca gtggctcctc acttccagat tggtgaattt 103500
ttaatcgata agggacagaa ttaagattgt tgttgccaga gttggaaaag tccccacgga 103560
tccctctttt ctttaagagc agttttttgt aggtagcttg tatttctcct gctcctcttc 103620
cttcctgttt catcttttat tcactgactt ttaagcatct gcttatcttt ttttttttt 103680 ttttttttt ataagggtag ctgggaacac attttatttt cttgggttga aagctttttt 103740 ttttgcttc agttaaggaa accacgtggg aggttttgaa aagtgcactt ttcattttca 103800
ttgctgtcct accagcagct actggtataa ctctgtaaag gaacagggta ggtggtggga 103860
agggaatagc atcagggatt ctgaaaagta tggcagctat gcatgtccct tgattaaaga 103920
aaacaaaagc tgaggattat gtagagcagg aatacagtaa gagacaaggt ctgtcaacag 103980
cattgcttgt gcagatggct atattctgag taaactctag tccagaacat tctgtgagga 104040
gaggaggagg agtacctact gtggtgtcat tttcccagtt aggtgataac ctggctttat 104100
tggtgagaac taattcttgg gaaggtcagg gcgttgctaa agataacata gtcatacagt 104160
gctgactgtg tgccatgcac tgctagacaa actcatttta ttttgagaca gagccagaat 104220
ttgacccggg tctttcttac cctgtacata acctgtgctg ccttttatct tgtgggacag 104280
gaaacctcat atgttgacat tgtacataat acagcacccc aggcattcat tcagcaaatg 104340
tctgtctgat ttttgttgga cattgggaac aatgaaaaga atgaaaaagt gtatatttgc 104400
tagtaggtat tagatggtaa ttccttttac aggttagagg gctcctggta cattaactta 104460
cttcatcaca accttccgag cacctagtag acacaccatg tgtcttcatt taagtagtta 104520
ctacagtaga gtgctttctt cctttacttt agatttgagt catcagggtg atcttccaag 104580
aatttttttt tttttttttgg acagggtctc gctctgttgc ccaggttgga atgcagtggc 104640
acgatcttgg ctcactgcaa cctctgcctc caggattcaa gcgattgtcc tgcctcagcc 104700
ttccaagtag ctgggattac agacacgcac caccgtgccc agctgatttt tgtattttta 104760
gtagagatgg ggtttcacca tgttggccgg gctggtctcg aactcctgac ctcaagtgat 104820
cctcttgcct cagcctccca aagtgctggg attactggca tgagccaccg cacccggcca 104880
tccaagaaaa tccaaaagtt acatgacttt aaaggttacc ttagtaagaa taccttattg 104940
tttacaatat ggcagatgtc ctatataacc tcagctgcag cattcgggat ctactgttac 105000
tgtcttgttg ttcctgtcac cagctgattc ttaagatata aagcaaaaga ggagttgaaa 105060
atggagtagc attcaacaaa tgcttgtgtg tgtcttaaaa tttgtagcta aatctggttg 105120
cagacagtgg gcacaggcat tacaggcctt gttactgatg tagcaggagg gactctgagc 105180
agataacata tgcccaagaa ccacaggcag gactagcccc tgtgctgggc cactccaggg 105240
actcctgcat cacttttttca gcctgtgcat gtgtttgctc aaagatcgtg ctactggtga 105300
tcatacatac attccttact cagttaaggt agataatagt gtgctctgag acttgagatt 105360
```

```
tacagcagaa gcttaaggtt catttgttgt tcattcacca agtatttatt aaaggaagga   105420
acccttcaag ccagttttaa acaagcagac cttctccaga gttgaccctc aatttaccgc   105480
agattgtttt cgccttctgt ccttacatat tcctgagtgc atctcatgac ctggttttta   105540
atcagctggc ctgctgtctg tttctaggtc tggtatgctg ccatttgcat ctcatctcct   105600
ccagtatgaa cccccatatt acctgtgtct ctctgcaggg ttctggccag gtatacagaa   105660
ccacctgttc gagcagcctc atctgacatt ttttagaatc tgagagcact tttatttggc   105720
ataatctaat gtattgtgaa ggaaaaagca agggacacac tttggagtaa ttccctgccc   105780 tgccttttt ttttttgagat gaagtcttgc tctgtcacca aggctggagt tcagtggcac   105840
gatcttggct cactgcaacc tcagcctccc aagtagctgg aactacaggc atgcgccacc   105900
acgcccagct aattttgta tttttagtag agatggggtt tcaccatgtt ggccaggatg   105960
atgttgatct cttgacttcg tgatccacct gctttagcct ccggaaatgc tgggattaca   106020
ggcgtgagcc accgcgcctg cctctgccc tgcttttaa aatcaccagt tatacttttg   106080
tgacaagcta tggtcatttc atttgtcatt tgctgacctt caagtaaatt gaaattttac   106140
tgtaatctga gtgaagtaac cagtttgtaa ctattttaaa tattaaatcg gaaattagtg   106200
gcttagtatt agaattaata ttgagctgca gtatataatt agttattgtt tgaattaggt   106260
tgactttttc ttttgtcaat ggaatatttt tccccaattt ttagaataca tgcttctata   106320
agagttggaa ttctttttca aaattgattt ctgtttccta aattggttga cagttctccc   106380
agagctggga gcatgctttt ggtataatcg catggcaaac taagttgtag aagctcagac   106440
ttttattagg actcctctgt ttactctttg tgtcatagtg ggaaagtgga tcactctgag   106500
cctgttttct ctaagtttgg ccattgtacc tagagagtaa gatttaggag ccaagaggga   106560 atagggcta gtcaggattt tactgcctac ttcatacagt tctatgctcc ttgattttt   106620 ttttttttag cttgtgttgt tgttatttt ttaattcata aaggaaaatc atgcatgaac   106680
atatggcagt gctattgact agtgcattat tttttcttgt acacttggga agaaagacta   106740
gaatatcctc agggaggaaa ttgattcatc tttgggggtg gcagcttctc ctagaggttg   106800
agtcaattca ttttccttgg tattttccat ggttcttgaa agctagccac cttatattgg   106860
agtagtacat atttgaaagc aaataccaag cactgggtca cgtaatctat ctcttaagaa   106920 tttttaaaa cataaagaat agtttgttca ttattcaacc tgagctgaaa ctaaaaatga   106980
cgcccaattt catatttctt tttactgcta gacatgttgt ttaaagtagt acttgttgt   107040 tgtagaaagt tttaagtaga actaaagatt ttgtcttcct tttcccttt tcttttttg   107100 agacagagtc ttgctctgtc accaggctgg agtgcagtgg tgcaatcttg gtcactgca   107160 acctctgcct cccgggttca gcgattctc ctgcctcagc ctcccaagta gctgggatta   107220
caggcatgtg ccaccacacc tggctaattt ttgtatttt agtagagatg gggtttcgcc   107280
atgttggtca ggttgctctc gaactcctga cctcaaagtg attcgcctgc cctagcctcc   107340
caaaatgctg ggattacagg catgagctgc agcatccagc cctgactaat tatttttaaa   107400
aattatttgt agagacagga tttcactatg ttatccaggc taatctagaa ctcctggcct   107460
caagggatcc tcccgcctca gctttccgaa gtgttaggat tacaggcatg agcctttgtt   107520
tttctctttt aaagaagact cataatctca tcaccaggtg atactgctgt taatatttga   107580
gaatattcat tcagacgttt ctctgcagga tcaataacta ttataatggt tctgttttgt   107640
tactgtgtgt tctttatttt tagtcttgta caggacaagt gtattagtcc gttttatgc   107700
```

```
tgttggtaaa gacatacccg agactgggaa gaaaaagagg tttaatggac ttagagtttc   107760
acatggctag gaaggcctta caatcatggt agaaagcgag gaggagcgag gagcaagtca   107820
tattttacat ggatggcggc aggcaaagag agcttgtgca gggaaactcc ccttttaaa    107880 accatcagat cttgtgagac ttactaacag gagaatagca caggaaagcc catcctccat   107940
gattcagtta cctccagttg ggtccctcct acagcacttg ggaattgtgg gagatacaaa   108000
tcaaaatgag atttgggtgg ggacacagcc aaaccatatc agcaggcctg aaatatacac   108060
gtatatcaat tctagcagac catagggtgt actctgtccc tcagtttgtt taatggcatc   108120
tcttcttgtt tttcagtgga tgaatacatt gccattgcca agaaaagca tgggtacaac     108180 atggaacagg taatatcatg gttttctttc ttttgctgtt aaaaaatgag tatttgtaac   108240
taaataatta tatttttttc ttctttgtat tgagtagcag tgtttcttca ttagcaactt   108300
tttggtaatt actagtagtg ttacacaaac tctggtcttc ttttcttgt tcaagatgaa     108360 tattagagga ccctttgatt tgaaaggcat atctgtcatc tgcagatcta cagccttag     108420 gacactgatt acttagtgat tactaaggag ctggatgctt gagcataatg ctttctcatt   108480
tgaatatgtg atttgtttgt cattcttctg gttgtatcat gatgtttttt gacgcatgtt   108540
ttcacattct tacctaaagt gtttaatat tcaccatttt gaatcatttt cagtttgaga    108600
tggagtctcg ctctggtgac caggctggag tgcagtggcg catctcagct cattgcaacc   108660
tctgcctccg gggttcaagt agttctcgta attctcgtgc ctcggcctct caagtagctg   108720
agattacagg tgcacaccac cacgcctggc taattttgt attttagta gagaaggggg      108780 ctcccaaagt gttgggatta caggcgtgag ccactgcgcc tggccaagat tttcttttaa    108840
atattgtttg gaatgtacta ataagaaatc cacaagattt attttctgc aaaagtgtgg     108900 tgataccta tttcagcttt aatgatttat tttaaacaca tcaagttgga ttaatgcttt     108960
ccatggcatt aatctagatc ttacaacctg gaagttactg acatttctta tttttctgaa   109020
tgatggaagt taccaagagt ttagattatg tgaaattgta ccctttcttt tggacttggc   109080
cttacattta attactctat cctggtcatt gaagctactt tgattgcaa aatatacctg     109140 tatgaattct taaggatggt agtcttgatc atttctcctt taaaaatgat cattagcatg   109200
aaaatttcct atattataat tccagcataa aaattaccat tagcaaagta ttgctggatc   109260
tcatcttacc tcttttgttg cttattctat ttctatttct actttttttc tttctaagct   109320
gagaagacct ttatatatca tatatataac atataaatat atataatttt taaaataaaa   109380
gaataacagc aattgttctt tcataaatta ctttttttcat ttatatattg aggcagtaaa    109440
gtgtgatact tgaagagcac agatcctaga actatgctgg ttctgtgacc agaggcaggg   109500
aaaggcagtg cctcagagaa gaccttcagt ttatactcag gctgatcctc acaatggagg   109560
caagcctaca accaaaagaa aacaaaactg tagtaaaaac atagcaaacc ctgaggaaga    109620
gtgtgattat gagtttacta cattattaga ttcagatgtc caggttttaa cagaaaaatc   109680
acagagcata caaagaaatg gtaaagtatg cccattcagt agaaaaaaat taatcaacag   109740
aaactgtccc tgggaaaaga ccttagtggc agatctacta ggcaaagatt ttaaacaac     109800 tatcttaaag atgttttaa agaactaatg gaagatacag aaaaaatcaa gaaatgatg      109860 tatgaacaaa tggaaataac agtaaggaaa tggaaaccct gaaggaaac caaaatgaaa    109920 ttctagaccc taaacacttg aaatgaaaaa ttcactagac gtgctcaaag gcagattgga   109980
agagtctcaa caaagaacat gaagaaagga cagtggaaat gatttgagtc tgagcagcag   110040
gatgagaaaa gattgaagag tgaacagagc ctaaggtacc ctagggacac aatcgggtgg   110100
```

```
actaacatat gcatgtggaa gttgcataag gagtaagaga gatagggaca gagagattac  110160
ttgaagaaat aatggccaaa aatttcgcaa atttgttgaa agatgtgaat ataaacaaac  110220
atccaagaaa ctcagtgaac tccaagtaga ataaactcaa agaggctcac cagagcacat  110280
aatgaaactt tgaaaagaca gagaatcttg atagcagcaa gagagaacta acctattaca  110340
tataagggat cctgaataag cttattaggg tatttcttgt caaaacccttt ggaagccaga  110400 ggcaatggtc tgatatattc aaagcagcaa gagaagaaaa ctgtcaacta agaattctat  110460
atctgagaaa attctttcaa aagtaaaggg gagaaatgaa gatattgtca gttaaaagct  110520
gccggagagt ctctctgaag agaccacagt ggagctgaac ttgccaactg gtaatcccat  110580
ggtctataaa ttggacaaga acttgaagcc catcaagccc atgaataaaa aaagttcctg  110640
gggatgaaga gaccattcat aaagccatgg aagctgtggc tgcccagggc aaggccaaga  110700
agtgaaggcc agcaggctga ctgctctctc aaggagcact ctccctgccc aacccattct  110760
tcttcacctc cctgctgcac atgccacacc gaccacatct gcaggcatct tacgttggag  110820
ctgcagatgg gaactcatgg ctcccatttt cattgtaatc agttttgtct cctgcaccca  110880
ctcccttcat ataatctagt cagatagcac ctctggtgca gggagaaagc tcctcttatc  110940
caagagagtt gagaggtagt gactagggct tttgccaggg cttgtttact aaggaccttt  111000
gtgggaggaa ccatgctgtc atgaccaaag aggagaagca aagagggcct gcttgacccc  111060
aggacccaat cctgtactct tctctagtca tgccactgtc aggagagctc tgctcattcc  111120
agtggaagat gacagtaacc tgcacggtga tgtgaaaaaa caacgatttc ctccctgatc  111180
ccagggtagg tggctctaga aggttgagag caatcctgta ttaagttcat gtgttggatt  111240
tacttttaca aaaaattgta tgtataaata atacaaaaca aaaaccccttc tgagattttt  111300 tattttattt ttttgagatg gagtctcact ctgtcaccca ggctggaggg caatggtgcg  111360
atctcagctc actacaacct ccgcctctcg ggttcaaaca attctcctgc ctcagcctcc  111420
tgagtagctg ggattacagg tgcctgccac catgcccggc taattttttgt attttttagta  111480 gagacagggt ttcaccatgt tggtcaggct ggtctcgaac tcctgacctc gtgatccact  111540
cacgtcggcc ttccgaagtg ctgggattat aggcgtgagc caccgcgccc agccccttc  111600 taggattttt agtggcagtt caaatagtcc cacatgtggt catcagaaat aagccattcc  111660
atcctggaca acatggcaaa atcctgtctc tacaaaaaat taaaatcagc caggcatggt  111720
ggtgtgtgcc tgtggtccca gctacttggg aggatgagat gggaagattt gttgagccca  111780
ggaggttgaa accagcctgg gcaatatggt gacacctcat ctctaaaaaa aagtttaaaa  111840
attagccaaa catggtagtg tgtgcctgta gtctcaatta ctctggaggt tgaggtggga  111900
ggatcgcgtg agcctagaag gcagaggttg cagtgagcca agatcatgtc attgcactct  111960
agatcacaac tctatatcaa caacaacaac aacaacaaaa aaaagagggg gggaaagaag  112020
ccattcctca caccaatatg ggataagctc cttgacctct aagggatagg attgcatcct  112080
gctgtgggtt ttcgaatctc tcccctacct tgttttgtgg ctgtgaaatg cctcatgatc  112140
atgtccaagt atgtctttca ctggctgatt tccgaatcac gttctaattg cttggccctg  112200
ccatgtggac ccagtattca ttttgagcat aactgtacta aatctttctt tctagatcag  112260
tgtaataaag gtgtaatgtg caacttaaaa taaataaaag cttgtgtctt tttgtttgtt  112320
ttgttttgag acaaggtctt gctctgtcat ccatgctgga gtgcagtggt gtgatcatag  112380
ctcactgcag cctcaaaccc ctgggctcag tcaagcagtc ctcctgcctc agccccccaa  112440
```

-continued

```
gtagctgcag ttacaggcgc gcaccaccat gcctggctaa cttgttgttg tttgtttgtt    112500
tttcgtagat tcatggtctt gctaagttcc ccaggctggt ctccatgttc tgagctcaag    112560
tgatcctctc acctcggcct cccagagtgc tggggttaca ggtgtgagcc acaacaccca    112620
gcctcagaaa atagctatag aatatataca caaggaaata gaaggaatt taaatctttc     112680 actataaata atcaacaaaa cataaaaagg aggctggatg tggtggctca cacctataat    112740
cccagcactt caggcagatc acttgagctc aggagttgga gaccaacctg gcaacatgg     112800 caaaaccctg tctctacaaa aaaaaaacta gctgcgcatg gtggcacgca cctgtagtcc    112860
cagctgctca ggaggctgag gcaggagaat tgattgagcc tggaagggag aaggttgcag    112920
tgagccaaga tcatgacatt gctcctccag cctgggcaag gagagtgaaa ccctgtctca    112980 aaaaaaaaa aaaaaaaaa aaaaaaacct aaaaaaacag taattcagga aatgaaggac     113040
ataaaaaact ttaaggaatg tacaaaacaa atagccaaat gacagaagtc cctccttatc    113100
agtgattact ttaaatataa atgggttaaa ctttccaaag gacagagatt ggcataatgg    113160
gtaaaaatta caggatccca gtatatacaa gagatttaca ttagttccaa aaacacaatt    113220
ttaaagtgaa agggtggaaa atggtatccc atgcaagtag taaccaaaag aaagcaggag    113280
tgattataat aatatcagtc aaaatagact ttaaatttaa acaggttgta agagacaagg    113340
acattcactg ttggtgggaa tgtaaaatgg tacacctggt ggggaaaaca ggatggcagc    113400
tccttaaaaa attaaaaata gaattaccgt attatccact aattctactt ctggccaaag    113460
tgggtagatc acttgagccc aggagtttaa gaccagcctg gcaacatgg caaaaccctg     113520 tctctacaga aagtacaaga aattagccgg gtgtggtggc atgtgcctgt atcccagcta    113580
cttgggagac tgaggtgatc aaggaggatt gcttgagcct gggaggtgga ggttgcagtg    113640
agtgccactg cactccagcc tgggtgacag atccagaccc tgtctcaaat aataataata    113700
ataataataa taaatttttt aaaatttatt ttagaagaat tatttatagt ttctctgtga    113760
ccacttccct gatgatacat atgttgccat acttaacaaa taccaccttc ccttgttgct    113820
gtacctaaca agttatcacc atcctgaatt gtatacttat catttccaag aaaaatatt     113880 ttattgtatg tgtaatttcc aattaaaaca tattgcatat tgtttgaaaa ttaaataatt    113940
tatttaaatt gcttcactct ttcttgatac ttatacctat attaaaagac attataccta    114000
taataaaaat tacatcacct gaaaaaaaag tatgtgtata ttaccacagt tacaaagaat    114060
agaaaaaggg gcctctgaca gtgtctgcca cttagcgctg tagatgagtt agtttgtcta    114120
aatatgaagt cgttttttact tttcttttgc tggtctcatt tccattttca ttgttttttg    114180
tttgatctaa aattttactg atatcatttt tgtaggctct tgggatgctc ttctggcata    114240
aacataatat cgaaaagtca ttggctgatt tgcccaactt taccccttc ccagatgagt     114300 ggactgtgga agataaagtc ttatttgagc aagccttag ttttcatggg aaaacttttc     114360
atagaatcca acaaatggta agtagatgag accactgagt tctatttttt ttctcctatc    114420
taactctctt ttgcagcata cttgagatag ggatatcata ctcaaacata aatattccca    114480
tttttgataa agttccccctt tagattcagc ttagtacatg ctgctctgtg gatgggagtt    114540
ttccagttac aggagtaaag cacttctagc acttcccatc ctgtcgtctg tgactggacc    114600
ctccccaccc accccagtcc ctcttgttgg gactcccaaa agattagacc catacgaagg    114660
actttttttt tttagacgga gtctcgctct atcaccaggc tggagtgcag tggcatgatc    114720
ttggctcact gcaacctccg cctcccgggt tcaagcgatt ctcctgcctc agcctcctga    114780
gtagcttggg actacaggtg cgtgccacca cggccggcta atttttttgta tctttttttt    114840
```

-continued

```
ttttttttga gatggagtct cactgtgtcg cccaggctgg agtgcagtgg cgcgatctcg 114900
gctcactgaa agctccgcct cccggttca cgccattctc ctgtctcagc ctcccgagta 114960
gctgggacta taggcgcccg ctaccacgcc cggctaattt tttgtatttt tagtaaagac 115020
aggatttcac catgttggcc aggatggtct cgatctcttg acctcgtgat ccacccgcct 115080
cggcctccca agtgctggg attacaggcg tgagtcacca catccggcct aatttttgt 115140
atctttagta gagacggggt ttcaccatat tagccaggat ggtctccatc tcctgacctc 115200
gtgatccgcc tgccttagcc acccaaagtg ctgggattac aggcgtgagc cgctgcgccc 115260
ggccttaaac atttgatttt taaagattac ttttttattt aaataaacca actcatttt 115320
tatgtttagc ttccagataa atctatagca agtctggtga aattttacta ttcttggaag 115380
aagacgagga ctaaaactag tgtgatggat cgccatgccc ggaaacaaaa acgggagcgg 115440
gaggagaggt gagcacatgg ctggggtgtt gtctaaccac ttaggggact atctaagagc 115500
cccagataca caaaggcaag gcagaatgac tggttttccc tccgcgcctt cctggtggaa 115560
ccacatgttc atgagatgta ttagagcgtg tcacattatt caggtatttt ttctcaccac 115620
tctttccctg cagtcagtga acttccattt tgagtcagtt aactttgacc cattttttt 115680
ccttcccatt tagaaggggt ggctcctttt aataaaaaag aatctttat tttgtagttt 115740
gaggtttaac gtggtatatt tttacaagat tcatttggtg tgtttttatg tttgccatgt 115800
ggaaacaaaa atacaactta gagttgctgc ttctttttt gaccatctgt ttttgtgtg 115860
tgaatgagaa agagaaacat tttataatct cttagtaagg atattagttt taaggatagc 115920
tcagtatgga gaatacttct taaccatcac ttcctcagtc ttatatgtag catagagaag 115980
tagaaatggc caggtactca cactcagaaa tgggctctgg tctcagctct gaagattcca 116040
cttacatgcc acaggctaca ctgggatgtt taaggtcttt aatttatttt ttaaaatgtg 116100
taaaattgta catactcaca ggcaggtgac ttcaacatgc gtcttcccca agcttctgtt 116160
ttccttaact ctaaaatgaa gatgtttgaa gtccagaagg cagcatgcag acctagtggt 116220
ttccttgtta gggtggtgag atatataggt gggttttaaa aaatcctatt ttccacattt 116280
cctgtaatat ttttatcaat taataataaa aaaataaaat gaaggaggat gaaatatatg 116340
gtccccggtg tccatctca ggatggaatt ttatcatttc aaatgaaaga gtaacatgtg 116400
agaacacatt gaaagttgag tatcactttt ggagaattca aacctcttgg cccaagtata 116460
aattgagagt gatgttaaga acatctccaa agctctttta attgtaagag cctataaaat 116520
tatcgaccat gatacatctg catattttg cctctgactt atatactagt aggtttattt 116580
atggatgagt actcttatta acttttaatg aagcttttc atttccctag tttactgtct 116640
atatagtaag tctgttacta taagcagatg cagtttacta agcagcaatc aaaattaaat 116700
aatacagagt gggattggat atccttgagt gtgaaataag aatacctgcc aacacttcca 116760
ttcttactcc ctggaggctt ttttttgca ttagtcccga tggggccagg aagtgctttg 116820
cctccacctc ccatgtgcac ctcaaccact tttgggatgc ggggatggag gtgctgcagc 116880
agcacctgat aaattgttgg ctttctaaca ggacttgcct gtgaaagtca tggcagggac 116940
tgggacaaaa ttcccttagc cgaaggctct tccttgttgt ggacactctt tcctcagcta 117000
gagcttcctg ctaccttggt ggaggatggg gaggaggtgg cgcgtagtgg gcatggtccc 117060
gtgggatgga ttcagaggc agtgcgaggt gggcaaactg gggcaggcta cttgacttct 117120
gtagacttag ttttctttt ttacagttgc attcctacct acatcggggc ttttcttgtt 117180
```

```
tctttgtttt aaattaaatg aaatactaca ttcaggatat tacaaaaagc atttaaagtg   117240
ctataccaat gtaagttttc ttttaaaat  taaacataat tttaaaacat cagttgtcca   117300
ggacaccaga aaagcctcag actttgtgtg gccttgggta gaaagacggt acttggaaaa   117360
ggattttttt actgttagca ggtttattcc caatgcagtg gaaatttatt ctcccataat   117420
ttctcagttt tgtttagtaa tcatatccta gtcctcaata gataattatg agaaaataac   117480
atgtaaatgc attttcattt tgatattttc agtttacaga tatagagcaa tagtgtttta   117540
gatctggatt gggaagttag gaatctattt tagtagtttc tcatcactta gactgaaaga   117600
actatggagt tggtattctg tttgaattac aaagatgttt ttatctcagc agcctgaaaa   117660
catactaatt ttatattaaa tcagtttatt atttatattt ggtaaaatta gtacaaaatt   117720
ttcagttaaa tcaatttatc gtttgtattc ggaaaattag tacaaaataa tcattcagta   117780
acttgttctt gtcttccagc gaggatgaac tggaagaggc aaatggaaac aatcccattg   117840
acattgaggt tgatcaaaac aaggaaagca aaaggaggt  attttttccc cctagtattg   117900
tttaggcgaa taaatttat  tactagtttc ataaataaaa cattcatgtt gcttgttcta   117960
cttaatatat taagtgctat gtggaaagca gcatgatatg actatttttc aacaatactg   118020
tctttgcttt atagattgta taattttgtt tgctaataga tatgaataaa ggaaggctta   118080
aaggatagaa aatagcacta atgagtaatg atgttcccta gaacagcagt cctcactgac   118140
tttcttcgta agccattagc tcagtaggtt aacaagtggt ctagtgaatt ccaggcagcc   118200
ttagggtctc cattcacgct atagatgccc cagcgtctgc ccatcctagg cacccatgcc   118260
gtgcctgggg tgactgcagg gagctggcag ggactcggca cagccctcct gttactcaga   118320
agcagcaatt tggtcacacc aggggagcc  aggaccatcc tctctcacat ggtgactgtt   118380
tcatcttatc attttaaaaa atcattatac aagagattgt agtttctgga ttcaggggc   118440
tcgtgaacct ctacaattgc atgtaacttt tacataggtt catagaggta tttttccaaa   118500
gacacagtct atagtttcaa aaaaatttct cagagagttc tctctctctg ctccaaatta   118560
taagaatagt tattatttta agcctataaa aacagaaggg tctaaattta tctaaacttt   118620
aaaatgacat cagtaatata tgtttcttat agacaaggta ggaaatacag ctaactgaaa   118680
gaagaaaatt aaagtgattt ataatattat ccataatcac tgtcaacctt ttggtgactt   118740
tttcctgaga actctttctg taaatgtat  atgcctgtat attcataatt ctgaatctag   118800
tcacttttta aaaataatat aatggaagct ttgtaatttt tagaaccttt taaatttact   118860
ctaccttgat ttttttttc  tctttttct  ttttttgagac agggtctcct gtgtcaccca   118920
ggttggaatg cagtggcacc atgactcact gcagccgcca actcctgggc tcaagcagtc   118980
cttccactat ggccttgcaa agtgctggga taacaggcat gagccacctc cagcccttga   119040
ttttattttt tttttttttg tttttgagac agtctctcac tctgttgccc aggctggagt   119100
gcagtagtat gaccttggct cactgcaacc tctgcctccc agattcaagt gattctcctg   119160
cctcagccta ccgagtagct gggattatag gcacatgcca ccacgccctg ctaggttttt   119220
tttttttgtat tttagtaga gatggggttt catcatgttg gccaggctgg accttgaatt   119280
tttttttatg tcaaatatat ttgtatacgt agctatatat tattctgtca catgaatgtt   119340
tcataattga gttaccttat cctatgtgga tttcccagtt gtttattcct cctgtttttt   119400
gcttttataa acaatgctgg attgattctc acataactca ctatctgtgc tcatagattt   119460
ttttcattag aaccgattcc tggaagttgt attgttgagt caacgtgttc tagatacatt   119520
gttaaggctt tttttttttt ttttggttgt atatcaccaa attggaaatt ggtcgttttt   119580
```

```
ttctgcataa tttatatgaa tgcccaaata agatcctgag ggttagctaa attagattgt 119640
ttgggaaatc aaattgtagt tgtagttttt attaagcttt gtgttgatgt attgctattt 119700
actaggtttt tcagtggcac attttaaatg agagaaaaca cttgatttca tacattttta 119760
taattcttat ttatataatt tctgattcag aaagaaaatg gctaaatcat tgtttttttt 119820
tttttttttt tttttttggag atggagtctt gctctgttgc ccaggctgga gtgcagtggt 119880
ccgatctcag ctcactgcag cctctgcctc ccaggttcaa gcagttctct gcttcagcct 119940
cccaagtagc tgggattaca ggggcccgca accatgcctg gctaattttt gtattttac 120000
tagagacgga gtttcaccat cttggccagg ctggttttga actcctgacc tcaagtgatc 120060
cacccacctc ggcctcctaa agtgctgaga ttacagccgt gagccaccac acctggcccg 120120
tagtttcttt ttttttttt tgagacggag cctcactgtg tcgcccaggc tggagtgcag 120180
tggtgcaatc tcggctcact gcaagctgcg cctcccaggt tcatgccatt ctcctgcctc 120240
agcctcccgc cattctcctg cttcagcctc ccaagtagct ggggctacag gcgcccgcca 120300
ccgcacctgg ctaatttttt gtagttttag tagagatggg gtttcactgt gttagccagg 120360
gtggtctcaa tctcctgact tcgtgatccg cccgcctcag cctcccaaag tgctgggatt 120420
acaggcatga gccaccatgc ccagccacct ggcccgtagt tttttaagt attaaaatga 120480
tactagaaca gacgtagtca gttggtgatc tttattaaac atcgtagtcc catacacagc 120540
agtttattgc ctactaatat ttttgtatta cccacttgtt gaagaaatta tcactaccat 120600
tatagttttg cagtgtcttt agctcagtct tttaaaatat gaagcagaaa gtcatatttt 120660
cagctttatc agtgaatgct aatgcactaa caagatggaa ttatgagcaa ttataaaaac 120720
ttcttgttct taaaatggtt accagtaagt tatattcttt aacttgacaa gattttactg 120780
tgtttcattt ctgaaagttt tggttttaca gaaattaata gccgtcatgc attttaaaat 120840
gataaggtat attattttag agtaagttat ataagttgcc gtaaaaattg tgttatccaa 120900
aaatgtgtat aaaaagctgt aatttcatgt agctaaatac agatgtgtgt gtggccacaa 120960
aactcattag cagagaatac agatttttt ctttctatat tactagagga agctgagaat 121020
tcttattttc attggcttga aacgatagag taaggaagta tttgtacaag aaggagtgga 121080
acacagtttc attgtgttta gtcaaaactc agtagcccaa attctgtctg tgaactgcct 121140
gttagaattt atagatctca tttggttctg atagggcatg gtatttgtct tagattgttt 121200
tggtgccatg ttaaggaaat aaatatgttt attactgatc atttgacttt ttttaagttt 121260
cattcatcac ctgtgtatat catgcaggtt cccctactg agacagttcc tcaggtcaaa 121320
aaagaaaaac atagcacaca agctaaaaat agagcaaaaa ggaaacctcc aaaaggaatg 121380
tttctttctc aagaagatgt ggaggctgtt tctgccaatg ccactgctgc taccacggtg 121440
ctgagacaac tagacatgga attggtttca gtcaaacgac aggtactcat aagcctggtc 121500
ttggatgtaa aagaattaat tagcacttta gaggtgtttc tgttattcat atatgtgaat 121560
gttctctttc cgcaaatctc aaaggagcat tttgtttcga aggaattgga cagatcttaa 121620
gtaccagccc attgtttttc ttttaatga acatataaat tgaagtgtat ggatatagtg 121680
tgatctgaaa gtatttctga agtatatagc aaagcatatg aatatcatat ttatattata 121740
tatgtgtctg tgtctccatg atttctcaca atatgaacat accctagtaa cctgcatctg 121800
gatcaaaaaa tggaatgttg ccccaggcc catgcatttt ccctcctggt cactattcca 121860
tggaatgttg cattccctca gcaactccac ccctctttta ttacctgact cctccttgta 121920
```

```
ggtggccact attctgattt tttttttttt tgagacggtg tctcgctctg tcgcccaggc  121980
tggagtgcag tggcgcgatc ccggctcact gcaagctctg cctccccagt tcatgccatt  122040
ttcctgcctc agcctcccga gtagctggga ctacaggcac ccaccaccac gcccagctaa  122100
ttgttttttg tatgtttagt agagacgggg ttttaccatg ttagccagga tggtctcgat  122160
ctcctgatct catgatccac cgcctcggc ctcccaaagt gctggaatta caggcgtgag  122220
ccaccgcgcc cggccctgat ttttttaat tttattttgt ttttgagaca gtgtcttgtc  122280
ctgttcccca ggctggagtg cagcggtgcg atcttggctc actgtaacct tgcttccgg  122340
ggctcaaatg atcctcccat ctcagcctcc caagtagttg ggagtacagg cgcttgtcat  122400
cacacctggc taatttttg tgttttggt agagacgggg ttttgccata ttccccaggc  122460
tggtcttgaa ctcctgagct caagtgatct gcccgcctca gcctcccaaa gtgtactgag  122520
attacaggtg tgagctacca cactcggccc tgttctgatt tttaaaacca taagttgttt  122580
ttgtccattt ttgaatttta tataaatgaa agtcatgtgg tactgtttat tttatgtctg  122640
gctttctttc aacctgagag ctaaacagtt tttcaaagtg gtcctgtcat tttatgtgcg  122700
ttttgttttgc acatcagcgt ttcccagctg tagcactatc ctcatgatgg gccgttctgt  122760
gcactgtaag atgttgagca gcatccctgg tcttgaccca gtagatgcta gtagcaccct  122820
cccctaccag ttgtgacaac agaaatatcc ctaggcatca ccagattacc tcacaggggc  122880
aaaattgtcc ccatttgaga accactgctc tacatcattg ccatattttg gtagtcttaa  122940
attttagccc ttctgatggg ttataatgat gcctcattgt actttttatt tggcagttcc  123000
ctgatgacta atgaggttgc tcaccttttc atccatttgt tggtcatttg gatatcctct  123060
tttgtgacat gtctactcaa gtctcatctg ttttttttct gtcaggttgc gtattttctt  123120
attggtttat aggtgttctt taggctctga gttgttttct acaacttgta ttttaaatgc  123180
tgtaaatatg ttttgcattc tgtgactctc aatggtatct tttgatgaac agtaattctt  123240
cattttaagg tagtttagtt tcttagtctt ctgaggttag tgttttttgag ttctgttcac  123300
ctttctcaag gtcatgacga tattctctca tgttagtctt agaagtgttg tttttacctt  123360
tacattttga tctagaaatg tttttctgta tttgttgtta catgtcggat taatagtcac  123420
tgttttgttt tcatatgagt atcaatttgg tcaagtattt attgaagaaa ctgtccttta  123480
tcctttgcaa cgcagcagga cctttgtttt acatccagtg tctgtatgca tatgggtctg  123540
gtttgaggtt ctctgttcct ttaatctctt tgtccatcct tcaccaatac atactgtcct  123600
aactttatgt actttattaa tttagttatc tggtgtaata taagttctcc aagattgtct  123660
tggttatccc tggccttta ctttccatat aaaatttaga attactttat caattttcag  123720
aaaaataatt ctattagagt tttgattggg attgtattgc atctatagat aaaaatggag  123780
aattaacatc tttattgagt tttctgatca gtgaacctga tataccctc tacttctata  123840
ggtttgtaat ttctctcaat gttgtattgt tttctgtgta agaacttaac gcatcttttg  123900
ttagtcattc catgatattt ggtactttt tggtgctctt gtaaaggata ttgttttta  123960
aattactttt tataattatt tttgcctgct atgtagctta ttattttaat ctgattgcat  124020
agtacattta aactgaaaat tcaacctagt agttgggtcc tgtcctttca ttctctctct  124080
ggaattcagt ttccagaaat ccatcagcaa gttgttgact gactattttt ggttttgct  124140
gcttttgatt tatcttgatg gttcccttgg aaggtcaaac agtagaccaa ctgtcatctc  124200
atagacgcga agagcagggc gtgctgctgt ctttcttgtg gtttagggag gcagcccaga  124260
ccaggaccca agcacactct gtgtgctcag aggagcggct tcttcttgtg gctgctggca  124320
```

```
cagctgcact ctaatcttag gagaatcact taatctttct aggcctcttt tcaaatgaga    124380
ttaatcctgg cctgcctgat ctcacagaat atgtctgggc tactgtgtga gagagcattt    124440
gaagttctgt tgcactgga agaactgtct cgggctgtga gctcttgttg acattgtcat    124500
cttcctttac aaggatgctc cttctctcct ctgctgagtg agctcctggt ggttgctgtt    124560
taatatattg agaaaagaaa aagaggcctt cctcttgcac cgaggtgtta ttgactccat    124620
agggtgagag agaaaagatt ctttagtttt cagagcaggg tcaagagcaa gaattttta    124680 aatttgaagg tcgctcacaa ttatgaagag ggaggactca gcctcactca gagaggaggt    124740
gggtgatttc ctttccacag cctttagcg ccacagtgca gcagtgtgtt cattgccaaa     124800
tgtgcttcta gactcaaaat gggcagtcag tccacttggg ccacttgttc tggaggccgc    124860
catgtttggt atatcaagga tatattctga aaataacagc aaactcgact aacaacagct    124920
taaacaattt agggtttat tttctcaaat ggcaagaagt gccaacatca gtggctactg      124980
gtgttagttc atgtgttcag tcatgctctc agggacccag gtacttttca ggtcttctac    125040
tgtgccattc tcagctgttg gcttttcatc ttgcttgttg cctcatgttg gaagctactg    125100
gagccatttt gcaaccctca catctgcatt cagggcagta tgaagaggag gtgggggtgg    125160
aggtaacctg tctgtccctt ttagcaggac aagcaaaagc cttaccgaa gctccttagc      125220 tgaattctgt gtgcccgtgc gttgcgtact gctcttcctc cttcccaaga catcatcaac    125280
ctctaccagc gagaagggg ctgggcatgt ctcttaaatt agccagtgaa cagtgctggt      125340
tgcatcaggt ctttctctga gtggagaata aagtgatctg atgttaaaag aggaatcact    125400
gtgcccacag taaagtagaa aacagaaagt tctgtatgac tgagggttgg gtgggagggt    125460
ggtgtctagg tagggcgtca ggacaagtgg atggcttttc ttttcatct tgttttttct     125520 ttaagtgtga ttacctttgc atcctatttc ttacctattt cattgccact cactttccag    125580
ttagcatgat ggtggcagta atctctgttt ttttcctgct taataaacac tagatgtttg    125640 gcgggggaa ggggcgtat tttgttttttt ggagacagga tcttgctctg ttgtccatcc      125700
tgggactgta gtgatacagt catggatcac agtagcctca aaggcctggg ctcaagcagt    125760
tgcccacctc agcccctaa gtaggtagga ctgcaggtga gcaccaccac acctggctaa      125820
ttttaaaatt ttttggtag agacagggtc ttgctgtgtc acccaggctg ttcttgaact     125880
cctgggctca aatgatcctt cctgccttgg cctcccaaag ggtgtgatt acaggtgtga     125940 gccactgcac tagcataatt ttttttggc agggtctggc actgtcaccc aggctgaagt     126000
gcagtggtgc gatctcggct cactgcaacc cctgcctccc agactcaagc tatcctccca    126060
cctcagcctc gcaagtagtt gggactacac agcctagata tttcttcttc ttcttcttct    126120
ttttttaaaa ttatacttta agttctaggg tacatgtgca caacgtgcag gtttattaca    126180
tatgtatgca tgtgccatgt tggtgtgctg cacccacttc gtcatttaca ttaggtatat    126240
ctcctaatgc tatccctccc cactccccca accccacgac aggccccggt gtgtgatgtt    126300 tcccatcct gtgtccaagt gttctcattg ttcaattccc acctatgagt gagaacatgc     126360
ggtgtttggt tttctgtcct tgcgatagtt tgctcagaat gatggtttcc agcttcatcc    126420
atgtccttac aaaggacata aactcatcct tttttatggc tgcatagtat tccatggtat    126480
atatgcagcc tagatatttc tgatacggaa aatgcatcag gaagagggt ataggctact      126540 gagcatttag agctagcttt tagttcagaa ttttagatgt tttgcattta ctctctctgc    126600 ttctttata acgttactta atcacagtgc aatatatacc cagttttgta ctatctatga    126660
```

```
acaaccagct agagtgacaa gagtggtctg tttcactgga atgcgaagag gacatgtaat  126720
attctaaacc ttgactttt cctgccaaaa gttgctatgt tgcatttta gccaaaaagg  126780 aatccagtga acataatctg agtactttgc aattttcctg ggttttcggt aactgaaaga  126840
ccactgagca agatcctaag agattgtaat gtctagcatg gcagccagca gccccatgtg  126900
tggttgttta aatttagatt aattacaagt gaaaaaaatt taaaaatttt cgggtagcat  126960
cttctactca tgaatgtctt ttacatttta cttgagaaaa tcaagctcct cttccgttgg  127020
ctttcttagt tgcttgtgtg attattcaaa gatgaaaaat gctggagttc agagttccct  127080
ggtgcttgac acggatatgc cctctacttg gagtagagag aaaatagcat acttccgtga  127140
cctgtctcat tcaagggtcc atgggaaaat taaggagcag ccatagcctg ggaggttggt  127200
attgtttgtg gtctttcttt cgactgggta aggacagtga agattacct tgagccaagg  127260 cagtaatgtg gaaaaagata atttgtagga aagtgaagac gtgacagtta atcaaagtta  127320
gacttctgga aatctcactg acattgtgtt ttcctcgccc cccatcatt aaagaaatct  127380 atgcttgtgc acttctgccc tgtgtagaag cggtggacag cacagtgatc ttggggcgct  127440
gtgaggctgc acccgcagtt ctgttgtaaa gactgggcct ttttggtcct tactgtggct  127500
gctctgttac ttcagttcaa tcctatgtgg tagtaagccc agggatttct tctgtctttt  127560
atgtaagact ccaggtaggt gttttgctgc tcaggtatca cctgttagga agctgtggat  127620
ccaggactgt gtacgtgaga gccctccgtc cctcctcct tgggttgtac cttatctgtt  127680
gctctgaaca agcaaataat aaacctagtt agatgcttca aaggatacca tagggatctc  127740
agaattcagc tacaacagat gttagtaacg tctttactct tgggttttg tttctttagg  127800 tttttaagtt ctgttttcat accttatat agttttatt tttaaaatga aaattatttt  127860
ttccttccta gatccagaat attaaacaga caaacagtgc tctcaaagaa aaacttgatg  127920
gtggaataga accatatcga cttccagagg taggattatg ttaacatcat cttagaagtc  127980
atattcaagt tttacatgtt taagaattta atatcggtgt gatacatccc cagtatacat  128040
ctcttggaag agtatatgga cataattta tgaacccagt tgatgttaaa attccgataa  128100
gagaaaatga aaggttcgtt aagctcataa ggacatactc atctctaaat gtaatgtgct  128160
aaaatgactc atttggatat ccaggtcatt cagaaatgta atgcacgttg gactacagaa  128220
gagcagcttc tcgccgtaca aggtagggg aagttcttct aaagagttta ggaggccggc  128280
tgtggtggct cacacctgta atcccaacat tttggaaggt tgacgcattt gcttgagccc  128340
aggagctcaa ggctgcattg atccatgatc acaccactgc attccagcct ggacaacaga  128400
gggagaccct gactttaaaa aaaaaaatt ttttttta tggaaaaaaa agagcttagg  128460
agcattggta gattttaggg aaaagttacg tcctgccta ctcccagcac ctagattctt  128520
ggacaattat gtcctagtgg atatcatttt agccaaatta ctgtattcct ttgggctttt  128580
ttcttttcct ttcccacttc tcacaagttg taaaaactta accgggaacc ctgagtcttc  128640 taaggtgta tttcatttta ctagttactc atcgagctct gactagccag gaagtacaaa  128700
accccaaaag aagcagacag agtgttcagc tttaaaggtt ggggtgctc tggacctgcg  128760 ataccaaaag atgaatgcag aatgtcccca accctagggc aattgctggg tgacttcagc  128820
tgttatgtga catgtaatgg gaagacagat atcaaaatga cagggtcggt catctccaga  128880
atgtgtctag aattggctgg tactttttcc tactctaata atacacgaaa ttattgcctg  128940
ctgttaaaag cctgtatgtt ttcttatctg gataaagagg taagtgtcac ttgtggtttt  129000
aaaaaaatgt ttttctcttg tattttaaaa aatgctttct tacatcctta gccatcagga  129060
```

-continued

```
aatatggccg agattttcag gcaatctcag acgtgattgg gaacaaatca gtggtacaag    129120
tgaaaaactt ttttgtaaat tatcgacgcc gcttcaacat agatgaagtt ttacaagaat    129180
gggaggcaga acatggtaaa gaagagacca atgggcccag taaccagaag cctgtgaagt    129240
ccccagataa ttccattaag atgcccgaag aggaagacga ggtaaatctg aaacaaaaca    129300
gtcacttctc ttgtcaggtt cacgcttgat actccagttt ctaaagtgat gaattttttc    129360
agctatagag attttaggt atcagctgta ttagtaactt cactcttacc tgtaaatagc     129420
cggaatgtgt atgcattgac tccagttctt ggtgcctgta tattattcac atgttaattt    129480
ctgggcaaat cctgaattac atcctgattt cctccagcta caaaatactc tgcattatca    129540
gttttttcctt aaatacagta aaatcttgag tgacaaagac aggggagtgg gggcataaac    129600
aaaaagtaaa aatgcagtga aagctgtcct gtctgtgagg gatgtcgatg aagctccgtc    129660
atctgcaatg tgcagtcaca tcatcatgac gcagcacagc gagccagcca ggagctcctg    129720
aggcctctcc ctgctgtcca gatctttcag cctttgatgc tctttggggc tgattggctt    129780
aagtattgat ggggacagtt ctgtggctgg ctggaacttc tgtgatggtg ctaatttct     129840
ggaatgataa ccctggtctc atctgtcacc tccctgcttc ctgtgtcagg ggcacctgcc    129900
atttccccat ctagcctggc ctgccttgct gttacatttg tccctctatt cccagagcag    129960
atgagcctgg ggctgggcat aagaaagagt tacttgccaa tcactttgca tctgaatttg    130020
ttcacaggca tggtaattta agaattaatt tagctttgta aggaaagtca ctttcacatc    130080
aaagcctttt caaaccatac tggaatgttt tgagattacc tattttgtat tgcgtgtgct    130140
accattttgc tccaagggcc tggctctgga aacagcccag aaggcccctc ctgacctgag    130200
catgaagta cctcgtgagg tattggcatc ccctgggagc gtggtgccgc cactccatgc     130260
agggcctctt tgctgactgg agaaaggacc tcaaggcaca gccatctgta agaacaccat    130320
tgaaacatat taaatttgtt agaattagat tcttttagagc cttttgccag aaaatcttta   130380
taataagtgt accacgtcta taatattgcc aaggtcagta cccctgaatc accccatgc     130440
atagctctgc ctgaaaagag catgtgaatt aaatgatggt gttttatct ttcagcagtg     130500
attttttct ttattattat ttcttttat tttcagtgat ttttgtacca gcactaattg      130560
cccctgttag cactcagttt cggaagcatt gaaaagctgg agactgctgg ggaagaacca    130620
ttagaatttg caggaatgaa agcttgcttc ttgtgtgtgt gttttccggc ttcggtccca    130680
ggatgactga agcagaaaac agttgggaac gctggctcta ttccctcttc gcatttgatc    130740
aaagccagtg ttggctgggc tggcataaca aatctcatag taaatttagg accaagagtc    130800
cctaccaaca ggatgtcagt tgttgtgcat atgttttttt cttcattctc ttattcttgg    130860
atcattggtt gactgactta agtgagtcaa gtattttttt tttaaccttg ttattagccc    130920
agaaggttct tccgtaatga tccacttacc gtgtggattg cattatcaaa gtaccgtctt    130980
tcttttcaca gtctagttat ggctcctcca agcagcagat catagttttt ccttggtgat    131040
tgatcttcca tgtctctatt tacccagcct tctctgcaaa acaaaatgaa gaatggtatt    131100
atctaactcg tgtttagttt catagtcctt atatcccttt acaaactttt tcactccgct    131160
agtcatttaa aatgtaccc ctcatacctt tcttttcttt tttttttgag acagagtctc     131220
cctctgtcac ccaggctgga gtgcagtggc tcaatctcgg ctcactgcaa cctccatctc    131280
ccaggttcaa gtgcttctcc tgcctcagcc ctcagcctcc ctagtagctg ggattatggg    131340
tgtgcaccac catgcttggc taattttgt atttttagta gagatgggt ttcggcatgt      131400
```

```
tgaccaggct ggtttcaaaa ctgctgatct caagtgatcc gctcgcctct gcctcccaaa    131460
gtgctgggat tacaggcatg agccaccgtg cccggcctat ttcttgagtt tctttctttt    131520
tctgcttctt gtagtgccac ccctgccctg ccacctagtt ttatgttctc catatgttag    131580
tttgcagaag gaaattaatc tagtgaccag ctgcttctct gtgtccaagg gcctaaggga    131640
acttgttaga atgctggctt acttgtctgt ctggtgagtc cacagaactt ggggtgtgtg    131700
taatttcacc tttttatttg tcctgtagag tccaacagct gagaaagatg tctgctggtg    131760
tcttgcctgt cccttctgcc ctcaggtttt atgtattatg cagaagccac agggagaaca    131820
tgagaattcc tagaagttct agtaacagaa tggtctgtca gttatagatt atttccttca    131880
gggcttagag gcaggtaggt agcccaaggc attttgagct tttgaaattc atagttattt    131940
gacgtggaca agggtgggtt gggaacagtg tcatatccaa ccttacactg aagaaaggat    132000
gccatggatt ggacagaaag atgtcactta aaattatgaa atgattaagt ctgttaccag    132060
tgaggagaaa tctcctcctg tatctaagaa cagttcttgt acatggtatg gttttagct     132120 gaaggaacaa tcactttgcg attttggatg catggcccag ttgtttctcc agcaatgaga    132180
tgccatgagc atggcagaga gcagtaagac gctatgcagc ctttaggttt gggtctggga    132240 gtcctttta aaaatggga gagggagtt aggaaatgcc tcatagcttt taagaagat        132300 cctgggatcg tatgggctcc tgtatcccag ctagaaccag tgactgggtg ctgaacgggc    132360
tgggtgccac agcatgccct caagccagtg agaggagtta gggctgccac tgtgcttata    132420
tgcccttttc aggttttttt gttcatttgt gtttttgaga cggagtcttg ttctgttgcc    132480
cagagcaagt ggagtgcagt ggtacgatct tagctcactg cagcctccat ctcccgagct    132540
cttgattctc gtgcctcagc ctcccaagta gctgggacta caggtgtgcg ccaccacgca    132600
cggccaatat ttcttttcag tagataggtt ttgccttttt ggccaggctg gtctcgaatt    132660
cctgacatca agtgatccac ctgcctcagc ctcccaaagt gctgggatta caggcgtgag    132720
ccactgtgcc gggccgtttt caggcactta aatttaatcc tggtgaagta ggtattatca    132780
ctatgtgtct tctgcacatg aagaaactga aactcaaaaa cactgataac ttctttgcac    132840
atattggggt ttgaggccaa gacgtctggc tggagaggcc acacgcttgc cctgcccta    132900 agaacatggt gggctgggcg tgggggccca cacatgtaat cccagcactt tgggaggccg    132960
aggcaggcag atcacgaggt caggagttcg agaccagccc ggccaacatg gtgaaacccc    133020
gtctctactg aagtacaaa aattagctgg gcgtggaggc aggtgcctgt agttgcggct    133080
acttgagagg ctgaggcaga ggaatcgctt gacccaggag gcggaggttg cagcgagccg    133140
agatagcgcc actgcactcc agcctgggag acagagtgag acctgtctcc cctccaaaaa    133200
aaaaaaaaag aactcggtgt ttgctctgca ggtttgctgg ctaccttctc tttttcagtac   133260 actgaaaata gcagcttgtg ttgtttacct actctttgat ccttttttttt tttttttttcc 133320 tcttggcctc aggctcctgt tctggatgtc agatatgcat ctgcctcctg agaaactggt    133380
ggctttgaac acttggtgtg gactactgtg ttatccggga tatcaggtat tatgagacat    133440
cacctagcca tctgcatcac atctctctgg acaagcagct attaccaaaa aaggcatata    133500
cttccagtcc tgtgctccat ctgccttaat tctttgctcg ttcctccatg ttggcgccac    133560
ttcccagaga gctccactgc atctcacact ctgcccacgt gctggggaag tctcacggcc    133620
tgcacatctc ttgtgactct gggaaccgcc tctcccgccg gagccccga gccccaccaa     133680 tggcagctct tcccagtcag cagcttcaga gcaggcagtc tccttggaag gcccgactct    133740
gttcctgcat ggcctgcagt ttctactttg tgcatagagt cattttcaga gtcaccgcga    133800
```

```
ccctgttggc cttctagaaa gtttcttttg ttcttttctg agacaaccac ctaagtgata 133860
atacgctttt ttggaaacta atatatattg ccagactgca tcataacctt tatcatgcca 133920
agcatcctga tgcaactcac atttccctaa acatggggta cagttatgat ttataaattg 133980
agttggctta aatctccctc ttctcccttc ccaagtgtta caaagatcat ttactgcaac 134040
tgtcgttgga cactgtagct taaagggaac gtggacctca atgctttctg ccttcaactt 134100
ttcagcattg tgaccccagg gtggttgcca ccccatcttt tcctgacccc ccccacccccc 134160 ccacctccaa gaggttcggc ccacatcact gtacctggtg cttgtaaatt tggaattggt 134220
gccttctcct tttggcaacc atggttatca atccttttc tgttttagtg tcttatttct 134280
tctttcaagt tatttgctag ccaaagatga catcactgag attaggagac aggggagagc 134340
ttgctgcaga ttctgacagt gcagatttta aatgtcagga tattagaata gctggcgctg 134400
gtttatgaaa gctgcgcgtt gttccgcgtt ctctcggtgt gcctggcctt ttatgtggca 134460
ctctgtatgt cagtttgtgt ccttcatgtg ctgatgtgat tacacaaaca ccatgcactc 134520
tcttttcata tcagagtaca ggacagagaa gtgatcaatg tattggtcta gtgagactga 134580
gatgaaaaga aataacctac agagtggtct gtaatgcctt ttggttggac tgggaacaag 134640
taaaaatttc taataaacat tttgagactt ccagaatcac ttttgttatc ttatcagacc 134700
atgggcctgc tgagggttga gcagacagcc tgcattctaa catacctgt tcccacccca 134760 cggccattca gactgcactc aatacgctga agtcgctttt gttgttgttg ttgttgtttg 134820
catcatttgg attttttcc tgctttcaat accaaaaaaa tgcagatgct ttaaggccta 134880
aacagaattc tgaagaattt aaaatatgca attaaagttt gatatgtttt gtctcccaag 134940
caccttgttt tttgttgttg ttgttgttgt tgaagtcagc tgattttctc tttagaaaga 135000
gggtcagcta gaaacctagg tttttggaa ttgtaaattt ttttttagta tagtctggag 135060
agaaaggtca ttcaaaagga aagtacaatg ggacttgctg cccttcatca tctcgttccc 135120
gtgccaggtg tgtgttggtc acgtaaaagc ctgggaagca tcagaggagt cccggattgc 135180
tgctgctacc tggagacagg gttagcaaaa taacactagt gatgagggag aggcttcttt 135240
tcaccataag cctgctgtgt acaccgaggg cggcaggaga agcatgggaa ggagtcagcc 135300
taagtttgca cattgcataa agggtacact aaggtatgag ctgaagcttt aggttctccg 135360
tgcttccctc aagacctcct tcttgctaac agaagcagta ggcaattgct gcagtgcgtt 135420
tctcaccctg ccaataggtc tgtctgtatc tctgttaagg aaaatagcct ggtccctcct 135480
ggcagtgctt ggaagcttga tgctaatttt tatatagcgt ggcaaactga ccagcagtgc 135540
caggccttga tctgtattct gcactatccc tttacttggt tcctggcact gaatggtctc 135600
cagccctgaa gaatcacgtg tgatcacagc agctgacctg ggctttctcc ccgagaggaa 135660
ggggcatgtc atttttattt gacagaggga aaatgggagc tgtccttgac tgcctttgtt 135720
gtgctttccc gcgtaagata gcactgtgtt ttaaactgtt gcattacact gtctttgcaa 135780
tgatgtaaat gtaagaaatc acttagcttt aaaagcgcag tggtttgatc ttatttatat 135840
gaagactttt taacatatca agaattaggt gcattggcag gtagggtttg gggtgtgata 135900
actgcttcag atggaatgtt cacttaagct ttgtcttctt aaaaattatc aatgtgaatg 135960
tcataattat atatattttt gtggaaaatt ttctcctaag tataagttat tgtgcaaaat 136020
atagtgtcat tgatgcaaat aatagtttaa cttttagttt agaactccta aaagatataa 136080
attgtattgc atatgcatta aaagtttgtt ttatttaatt ttatgtagat gtgtgaagtg 136140
```

```
ttaggtaaaa ttttttttcac ttatccattt aaacaccttg ttacttgaat attgtgttga    136200
ctggtctgca acagtgatcc attctgtaat atagctcttt taactgggaa ggaaccacac    136260
cccagttgtg ccgattacat tagtgttggc acacagtcgg gtgctagtgt aacacaaatg    136320
ccgcgttgtc tgggtgtaca gtgtttgtgg agacgccact tcctcaaaat ggttttttgat   136380 tgttttttaac ctataagacg ttctgatgct cacaaacctc tattcaacac acaaaacaaa   136440
catgaaaagg tagttagttg ggttgtaaca gcttactggg gtggactcat aaaacagtgg    136500 cttttctgttc atctaaagtt tcctcagata ccacagacca ctgttaagtg tgctcattgt   136560
cactttaaat ttcaacgata ccctattttt gtcattctaa atatcagatg tactattggt    136620
ataattgcac accaaaaata agccaaacag tgcattacgc taactggatc cctgctttta    136680
tgtgagctaa ggaaagatgg agccaactcc aacgagggcc tcttttttctc tcttgtctag   136740 cctgtttcta aaccgaatga tccaggattc aagcttctat tgtcaagtga aactttcctc    136800
agatggactc caggtagcca ggtcacctaa acctagtggt cctgtgcgat gctctttctg    136860
ccagtccctg aatctctgca gcttctctta cctgtcttac ctgtagtaaa gcacaattgc    136920
agtggcgtcg cattcagaag aagggaaggt cagcagaggc tatgcatgtt gtgtgatgat    136980
gagtgtttac agccaccttc tcctaaaacg aaatttatac cggggtggat agtattccat    137040
taggtagact tatcgacttt gctaagtgct ttttagacag cttaaaaaat tttcaagatt    137100
ttaaaagatg tataaggtta agtttgcaaa tataatggaa atgctgtata tcttttgaag    137160
tgatgaaatc cacgttggaa ttttaaagaa aatatgttgt aataatgctg ttgtaagtaa     137220 tatttttaatg tctctttgcc tgttttctat ttcagcacat tcattgtggt gaatgttcat    137280
agcattataa ctgcttagcc attgaatgat aacatttgtt agtggaaatt ggaaaattta    137340
tttgtgaaat tctgcagaat tcatttttct atttccaata tttgctgagg ttaaataaaa    137400 atttttcaagc cattgatgta ataaaatatg aaatgaaagc attttctgca cccccacgct    137460
ccatcaaagc agtacccttc cctgtaacaa agtgggggttc tttctttcct tttaagtgag    137520 gcttgggggtt tccaaatgtt gaatttcttc caaatcagac cctgtggaaa cactgccagg    137580 gatgccttttt gttttttagcc ttttgctcta cctgaactga cattctttttt tatatatgat  137640 aatttttatag ttggaatcaa gttgaagcac atgaattcat aaagtttgtg atagttgtgg    137700
gtttaaatgc aagggttcag taagaggcat ttttcccccc atgggtggat tttctttttt    137760
cagcctgacc aggcttttgg cctgatacct ggaggcagga tggtggcagt gcagaggcaa    137820
gatcactgcc gctgtggcct ctgctcagcc aagagtgcat gcacaccagt gccggtagtt    137880
tcctgagtag cgtgaagaag ctggcggtgg ctgtggtctc atggtcttcc ctttattagc    137940
tgggatgtag aatttgatta gatgactact gtagattggg gctagaagtc cagtgcacta    138000
tccattgtgc cactgagctt gctcactaga taacttctat agaaacccaa tttctaggtc    138060
caggcagatg gggcccctgt gtgtgactgc acagtgtagg aggggttgtag aagggtgacc   138120 gggtccagcc ttcccagcgt ggacagtcta gtggaggaca ctgcacatat cctccaggtg    138180
acagcagtca gcaccacggc gagtggagcc acagctacag gcaggtctgg gagggaggct    138240
gcagctgcct cgcatctaat ttagagagtg cctgtcccgg agctgagcct gtggaaaggg   138300
gagagggtct gcttgggtga gggtggcacc tagggggcga ggccaagagt gttgggacct    138360
ccgctgtgat ttgtgaaggt ggcttgtggt ctagaacaag aggaaatgag tgccaaggac    138420
agagaggagg aaggttgagg ccaaggtggc cccctgccaa gatgctgctg gacatctgct    138480
aggttgggca ctgaaggtgg agccatttgg acttggcctt tagtgacttc aaagaacccc    138540
```

```
gggcgatggc tgaggctggg aagagggagc tatggagggt tgagggagag cccctctcaa  138600
agactggcct aacttgagcg cgtgcaaggg cacaggatag gaagggatag caggcgggct  138660
gtgagtcccg agtcagacac atggaggccc tggctccagc tcccttttct cggactgagg  138720
gggaaaaaaa cacctgtata caggtgtaga tgaggcgcct ctgtgcctca cttcccatca  138780
tcttggccct ccccacaacc ccggcttcag acaggtgtga ctgcagcacc ctgaggtagg  138840
tgacctaggg gagctcagga acagcagcct ggaagtagca gggagctcca tccccagggg  138900
cagctctggg taatctgggt aaggcagcca tagacagcag ctcccccctca gcggcccccct  138960 gcagagacca gctcagaaat ggtctaggac tgattctcct tccctgcctc acttttttctg  139020 gcccctact tctgttgcct gggattggtt tctaaagcaa accatttacc cacaaagcct  139080
catctcaggc tctgcttttg cggggaatct aggccaagac agcaccacag tgagaattac  139140
aaggctcggg agaggcctgg tgaggtccct gccaggcctg tcccagcctt tcagcttatg  139200
ggagggagag atcttgagag cacttggtgc tgacactgct ggaaaggcca tagtacc    139257

<210> SEQ ID NO 12
<211> LENGTH: 521
<212> TYPE: DNA
<213> ORGANISM: Homo sapiens
<220> FEATURE:
<221> NAME/KEY: unsure
<222> LOCATION: 51
<223> OTHER INFORMATION: unknown
<221> NAME/KEY: unsure
<222> LOCATION: 52
<223> OTHER INFORMATION: unknown
<223> OTHER INFORMATION:

<400> SEQUENCE: 12
agtgctctca aagaaaaact tgatggtgga atagaaccat atcgacttca nnaggtagga    60
ttatgttaac atcatcttag aagtcatatt caagttttac atgtttaaga atttaatatc   120
ggtgtgatac aatcccagta tacatctctt ggaagagtat atggacataa ttttatgaac   180
ccagttgatg ttaaaattcc gataagagaa aatgaaaggt tcgttaagct cataaggaca   240
tactcatctc taaatgtaat gtgctaaaat gactcatttg gatatccagg tcattcagaa   300
atgtaatgca cgttggacta cagaagagca gcttctcgcc gtacaaggta gggggaagtt   360
cttctaaaga gtttaggagg ccggctgtgg tggctcacac ctgtaatccc aacattttgg   420
aaggttgacg catttgcttg agcccaggag ctcaaggctg cattgatcca tgatcacacc   480
actgcattcc agcctggaca acagagggag accctgactt t                      521

<210> SEQ ID NO 13
<211> LENGTH: 409
<212> TYPE: DNA
<213> ORGANISM: Homo sapiens
<220> FEATURE:

<400> SEQUENCE: 13
cagacaaaca gtgctctcaa agaaaaactt gatggtggaa tagaaccata tcgacttcca    60
gagccatcag gaaatatggc cgagattttc aggcaatctc agacgtgatt gggaacaaat   120
cagtggtaca agtgaaaaac ttttttgtaa atgatcgacg ccgcttcaac atagatgaag   180
ttttacaaga atgggaggca gaacatggta agaagagac caatgggccc agtaaccaga   240
agcctgtgaa gtcccagat aattccatta agatgcccga agaggaagac gaggctcctg   300
ttctggatgt cagatatgca tctgcctctt gagtaactgg tggctttgta cacttggtgt   360
```

-continued ggactactgt gttatccggg atatcaggta tatgagacat cactatcca        409

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
tggacgagcc cgagctgcct        20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
ttgggtgacc agaccaacat        20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
gcttctgaca gattttgatt        20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
tcccaagagc ctgttccatg        20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
caaatcagcc aatgactttt        20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gacttgctat agatttatct        20

<210> SEQ ID NO 20
<211> LENGTH: 20
<212> TYPE: DNA

-continued

```
<213> ORGANISM: Artificial Sequence
<220> FEATURE:
<223> OTHER INFORMATION: Antisense Oligonucleotide

<400> SEQUENCE: 20
actagtttta gtcctcgtct                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tgtcaatggg attgtttcca                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
acctgaggaa ctgtctcagt                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
tttttgacct gaggaactgt                                              20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
acattccttt tggaggtttc                                              20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
tcttcttgag aaagaaacat                                              20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ccacatcttc ttgagaaaga                                              20
```

```
<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
acagcctcca catcttcttg                                                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
agcagtggca ttggcagaaa                                                    20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
attccaccat caagttttc                                                     20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tctgaatgac ctctggaagt                                                    20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
attacatttc tgaatgacct                                                    20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
tacggcgaga agctgctctt                                                    20

<210> SEQ ID NO 33
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 33
atggcttgta cggcgagaag                                                    20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ttcctgatgg cttgtacggc                                                    20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
aaaaagtttt tcacttgtac                                                    20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gcgtcgataa tttacaaaaa                                                    20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
catctatgtt gaagcggcgt                                                    20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
aacttcatct atgttgaagc                                                    20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tgtaaaactt catctatgtt                                                    20

```
<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
attcttgtaa aacttcatct                                                    20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
tcccattctt gtaaaacttc                                                    20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gaacaggagc ctcgtcttcc                                                    20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
tcaggaggca gatgcatatc                                                    20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
agtccacacc aagtgttcaa                                                    20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
cagatggcta ggtgatgtct                                                    20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide
```

| | |
|---|---|
| <400> SEQUENCE: 46 | |
| tgatgcagat ggctaggtga | 20 |

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

| | |
|---|---|
| <400> SEQUENCE: 47 | |
| agatgtgatg cagatggcta | 20 |

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

| | |
|---|---|
| <400> SEQUENCE: 48 | |
| tttggtaata gctgcttgtc | 20 |

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

| | |
|---|---|
| <400> SEQUENCE: 49 | |
| caagagatgt gcaggccgtg | 20 |

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

| | |
|---|---|
| <400> SEQUENCE: 50 | |
| caggccatgc aggaacagag | 20 |

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

| | |
|---|---|
| <400> SEQUENCE: 51 | |
| aactgcaggc catgcaggaa | 20 |

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

| | |
|---|---|
| <400> SEQUENCE: 52 | |
| aagtagaaac tgcaggccat | 20 |

<210> SEQ ID NO 53
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 53
ggttgtctca gaaaagaaca                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aaaagcgtat tatcacttag                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
atcataactg taccccatgt                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
gtgatgtggg ccgaacctct                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
aaggagaagg caccaattcc                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
atcagcacat gaaggacaca                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
```

```
aaattttttac ttgttcccag                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
cctaggtttc tagctgaccc                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
agacctattg gcagggtgag                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
cacgtgattc ttcagggctg                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ctgctgtgat cacacgtgat                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
atatgttaaa aagtcttcat                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ttcttgatat gttaaaaagt                                               20

<210> SEQ ID NO 66
<211> LENGTH: 20
<212> TYPE: DNA
<213> ORGANISM: Artificial Sequence
```

```
-continued

<220> FEATURE:
<223> OTHER INFORMATION: Antisense Oligonucleotide

<400> SEQUENCE: 66
acaaagctta agtgaacatt                                                    20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tgtgttacac tagcacccga                                                    20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
aacactgtac acccagacaa                                                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
cttataggtt aaaaacaatc                                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ctgatattta gaatgacaaa                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
tttagaaaca ggctagacaa                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
acgccactgc aattgtgctt                                                    20
```

```
<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
cttcccttct tctgaatgcg                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
cggtataaat ttcgttttag                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
cctaatggaa tactatccac                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
tatatttgca aacttaacct                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
atgaatgtgc tgaaatagaa                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ccctcagcaa atattggaaa                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 79
gagtaagaaa gagaggttac                                                    20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
caggtgtctc gatctccatg                                                    20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
cctcccaaag tgccaggatt                                                    20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
aatcccagct actcgggagg                                                    20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
gccagtttgg cttgggagaa                                                    20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ttcatcctcg ctggaagaca                                                    20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
tcagatttac ctcgtcttcc                                                    20

<210> SEQ ID NO 86
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
gaacaggagc ctgaggccaa                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
gtccttatga gcttaacgaa                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
tctgaatgac ctggatatcc                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ttccccctac cttgtacggc                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
gtgtgagcca ccacagccgg                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
ctgatggctc tggaagtcga                                              20
```